(12) United States Patent
Cheng et al.

(10) Patent No.: US 9,126,971 B2
(45) Date of Patent: Sep. 8, 2015

(54) ANTI-VIRAL NUCLEOSIDE ANALOGS AND METHODS FOR TREATING VIRAL INFECTIONS, ESPECIALLY HIV INFECTIONS

(75) Inventors: Yung-chi Cheng, Woodbridge, CT (US); Hiromichi Tanaka, Tsuzuki-ku (JP); Masanori Baba, Kagoshima (JP)

(73) Assignee: YALE UNIVERSITY, New Haven, CT (US)

( * ) Notice: Subject to any disclaimer, the term of this patent is extended or adjusted under 35 U.S.C. 154(b) by 407 days.

(21) Appl. No.: 13/465,315

(22) Filed: May 7, 2012

(65) Prior Publication Data
US 2012/0252751 A1 Oct. 4, 2012

Related U.S. Application Data

(62) Division of application No. 12/583,229, filed on Aug. 17, 2009, now Pat. No. 8,193,165, which is a division of application No. 10/781,305, filed on Feb. 18, 2004, now Pat. No. 7,589,078.

(60) Provisional application No. 60/448,554, filed on Feb. 19, 2003.

(51) Int. Cl.
*A61K 31/7072* (2006.01)
*C07D 405/04* (2006.01)
(Continued)

(52) U.S. Cl.
CPC ............ *C07D 405/04* (2013.01); *A61K 31/522* (2013.01); *A61K 31/675* (2013.01);
(Continued)

(58) Field of Classification Search
None
See application file for complete search history.

(56) References Cited

U.S. PATENT DOCUMENTS

| 4,978,655 A | 12/1990 | Lin et al. |
| 5,739,396 A | 4/1998 | Trost et al. |

(Continued)

FOREIGN PATENT DOCUMENTS

| JP | 05-230058 | 9/1993 |
| JP | 05230058 | 9/1993 |

(Continued)

OTHER PUBLICATIONS

Hai et al., "Species- or Isozyme-Specific Enzyme Inhibitors. 7. Selective Effects in Inhibitors of Rat Adenylate Kinase Isozymes by Adenosine 5′-Phosphate Derivatives", Journal of Medicinal Chemistry 1982, 25:806-812.

(Continued)

*Primary Examiner* — Traviss C McIntosh, III
(74) *Attorney, Agent, or Firm* — Henry D. Coleman; R. Neil Sudol

(57) ABSTRACT

The present invention relates to novel compounds according to the general formulas I, II, III, IV or V:

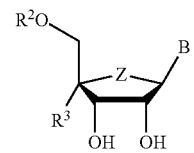

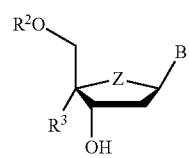

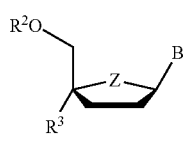

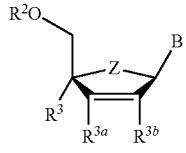

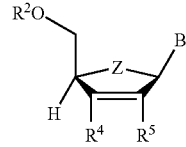

wherein B is nucleoside base according to the structure:

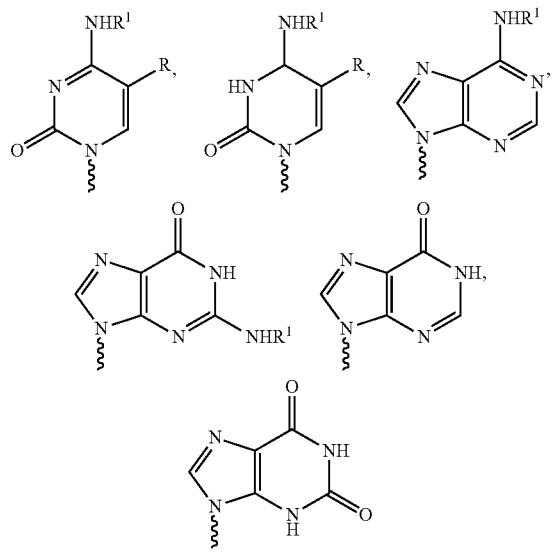

and the remaining variables as defined in the specification, and pharmaceutical compositions comprising the compounds. The compounds are useful interalia as anti-viral agents in viral therapy.

31 Claims, 16 Drawing Sheets

(51) Int. Cl.
| | |
|---|---|
| A61K 31/522 | (2006.01) |
| A61K 31/675 | (2006.01) |
| A61K 31/7076 | (2006.01) |
| C07H 19/06 | (2006.01) |
| C07H 19/10 | (2006.01) |
| C07H 19/16 | (2006.01) |
| C07H 19/20 | (2006.01) |

(52) U.S. Cl.
 CPC ......... *A61K31/7072* (2013.01); *A61K 31/7076* (2013.01); *C07H 19/06* (2013.01); *C07H 19/10* (2013.01); *C07H 19/16* (2013.01); *C07H 19/20* (2013.01)

(56) References Cited

U.S. PATENT DOCUMENTS

| | | | |
|---|---|---|---|
| 5,763,418 | A | 6/1998 | Matsuda et al. |
| 5,880,294 | A | 3/1999 | Nomura et al. |
| 6,291,670 | B1 | 9/2001 | Ohrui et al. |
| 6,333,315 | B1 | 12/2001 | Ohrui et al. |
| 7,589,078 | B2 | 9/2009 | Cheng et al. |
| 8,193,165 | B2 * | 6/2012 | Cheng et al. ................ 514/49 |
| 2004/0006002 | A1 | 1/2004 | Sommadossi et al. |

FOREIGN PATENT DOCUMENTS

| | | |
|---|---|---|
| JP | 6-80688 | 3/1994 |
| JP | 06-080688 | 3/1994 |
| JP | 10-298194 | 11/1998 |
| JP | 11-349596 | 12/1999 |
| WO | WO 00/69877 | 11/2000 |
| WO | WO 02/069876 | 9/2002 |
| WO | WO 02/100415 | 12/2002 |
| WO | WO 03/026589 | 4/2003 |
| WO | WO 03/062255 | 7/2003 |

OTHER PUBLICATIONS

Hai et al., "Species- or Isozyme-Specific Enzyme Inhibitors. 9. Selective Effects in Inhibitors of Rat Pyruvate Kinase Isozymes by Adenosine 5'-Diphosphate Derivatives", Journal of Medicinal Chemistry 1982, 25:1184-1188.
Kodama et al., "4'-Ethynyl Nucleoside Analogs: Potent Inhibitors of Multidrug-Resistant Human Immunodeficiency Virus VArients in Vitro", Antimicrobial Agents and Chemotherapy 2001, 45:1539-1546.
Riddler et al., "Antiretroviral activity of Stavudine (2',3'-dedihydro-3'-deocythymidine, D4T)", Antiviral Research 1995, 27:189-203.
Waga et al., "Studies on sugar-modified nucleosides. Part I. Synthesis of 4'-C-methylnucleosides", Bioscience, Biotechnology and Biochemistry 1993, 57:1433-1438.
Hrebebecky et al., "Synthesis of 1-(2,3-dideoxy-4-C-methyl-beta-D-glycero-pent-2-enofuranosyl)thymine, 1-(2,3-dideoxy-4-C-methyl-beta-D-glycero-pentofuranosyl)thymine, and 1(4-C-Azidomethyl-2-deoxy-beta-D-Threo-puntofuranosyl)thymine", Collect. Czech. Chem. Commun., vol. 58, pp. 1668-1674, 1993.
Haraguchi et al., Allylic Substitution of 3',4'-Unsaturated Nucleosides: Organosilicon-based Stereoselective Access to 4'-C-Branched 2',3'-Didehydro-2',3'-dideoxyribonucleosides, J. Org. Chem., vol. 61, pp. 851-858.
Haraguchi et al., Nucleic Acids Research Supp., 133-134, 2002.
Caplus AN 1994:164819.
Tabata et al. "anti-tumor Mechanisms of 3'-ethynyluridine and 3'-ethynylcytidine as RNA synthesis inhibitors: development and characterization of 3'-ethynyluridine-resistant cells." *Cancer Letters* 1997, 116:225-231.
August, E. M., M. E. Marongiu, 'T. S. Lin, and W. H. Pnisoff. 1988. Initial studies on the cellular pharmacology of 3'deoxythymidin-2'-ene (d4T): a potent and selective inhibitor of human immunodeficiency virus. *Biochem Pharmacol* 37:4419-22.

Bridges, E. G., G. E. Dutschman, E. A. Gullen, and Y. C. Cheng. 1996. Favorable interaction of beta-L(−) nucleoside analogues with clinically approved antiHTV nucleoside analogues for the treatment of human immunodefciency virus. *Biochem Pharmacol* 51:731-6.
Brinkman, K., H. J. ter Hofstede, D. M. Burger, J. A. Smeitink, and P. P. Koopmans. 1998. Adverse effects of reverse transcriptase inhibitors: mitochondrial toxicity as common pathway. *Aids* 12:1735-44.
Browne, M. J., K. H. Mayer, S. B. Chafee, M. N. Dudley, M. R. Posner, S. M. Steinberg, K. K. Graham, S. M. Geletko, S. H. Zinner, S. L. Denman, and et al. 1993. 2',3'-didehydro-3'-deoxythymidine (d4T) in patients with AIDS or AIDSrelated complex: a phase I trial *J Infect Dis* 167:21-9.
Chen, C. H., and Y. C. Cheng. 1989. Delayed cytotoxicity and selective loss of mitochondrial DNA in cells treated with the anti-human immunodeficiency virus compound 2',3'-dideoxycytidine. *J Biol Chem* 264:11934-7.
Chen, C. H., M. Vazquez-Padua, and Y. C. Cheng. 1991. Effect of anti-human immunodeficiency virus nucleoside analogs on mitochondrial DNA and its implication for delayed toxicity. *Mol Pharmacol* 39:625-8.
Cheng, Y. C. 1978. Thymidine Kinase from Blast Cells of MyelocytidLeukemia, p. 365-371, *Methods in Enzymology*,vol. LI Academic Press, New York.
Coates, J. A., N. Cammack, H. J. Jenkinson, A. J. Jowett, M. I. Jowett, B. A. Pearson, C. R. Penn. P. L. Rouse. K. C. Viner, and J. M. Cameron. 1992. (−)-2'-deoxy-3'-thiacytidine is a potent, highly selective inhibitor of human immunodeficiency virus type 1 and type 2 replication in vitro.*Antimicrob Agents Chcmother* 36:733-9.
Coates, J. A., N. Cammack, H. J. Jenkinson, 1. M. Mutton. B. A. Pearson, R. Storer, J. M. Cameron, and C. R. Penn. 1992. The separated enantiomers of 2'-deoxy-3'-thiacytidine (BCH 189) both inhibit human immunodeficiency virus replication in vitro*Antimicrob Agents Chemother* 36:202-5.
De Clercq, E. 1994. HIV resistance to reverse transcriptase inhibitor. *Biochem Pharmacol* 47:155-69.
Doong, S. L., C. H. Tsai, R. F. Schinazi, D. C. Liotta, and Y. C. Cheng. 1991. Inhibition of the replication of hepatitis B virus in vitro by 2',3'-dideoxy-3'-thiacytidine and related analogues. *Proc Natl Acad Sci U S A* 88:8495-9.
Dutschman, G. E., E. G. Bridges, S. II. Liu, E. Gullen, X. Guo, M. Kukhanova, and Y. C. Cheng. 1998. Metabolism of 2',3'-dideoxy-2',3'-didehydro-beta-L(−)-5-fluorocytidine and its activity in combination with clinically approved antihuman immunodeficiency virus betaD(+) nucleoside analogs in vitro.*Antimicrob Agents Chemother* 42:1799-804.
Feng, J. Y., A. A. Johnson, K. A. Johnson, and K. S. Anderson. 2001. Insights into the molecular mechanism of mitochondrial toxicity by AIDS drugs*J Biol Chem* 276:23832-7.
Gelmon, K., J. S. Montaner, M. Fanning, J. R. Smith, J. Falutz, C. Tsoukas, J. Gill, G. Wells, M. O'Shaughnessy, M. Wainberg, and et at. 1989. Nature, time course and dose dependence of zidovudine-related side effects: results from the Multicenter Canadian Azidothymidine Trial. *Aids* 3:555-61.
Gosselin, G., R. F. Schinazi, J. P. Sommadossi, C. Mathe, M. C. Bergogne, A. M. Aubertin, A. Kim, and J. L. Imbach. 1994. Anti-human immunodeficiency virus activities of the betaL enantiomer of 2',3'-dideoxycytidine and its 5-fluoro derivative in vitro.*Antimicrob Agents Chemother* 38:1292-7.
Hamamoto, Y., H. Nakashima, T. Matsui, A. Matsuda, T. Ueda, and N. Yamamoto. 1987. Inhibitory effect of 2',3'-didehydro-2',3'-dideoxynucleosides on infectivity, cytopathic effects, and replication of human immunodeficiency virus*Antimicrob Agents Chemother* 31:907-10.
Haraguchi, K., S. Takeda, H. Tanaka, T. Nitanda, M. Baba, G. E. Dutschman, and Y. C. Cheng. 2003. Synthesis of a Highly Active New Anti-HIV Agent 2', 3'-Didehydro-3'deoxy-4'-ethynylthymidine. *Bioorg Med Chem Letter* 13:3775-3777.
Johnson, A. A., A. S. Ray, J. Hanes, Z. Suo, J. M. Colacino, K. S. Anderson, and K. A. Johnson. 2001. Toxicity of antiviral nucleoside analogs and the human mitochondrial DNA polymerase.*JBiol Chem* 276:40847-57.

(56) References Cited

OTHER PUBLICATIONS

Larder, B. A. 1995. Viral resistance and the selection of antiretroviral combinations. J *Acquir Immune Defic Syndr Hum Retrovirol* 10 Suppl 1:S28-33.

Larder, B. A., B. Chesebro. and D. D. Richman. 1990. Susceptibilites of zidovudinesusceptible and -resistant human immunodeficiency virus isolates to antiviral agents determined by using a quantitative plaque reductionassay. *Antimicrob Agents Chemother* 34:436-41.

Lee, L. S., and Y. C. Cheng. 1976. Human deoxythymidinekinase. I.Purification and general properties of the cytoplasmic and mitochondrial isozymes derived from blast cells of acute myelocvtic leukemia.*J Biol Chem* 251:2600-2604.

Lewis, W., and M. C. Dalakas. 1995. Mitochondrial toxicity of antiviral drugs*Nat Med* 1:417-22.

Lin, T. S., M. Z. Luo, M. C. Liu, S. B. Pai, G. E. Dutschman, and Y. C. Cheng. 1994. Antiviral activity of 2',3'-dideoxy-beta-L-5-fluorocytidine (beta-L-FddC) and $2^1$,3'-dideoxy-beta-L-cytidine (beta-L-ddC) against hepatitis B virus and hunan immunodeficiency virus type 1 in vitro. *Biochem Pharmacol* 47:171-4.

Lin, T. S., M. Z. Luo, M. C. Liu, S. B. Pai, G. E. Dutschman, and Y. C. Cheng. 1994. Synthesis and biological evaluation of 2',3'-dideoxy-L-pyrimidine nucleosides as potential antivial agents against human immunodeficiency virus (HIV) and hepatitis B virus (HBV)*J Med Chem* 37:798-803.

Lin, T. S., M. Z. Luo, M. C. Liu, Y. L. Zhu, E. Gullen, G. E. Dutschman, and Y. C. Cheng. 1996. Design and synthesis of 2',3'-dideoxy-2',3'-didehydro-beta-L-cytidine (beta-I.-d4C) and 2',3'-dideoxy 2',3'-didehydro-beta-L-5-fluorocytidine (beta-LFd4C), two exceptionally potent inhibitors of human hepatitis B virus (HBV) and potent inhibitors of human immunodeficiency virus (HIV) in vitro.*J Med Chem* 39:1757-9.

Lin, T. S., R. F. Schinazi, M. S. Chen, E. Kinney-Thomas, and W. H. Prusoff. 1987. Antiviral activity of 2,'3'-dideoxycytidin-2'-ene (2',3'-dideoxy-2',3'-didehydrocytidine) against human immunodeficiency virus in vitro.*Biochem Pharmacol* 36:311-6.

Lin, T. S., R. F. Schinazi, and W. H. Prusoff. 1987. Potent and selective in vitro activity of 3'deoxythymidin-2'-ene (3'-deoxy-2',3'-didehyrdothymididne) against human Immunodeficiency virus. *Biochem Pharmacol* 36:2713-8.

Lu, Z. H., R. Zhang, and R. B. Diasio. 1993. Comparison of dihydropyrimidine dehydrogenase from human, rat, pig and cow liver. Biochemical and immunological properties*Biochem Pharmacol* 46:945-52.

Maag, H., R. M. Rydzewski, M. J. McRoberts, D. Crawford-Ruth, J. P. Verheyden, and E. J. Prisbe. 1992. Synthesis and anti-Hiv activity of 4'-azido- and 4'-methoxynucleosides.*J Med Chem* 35:1440-51.

Medina, D. J., C. H. Tsai, G. D. Hsiung, and Y. C. Cheng. 1994. Comparison of Mitochondrial Morphology, Mitochondrial DNA Content, and Cell Viablity in Cultured Cells Treated with Three Anti-Human hmunodeficiency Virus Dideoxynucicosides*Antimicrob Agent. Chemother* 38:1824-1828.

Mellors, .J. W., G.E. Dutschman, G..J. Im L. Tramontano, S. R. Winkler, and Y. C. Cheng. 1992. In vitro selection and molecular characterization of human immunodeficiency virusl resistant to nonnucleoside inhibitors of reverse transcriptase*Mol Pharmacol* 41:446-51.

O-Yang, C., H. Y. Wu, B. Fraser-Smith, and K. A. M. Walker. 1992. Synthesis of 4'-Cyanothymidinc and Analogs as Potent Inhibitors of HIV.*Tetrahedron Letters* 33:37-40.

Parker, W. B., and Y.C.Cheng.1995."Disruption of Energy Metabolism and Mitochondrial Function", p. 483-490, *Neurotoxicology: Approaches and Methods*.Academic Press Inc., New York.

Parker, W. B., and Y. C. Cheng. 1994. Mitochondrial Toxicity of Antiviral Nucleoside Analogs. *The Journal of NIH Reasearch* 6:57-61.

Richman, D. D. 1993. Resistance of clinical isolates of human immunodeficiency virus to antiretroviral agents.*Antimicrob Agents Chemother* 37:1207-13.

Richman, D. D., M. A. Fischl, M. H. Grieco, M. S. Gottlieb, P. A. Volberding, O. L. Laskin, J. M. Leedom, J. E. Groopman, D. Mildvan, M. S. Hirsch, and et al. 1987. The toxicity of azidothymidine (AZT) in the treatment of patients withAIDS and AIDS-related complex. A double-blind, placebo-controlled trial.*N Engl JMed* 317:192-7.

Schinazi, R. F., C. K. Chu, A. Peck, A. McMillan, R. Mathis, D. Cannon, L. S. Jeong, J. W. Beach, W. 13. Choi, S. Yeola, and et al. 1992. Activities of the four optical isomers of 2',3'-dideoxy-3'-thiacytidine (BCH-189) against human immunodeficiency virus type 1 in human lymphocytes.*Antimicrob Agents Chemother* 36:672-6.

Sommadossi, J. P., Z. Zhou, M. J. Hitchcock, H. M. McClure, M. el Kouni, and E. Cretton. 1992. Catabolism of 2',3'-Didehydro-2',3-DideoxyThymidine (D4T) in Isolated Hepatocytes and in Rhesus Monkeys.*Proc.Annu. Meeting American Cancer Research* 33:A3253. Univ. of Alabama.

Yarchoan, R., J. M. Pluda. R. V. Thomas, H. Mitsuya, P. Brouwers, K. M. Wyvill, N. Hartman, D. G. Johns, and S. Broder. 1990. Long-term toxicity/activity profile of 2,3'-dideoxyinosine in AIDS or AIDS-related complex.*Lancet* 336:526-9.

Kato Keisuke et al.: "Enantio- and diastereoselective synthesis of 4'-alpha-substituted carbocyclic nucleosides". Tetrahedron: Asymmetry, 9(6), 911-914, 1998.

Kato Keisuke et al.: "Stereoselective synthesis of 4'-alpha-alkylcarbovir derivatives based on an asymmetric synthesis or chemo-enzymatic procedure", Chemical & Pharmaceutical Bulletin, 1999, 47(9), 1256-1264.

Waga Toshiake et al.: "Synthesis and biological evaluation of 4'-C-methyl nucleosides" Nucleosides & Nucleotides 1996, 15(1-3), 287-304.

Haraguchi Kazuhiro et al.: "Allylic Substitution of 3',4'-Unsaturated Nucleosides: Organosilicon-Based Stereoselective Access to 4'-C-Branched 2',3',-Didehydro-2',3'-dideoxyribonucleosides", Journal of Organic Chemistry 1996, 61(3), 851-8.

Cappellacci Loredana et al. "Ribose-Modified Nucleosides as Ligands for Adenosine Receptors: Synthesis, Conformational Analysis, and Biological Evaluation of 1'-C-Methyl Adenosine Analogues", Journal of Medicinal Chemistry 2002, 45(6), 1195-1202.

Kodama Ei-Ichi et al. "4'-Ethynyl nucleoside analogs: potent inhibitors of multidrug-resistant human immunodeficiency virus variants in vitro", Antimicrobial Agents and Chemotherapy, 2001, 45(5), 1539-1546.

De Zwart Maarten et al.: "A functional screening of adenosine analogs at the adenosine A2B receptor: a search for potent agonists" Nucleosides & Nucleotides 19, 17(6), 969-985, 1998.

Yamaguchi Toyofumi et al. "Antileukemic activities and mechanism of action of 2'-deoxy-4'-methylcytidine and related nucleosides". Nucleosides & Nucleotides, 1997, 16(7-9), 1347-1350.

Hai Ton T. et al.: "Species- or isozyme-specific enzyme inhibitors. 9, Selective effects in inhibitions of rat pyruvate kinase isozymes by adenosine 5'-diphosphate derivatives", Journal of Medicinal Chemistry 1982, 25(10), 1184-8.

Hai Ton T. et al.: "Species-or isozyme-specific enzyme inhibitors 7. Selective effects in inhibitions of rat adenylate kinase isozymes by adenosine 5'-phosphate derivatives", Journal of Medicinal Chemistry 1982, 25(7), 806-12.

E. L. Vodovozova et al. "New phospholipids-inhibitors of HIV reproduction. Synthesis and anti-viral activity", Bioorganic chemistry, 1996, 22(6), 451-457.

Berezovskaya Yu. V. et al.: "Creating novel molecular transport systems: the synthesis and antiviral activity of mixed succinates of deoxynucleotides and hydrophobic molecules", Pharmaceutical Chemistry Journal 35(3), 134-138, 2001.

Sejino Keiko et al.: "Facile synthesis of 2',3'-unsaturated nucleosides from 2-deoxyribose", Tetrahedron Letters, 37(34), 6133-6136, 1996.

Palomino Eduardo et al. "A dihydropyridine carrier system for sustained delivery of 2',3'-dideoxynucleosides to the brain" Journal of Medicinal Chemistry , 1989, 32(3), 622-5.

Cramer Janina et al.: "Exploring the Effects of Active Site Constraints on HIV-1 Reverse Transcriptase DNA Polymerase Fidelity" Journal of Biological Chemistry 2002, 277 (46). 43593-43598.

Estrada Ernesto et al.: "In Silico Studies toward the Discovery of New Anti-HIV Nucleoside Compounds with the Use of TOPS-MODE and

(56) References Cited

OTHER PUBLICATIONS the 2D/3D Connectivity Indices. 1. Pyrimidyl Derivatives" .Journal of Chemical Information and Computer Sciences 2002, 42(5), 1194-1203.

Matsuda Akira: "Development of novel radical cyclization-ring expansion reaction and its pharmacochemical development". Farumashia 2002, 38(4), 293-295.

Summerer Daniel et al.: "DNA polymerase selectivity: sugar interactions monitored with high-fidelity nucleodises", Angewandte Chemie, International Edition, 40 (19), 3693-3695.

Kohgo Satoru et al. "Synthesis of the L-enantiomer of 4'-C-ethynyl-2'-deoxycytidine". Bioscience, Biotechnology and Biochemistry 2001, 65(8), 1879-1882.

Kohgo Satoru et al.: "Development of Nucleosides highly potent against multidrug resistant HIV", Tennen Yuki Kagobutsu Toronkai Koen Yoshishu, 2000, $42^{nd}$, 835-840.

Riehokainen Elena et al.: "Stereoselcetive synthesis of 3'-fluoro- and 3'-azido-4'-methyl-2',3;-D-glycero-pentofuranoside-5-fluorouracils" Tetrahedron, 54(34), 10161-10166, 1998.

Ohrui Hiroshi et al.: "Syntheses of 4'-C-Ethynyl-p-D-arabino- and 4'-C-Ethynyl- 2'-deoxy-p-D-ribo-pentofuranosylpyrimidines and -purines and Evaluation of their Anti-HIV Activity", Journal of Medicinal Chemistry 2000, 43(23), 4516-4525.

Kohgo Satoru et al. "Synthesis of 4'-C-ethynyl-p-D-Arabino- and 4'-C-ethynyl-2'-deoxy-beta-D-ribopentofuranosyl pyrimidines, and their biological evaluation", Bioscience, Biotechnology, and Biochemistry, 62(6), 1146-1149., 1999.

Nomura Makoto et al.: "Nucleosides and Nucleotides. 185. Synthesisand Biological Activities of 4'a-C-Branched-Chain Sugar Pyrimidine Nucleosides", Journal of Medicinal Chemistry 1999, 42(15), 2901-2908.

Kitano Kenji et al.: "Synthesis of novel 4'-C-methyl-pyrimidine nucleosides and their biological activities", Bioorganic & Medicinal Chemistry Letters , 9(6), 827-830, 1999.

Sugimoto Isamu et al.: "Nucloesides and nucleotides. 183. Synthesis of 4' alpha-branched thymidines as a new type of antiviral agent", Bioorganic & Medicinal Chemistry Letters, 1999, 9(3). 385-388.

Haraguchi K et al. Stereoselective Sytheis of 4'-C-Branched 2',3'-Didehydro2',3'-dideoxy Nucleosides Based on SncCl4-Promoted Allylic Rearrangement, Tetrahedron Letters 1992, 33:28411-2844.

Chen X, Zhou W, Schinazi RF, Chu CK. Synthesis of 3'Fluoro-2',3'-dideoxy-2',3'-didehydro-4'-ethynyl-D-  and  -L-furanosyl Nucleosides. J Org Chem, 2004;69:3034-6041.

\* cited by examiner

| X | Name |
|---|---|
| -H | D4T |
| -CH$_3$ | 4'-methyl D4T |
| -C=CH$_2$ | 4'-vinyl D4T |
| -C≡CH | 4'-ethynyl D4T |
| -C≡CCH$_3$ | 4'-ethynylmethyl D4T |
| -C≡CCl | 4'-ethynylchloro D4T |
| -CH$_2$CH=CH$_2$ | 4'-allyl D4T |
| -CN | 4'-cyano D4T |

L(-)Fd4C

L(-)SddC
(3TC)

ddC

D4T

Dinucleoside Prodrugs

AZT and TKD-4-114 Dinucleoside Phosphate        d4T and TKD-4-114 Dinucleoside Phosphate ddI and TKD-4-114 Dinucleoside Phosphate        ddC and TKD-4-114 Dinucleoside Phosphate Abacavir and TKD-4-114 Dinucleoside Phosphate        ddA and TKD-4-114 Dinucleoside Phosphate Scheme A Alternative Synthesis of TKD-4-114

Preparation of 4'-Benzoyloxy nucleosides
(an Alternative Method for the Introduction of an Acyloxy Group into the 4'-Position)

FIGURE 7A

Scheme 1. Synthesis of 4'-ethynyl-2'-deoxynucleosides from 2'-deoxynucleosides

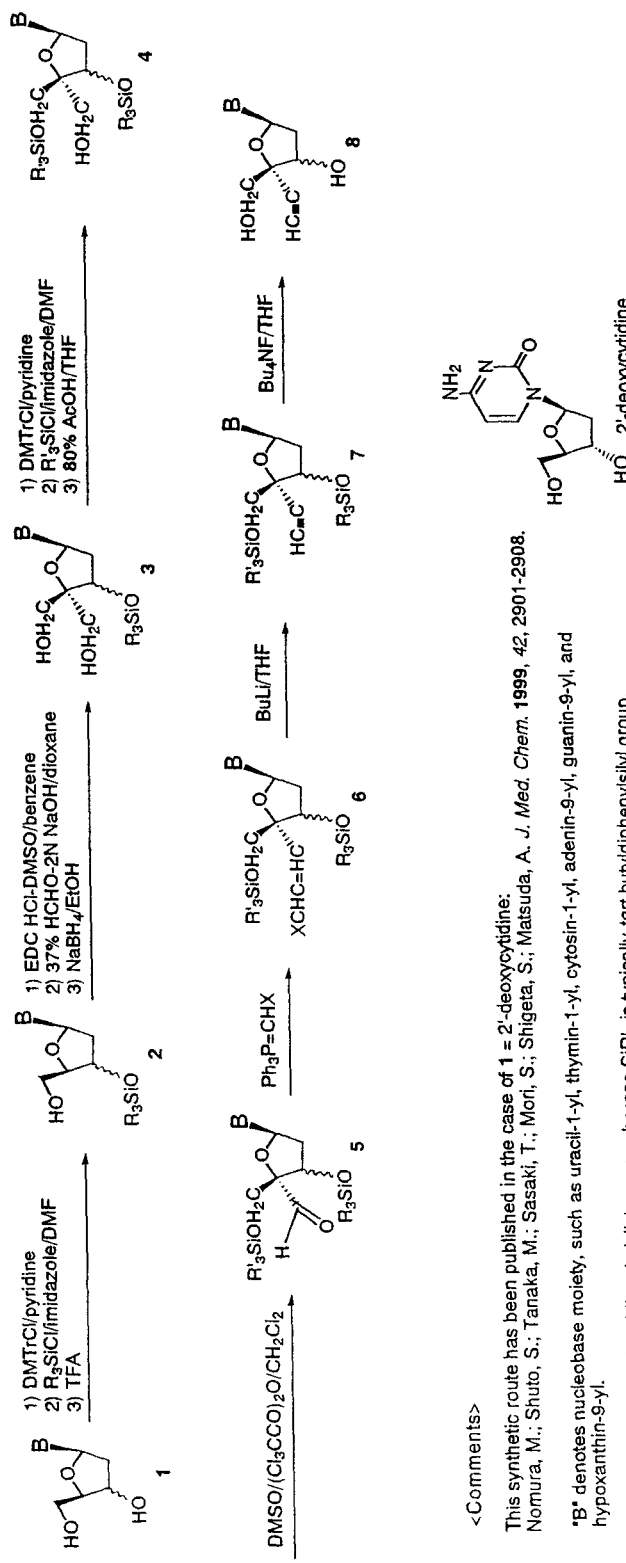

<Comments>

This synthetic route has been published in the case of 1 = 2'-deoxycytidine:
Nomura, M.; Shuto, S.; Tanaka, M.; Sasaki, T.; Mori, S.; Shigeta, S.; Matsuda, A. *J. Med. Chem.* 1999, 42, 2901-2908.

*B* denotes nucleobase moiety, such as uracil-1-yl, thymin-1-yl, cytosin-1-yl, adenin-9-yl, guanin-9-yl, and hypoxanthin-9-yl.

SiR₃ is typically *tert*-butyldimethylsilyl group, whereas SiR'₃ is typically *tert*-butyldiphenylsilyl group.

X is halogen atom, such as chlorine.

Scheme 2. Synthesis of 4'-ethynyl-2'-deoxynucleosides from sugar precursor

<Comments>

This synthetic route has been published in the synthesis of 18 where B is thymin-1-yl: Ohrui, H.; Kohgo, S.; kitano, K.; Sakata, K.; Kodama, E.; Yoshimura, K.; Matsuoka, m.; Shigeta, s.; Mitsuya, S. *J. Med. Chem.*, 2000, *43*, 4516-4525.

R$_3$Si is typically triethylsilyl group.

Scheme 3. Introduction of the 2',3'-double bond: synthesis of 2',3'-didehydro-3'-deoxy-4'-ethynylthymidine (4'-ethynyl-d4T, TKD-4-114)

<Comments>

This route has been used for the conversion of thymidine to d4T: Horwitz, J. P.; Chua, J.; Rooge, M. A. D.; Noel, M.; Klundt, I. *J. Org. Chem.* 1966, *31*, 205.

$R_3Si$ is typically *tert*-butyldimethylsilyl group.

ANTI-VIRAL NUCLEOSIDE ANALOGS AND METHODS FOR TREATING VIRAL INFECTIONS, ESPECIALLY HIV INFECTIONS

RELATED APPLICATIONS

This application claims the benefit of provisional application No. 60/448,554, filed Feb. 19, 2003, the entirety of which is incorporated by reference herein.

GOVERNMENT SUPPORT

This invention was made with government support under AI038204 awarded by the National Institutes of Health. The government has certain rights in the invention.

FIELD OF THE INVENTION

The present invention relates to novel 2',3'-dideoxy and didehydro nucleoside analogs and related prodrugs and their use in the treatment of a number of viral infections and disease states, especially including HIV and its related condition AIDS, among numerous others, and in particular, retroviruses.

BACKGROUND OF THE INVENTION

Human immunodeficiency virus (HIV/AIDS) has become the leading infectious cause of death worldwide surpassing malaria and tuberculosis. WHO AIDS Epidemic Update, data for December 2002, lists 3.1 million deaths and 42 million people currently living with AIDS. The need for new therapeutic agents with better efficacy is evident. Dideoxy nucleosides are an important group of antiviral compounds (16, 26, 27). A member of this group, 3'-Azido-3'-deoxythymidine (AZT, Retovir, Zidovudine) was the first drug approved for the treatment of HIV. Its dose limiting adverse effect is myelosuppression (14, 36, 39), which may be worsened by the concurrent administration of other drugs that cause bone marrow suppression or that are hepatically metabolized. 2',3'-Didehydro-3'-deoxythymidine (D4T, Stavudine, Zerit) was then approved because of better bioavailability and lower acute toxicity (1). D4T is limited by a long-term delayed toxicity, peripheral sensory neuropathy (4) which is related to mitochondrial damage (3, 5, 6, 13, 18, 22, 30, 33, 34). 2',3'-Dideoxyinosine (ddI, Didanosine, Videx) and 2',3'-dideoxycytidine (ddC, Zalcitabine) are dideoxynucleoside anti HIV compounds that also have peripheral neuropathy as their leading adverse effect. In the search to find anti-HIV nucleoside analogs that had less neuropathy, many classes of compounds were synthesized and assessed for their antiviral activity and cytotoxicity including their impact on mitochondrial DNA. Dideoxynucleosides in the unnatural L conformation represented by β-L-2',3'-dideoxy-3'-thiacytidine (3TC, Lamivudine), its 5-fluoro analog (FTC, Emtricitabine) and β-L-2',3'-dideoxy-2',3'-didehydro-5-fluorocytidine (LFd4C, Elvucitabine), have been shown by us (2, 11, 12, 23-25) and others (8, 9, 15, 37) to have good antiviral activity and low mitochondrial toxicity. However, even with compounds relatively non-toxic to mitochondria there is a lack of a durable response. This condition can be caused by either the rapid emergence of resistant virus or by host changes that cause differences in drug metabolism (10, 19, 35).

One approach to combat this problem is to develop compounds with less toxicity and lack of cross-resistance to other antiviral drugs. When used in combinations these compounds may decrease the dosage of existing drugs needed to achieve the same antiviral effect with less toxicity. Furthermore, these compounds could even delay the onset of resistance, which could be based on the decreased viral load during treatment. In the search for a new antiviral compounds, others have looked at 4'-substituted dThd analogs (29) (32), while we synthesized a series of 4'-substituted D4T analogs. Screening revealed the 4'-ethynyl D4T to be the most active among those tested (17). In the studies described within we describe the structure activity relationship of this class of compounds and characterize 4'-ethynyl D4T in more detail with respect to its mode of action against HIV and its interaction with key cellular enzymes that mediate its activity.

OBJECTS OF THE INVENTION

It is an object of the invention to provide compounds for the treatment of viral infections or cancer.

It is another object of the invention to provide pharmaceutical compositions which can be used to treat viral infections or cancer.

It is an additional object to provide compounds and pharmaceutical compositions which can be used in combination therapy with known anti-viral agents.

It is still a further object of the present invention to provide prodrug forms of compounds according to the present invention which are formulated in combination with other antiviral agents.

It is another object of the invention to provide therapeutic methods for the treatment of a variety of viruses as otherwise described herein, or cancer.

It is yet another object of the invention to provide methods of synthesizing compounds according to the present invention.

These and/or other objects of the invention may be readily gleaned from the description of the invention which follows.

BRIEF DESCRIPTION OF THE FIGURES

FIG. 7A shows the synthesis of 4'-ethynyl-2'-deoxynucleosides from 2'-deoxynucleosides according to the methodology of Nomura, et al. *J. Med. Chem.*, 42, 2901-2908 (1999). Note that $SiR_3$ is a tert-butyldimethylsilyl group and $SiR'_3$ is a tert-butyldiphenylsilyl group. X is a halogen atom, such as chlorine and B is a nucleoside base such as uracil, adenine, guanine or cytosine, among others.

SUMMARY OF THE INVENTION

Figure 1:
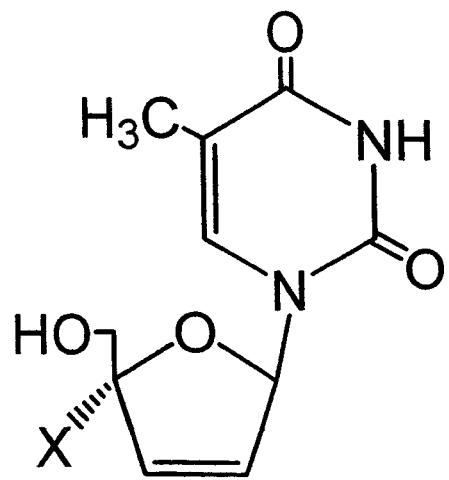
FIG. 1 depicts a number of preferred compounds according to the present invention.
Figure 2:
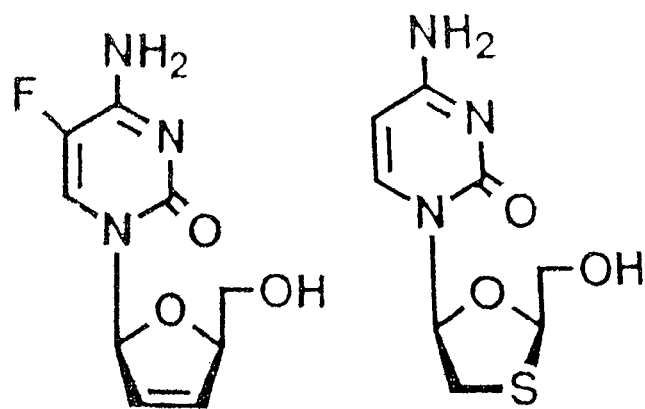
FIG. 2 depicts anti-HIV compounds L(−)Fd4C, L(−)SddC, ddC and D4T.
Figure 2:
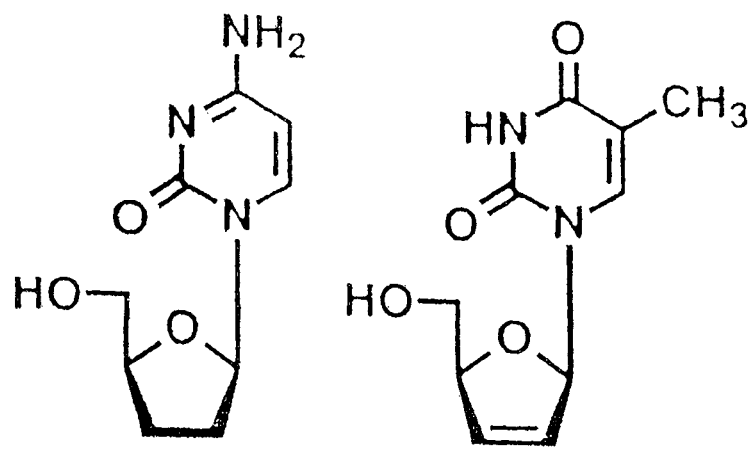

The present invention relates to novel compounds according to the general formulas I, II, III, IV or V:

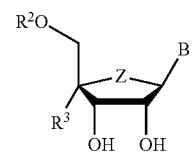
I

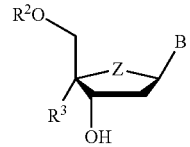
II

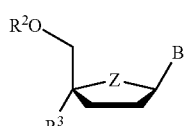
III

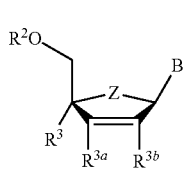
IV

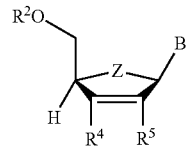
V wherein B is nucleoside base according to the structure:

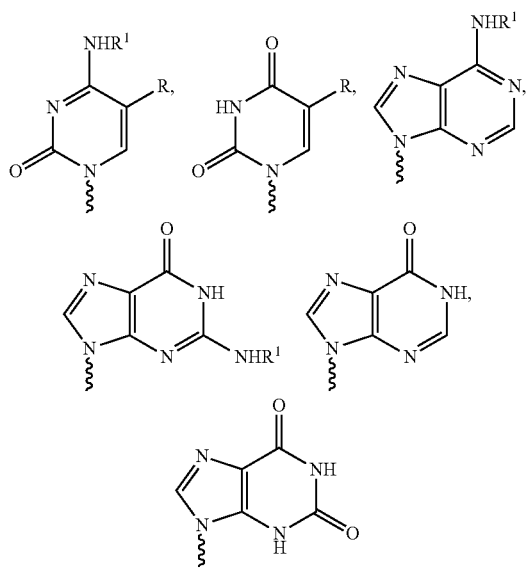

R is H, F, Cl, Br, I, $C_1$-$C_4$ alkyl (preferably $CH_3$), —C≡N, —C≡C—$R_a$,

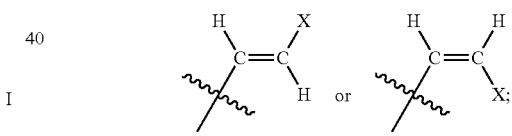

X is H, $C_1$-$C_4$ alkyl (preferably, $CH_3$), F, Cl, Br or I;

Z is O or $CH_2$, with the proviso that Z is $CH_2$ and not O when the compound is according to general formula II, $R^3$ is —C≡C—H and $R^2$ is H or a phosphate, diphosphate, triphosphate or phosphotriester group;

$R^1$ is H, an acyl group, a $C_1$-$C_{20}$ alkyl or an ether group;

$R^2$ is H, an acyl group, a $C_1$-$C_{20}$ alkyl or ether group, a phosphate, diphosphate, triphosphate, phosphodiester group or a

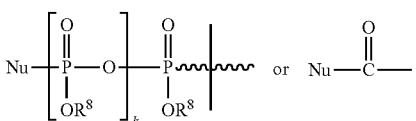

Nu is a radical of a biologically active antiviral compound such that an amino group or hydroxyl group from said biologically active antiviral compound forms a phosphate, phosphoramidate, carbonate or urethane group with the adjacent moiety;

$R^8$ is H, or a $C_1$-$C_{20}$ alkyl or ether group, preferably a $C_1$-$C_{12}$ alkyl group;

k is 0-12, preferably, 0-2;

$R^3$ is selected from a $C_1$-$C_4$ alkyl (preferably, $CH_3$), —$(CH_2)_n$—C≡C—$R_a$,

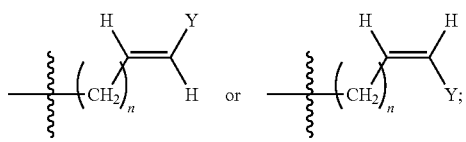

$R^{3a}$ and $R^{3b}$ are independently selected from H, F, Cl, Br or I; $R^4$ and $R^5$ are independently selected from H, F, Cl, Br, I, OH, $C_1$-$C_4$ alkyl (preferably, $CH_3$), —$(CH_2)_n$—C≡C—$R_a$,

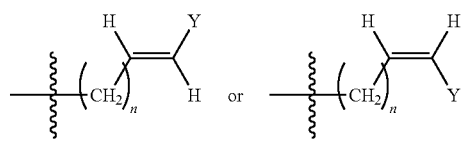

with the proviso that $R^4$ and $R^5$ are not both H;

$R_a$ is H, F, Cl, Br, I, or —$C_1$-$C_4$ alkyl, preferably H or $CH_3$;

Y is H, F, Cl, Br, I or —$C_1$-$C_4$ alkyl, preferably H or $CH_3$; and n is 0, 1, 2, 3, 4 or 5, preferably 0, 1 or 2;

and their anomers, pharmaceutically acceptable salts, solvates, or polymorphs thereof.

Preferably, B is a thymine base (i.e., a uracil base with 5-methyl substitution) or an unsubstituted adenine base. $R^1$ and $R^2$ are preferably H. $R^3$ is preferably $CH_3$, —C≡CH or —$(CH_2)_n$—CH=$CH_2$, where n is 1.

In other preferred aspects of the present invention, the biologically active antiviral agent is a nucleoside compound selected from ddC, ddI, ddA, B-LFd4C, B-LFddC, AZT, abacavir, 3TC, D4T and FTC, wherein the biological active agent is attached to a phosphate, phosphoramidate, carbonate or urethane moiety through a hydroxyl group at the 5' position of the sugar synthon of the nucleoside.

In another embodiment according to the present invention, pharmaceutical compositions comprise an effective amount of one or more compounds as described above, optionally in combination with a pharmaceutically acceptable carrier, excipient or additive.

Methods of treatment of viral infections, and/or preventing or delaying the onset of conditions related to viral infections is a further aspect of the invention. The compounds may be used to treat infections or conditions associated with viruses, including, for example, human immunodeficiency viruses 1 and 2 (HIV-1 and HIV-2) including drug resistant strains, human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses. Preferably, compounds according to the present invention may be used to treat HIV infections. In addition, the present compounds may be used to prevent and/or reduce the likelihood of a virus infection such as an HIV infection or a condition which may occur secondary to a viral infection, such as AIDS, EBV-related lymphoma or HHV-8 associated cancer (sarcoma) will actually occur.

DETAILED DESCRIPTION OF THE INVENTION

The term "compound", as used herein, unless otherwise indicated, refers to any specific chemical compound disclosed herein. Within its use in context, the term generally refers to a single compound preferably, β anomers, but in certain instances may also refer to stereoisomers and/or optical isomers (including racemic mixtures), preferably well as specific enantiomers, in particular, β-D or β-L, preferably β-D nucleoside analogs or enantiomerically enriched mixtures of disclosed compounds. In the present invention in certain instances, especially in the dual antagonist/dinucleoside prodrug aspect of the present invention, a compound according to the present invention is chemically linked through a phosphate (including polyphosphate), phosphoramidate, carbonate or urethane moiety to a biologically active antiviral agent through an amine or hydroxyl group of the biologically active antiviral agent.

Figure 3:
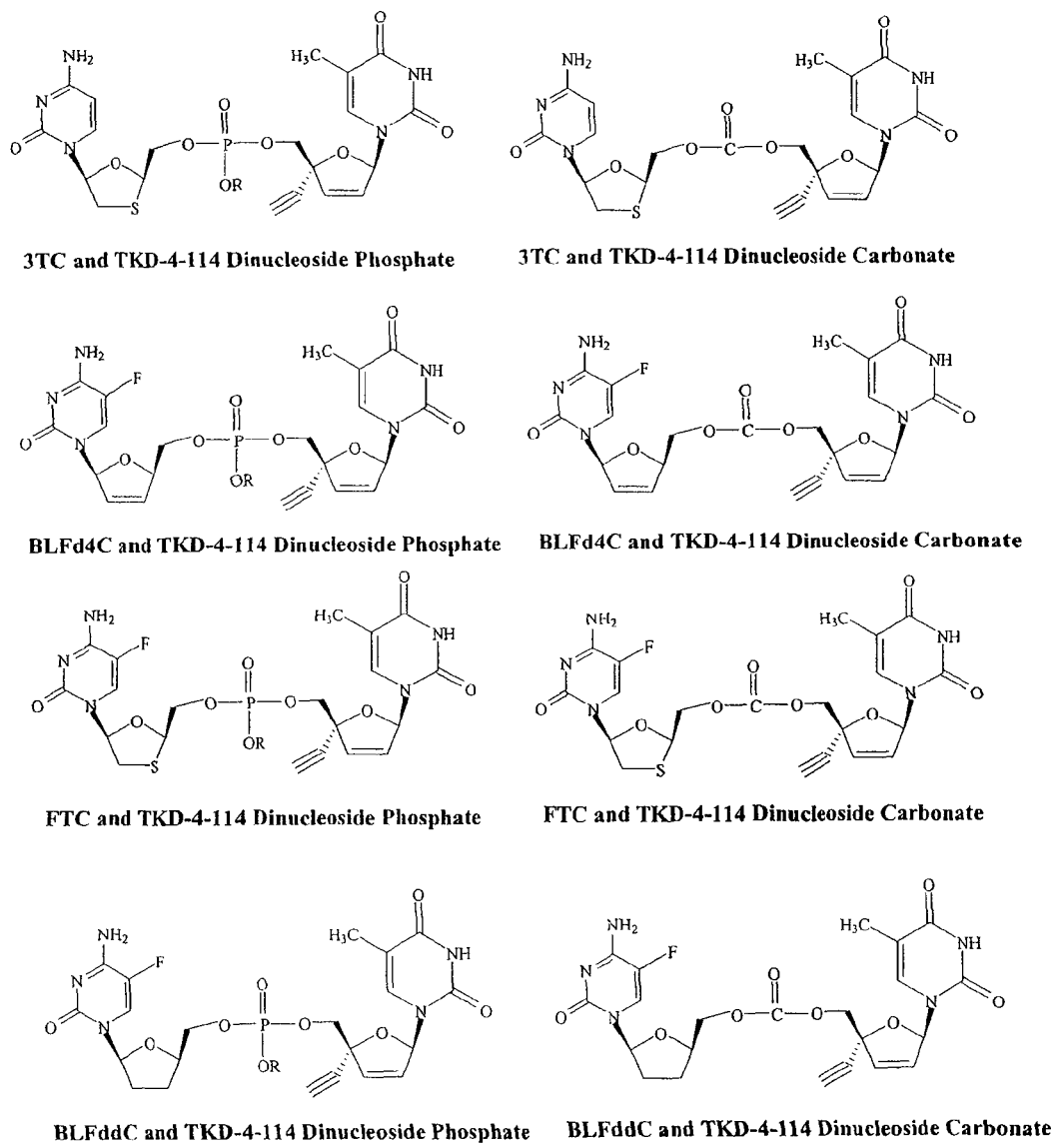
FIG. 3 depicts preferred dinucleoside compounds according to the present invention.
Figure 3:
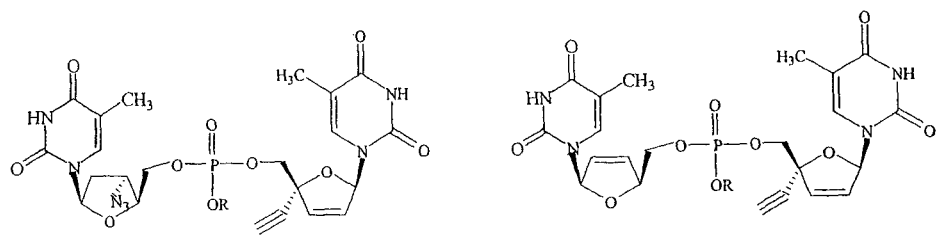
Figure 3:
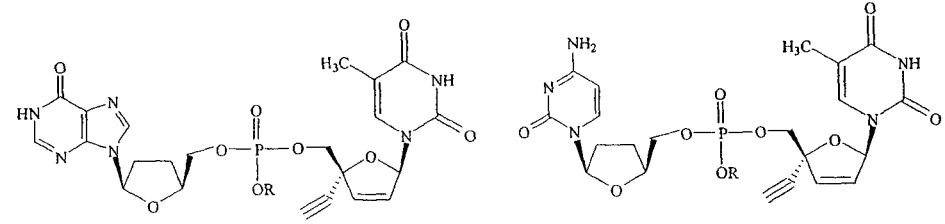
Figure 3:
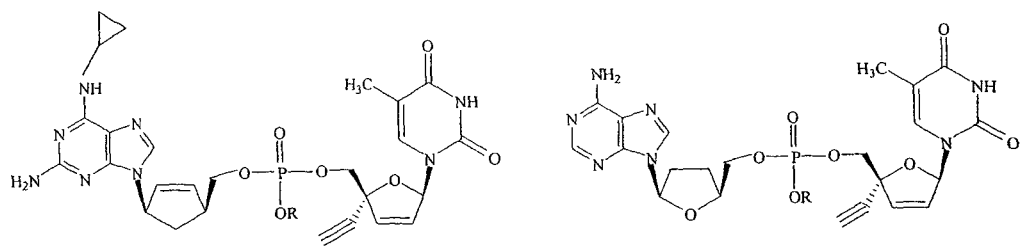

The term "dual antagonist" (within context, "dinucleoside") refers to a prodrug compound comprising two active agents, one being an active nucleoside compound according to the present invention and the other being a known active agent, preferably a known anti-viral agent, more preferably an anti-HIV agent having a free amino group or hydroxyl group which can be used to link the agent to a compound according to the present invention through a phosphate or carbonate group. In this dual antagonist aspect of the invention, a biologically active agent having a free hydroxyl or amino group may be used to link a compound according to the present invention through a phosphate or carbonate moiety to produce prodrug compounds which exhibit biological activity, preferably antiviral activity. In this aspect, a nucleoside analog according to the present invention is linked to the bioactive agent, preferably through a primary alcohol at the 5' OH position of the sugar synthon to produce a phosphate, phosphoramidate, carbonate or urethane moiety. Alternatively, a secondary alcohol or a free amine group from the present nucleoside compounds may be used to form the linker with the other bioactive agent in this dual antagonist aspect of the present invention. Preferably, β-D or β-L nucleoside analogs may be used as the bioactive agent and linked to nucleoside compounds of the present invention (which themselves may be enantiomerically enriched β-D or β-L nucleoside compounds, racemates or diastereomeric mixtures) to form dinucleoside prodrugs, depending upon the activity of the nucleoside compound chosen for use. In preferred aspects of the invention, the biologically active antiviral agent is preferably another anti-viral nucleoside agent such as ddC, abacavir, ddI, ddA, 3TC, AZT, D4T, FTC, FddC and Fd4C. Preferred dinucleoside compounds are set forth in attached FIG. 3.

Exemplary bioactive agents, especially anti-HIV agents, which may be used in this dual antagonist aspect of the present invention include, for example (compound name and active moiety through which linking with nucleoside compound according to the present invention occurs):

Atazanavir (BMS-232632) using the free secondary hydroxyl group;

Bis(POM)-PMEA (Adefovir dipivoxyl) using the free amine group;

Bis(POC)-PMPA (Tenofovir disoproxil) using the free amine group;

Etecavir using the primary hydroxyl group on the carbocyclic sugar synthon;
Indinavir (Crixivan, MK-639 L-735,524 from Merck) using the free secondary hydroxyl group;
KHI-227 (Kynostatin of Nikko Kyodo Co.) using the free secondary hydroxyl group:
2-[3-[3-(S)-[[(Tetrahydrofuranyloxy)carbonyl]amino]-4-phenyl-2(R)-hydroxybutyl]]-N-(1,1-dimethylethyl) decahydro-3-isoquinolinecarboxamide (IsoquinCON furanyl urethane analog from Merck) using the free secondary hydroxyl group;
Carbamic acid, [3-{[(4-methoxyphenyl)sulfonyl](cyclopenylmethyl)amino]-2-hydroxy-1-(phenylmhnethyl) propyl]-, tetrahydrofuranyl ester (VB-11,328 of Vertex) using the free secondary hydroxyl group;
KNI-174 from Nikko Kyodo Co. using the free secondary hydroxyl (or free amine) group;
Val-Val-Sta from Sandoz (Austria) using the free secondary hydroxyl group;
CPG53820 from Ciba-Geigy using the free secondary hydroxyl group;
bis-Val HOEt-N2 aza-peptide isostere using the free secondary hydroxyl group;
C2-Sym Phosphinic amide derivative from Hoechst AG using the free amine group;
2,5,-Diamino-N,N'-bis(N-benzyloxycarbonyluelyl)-1,6-diphenyl-3(S),4(S)-hexanediol BzOCValPhe[diCHOH (SS]PheValBzOC from Abbott using the free secondary hydroxyl group;
2,5,-Diamino-N,N'-bis(N-benzyloxycarbonyluelyl)-1,6-diphenyl-3(R),4(R)-hexanediol BzOCValPhe[diCHOH (RR]PheValBzOC from Abbott using the free secondary hydroxyl group;
bis(S-acetyl-2-thioethyl)phosphotriester of ddA or [bis (SATE)ddAMP] using the free amine;
BILA 2186 BS (Bio-Mega/Boehringer Ingelheim) using the free secondary hydroxyl group;
Agenerase (Amprenavir; VX-478; 141W94) of Vertex/Kissei/Glaxo Welcome at the free secondary hydroxyl or amine group;
A-98881 (Azacyclic urea derivative) of Abbott using the free secondary hydroxyl group or phenolic hydroxyl group;
A-83962 (Rifonavir derivative) of Abbott using the free secondary hydroxyl group;
A-80987 (Rifonavir derivative) of Abbott using the free secondary hydroxyl group;
(2-Naphthalcarbonyl)Asn[decarbonylPhe-hydroxyethyl] ProOtertButyl or 2NaphCOAsnPhe[CHOHCH2]Pro-OtBu of Roche using the free secondary hydroxyl;
2-Aminobenzylstatine Valyl Cbz derivative of Sandoz using the free secondary hydroxyl or amine;
2-Aminobenzylstatine Valyl Cbz derivative of Sandoz using the free hydroxyl;
10H-2(Cbz-ValNH)3PhPr [14]paracyclophane derivative of Sandoz using the free secondary hydroxyl;
10H-2(Cbz-ValNH)3PhPr [13]paracyclophane derivative of Sandoz using the free secondary hydroxyl;
10H-2(Cbz-ValNH)3PhPr [13]metacyclophane derivative of Sandoz using the free secondary hydroxyl;
H-2(Cbz-Tle)3PhPr [14]paracyclophane derivative of Sandoz using the free secondary hydroxyl;
1-(20HPr)-4-substituted-piperazine (cyclopropyl), thieneyl carbamate deriv. (from Merck) using the free secondary hydroxyl group;
1-(20HPr)-4-substituted-piperazine (cyclobutyl), thienyl carbamate derive. (from Merck) using the free secondary hydroxyl group;
1-(20HPr)-4-substituted-piperazine (3-pentyl), thienyl carbamate derive. (from Merck) using the free secondary hydroxyl group;
10H-2(Cbz-ValNH)3PhPr[17]paracyclophane derivative (from Sandoz) using the free second hydroxyl group;
A-81525 (from Abbott) using the free secondary hydroxyl group;
XM323 (DMP-323 from DuPont Merck) using the free primary or secondary hydroxyl groups;
Tipranavir (U-140690 or PHU-140690 from Pharmacia & Upjohn) using the phenolic hydroxyl group;
ThienopyridCON thienyl urethane derivatives (HOCH2CH2 isostere from Lilly) (the benzyl substituted derivative or the methyl mercaptophenyl substituted derivatives) using the free secondary hydroxyl groups;
SDZ PRI 053 (Sandoz) using the free secondary hydroxyl group;
SD146 (DuPont Merck) using either of the free secondary hydroxyl groups;
Telinavir (SC-52151 from Searle/Monsanto) using the free secondary hydroxyl group or amine;
(R)2QuinCOAsnPhe[CHOHCH2]PipCONHtBu (from Roche) using the free secondary hydroxyl group or amine;
Saquinavir (Invirase or RO 31-8959 from Roche) using the free secondary hydroxyl group or amine;
Saquinavir/Melfinavir derivative (from Lilly) using the free secondary hydroxyl group;
IsoquinCON Thf-Thf Urethane Analog (from Merck) using the free secondary hydroxyl group;
IsoquinCON thienyl urethane analog (from Merck) using the free secondary hydroxyl group;
R-87366 (AHPBA analog from Sankyo) using the free amine group;
DMP 460 (Dupont Merck/Avid) using the free secondary hydroxyl groups or either of the aniline amine groups;
L685,434 (Merck) using the free secondary hydroxyl group;
L685,434-6-Hydroxyl derivative (Merck) using the free secondary hydroxyl group;
L685,434-OEtNMe2 (Merck) using the free secondary hydroxyl group;
L685,434-OPrMorph derivative (Merck) using the free secondary hydroxyl group;
L689,502 (Merck) using the free secondary hydroxyl group;
Lasinavir (CGP 61755 from CIBA/Novartis) using the free secondary hydroxyl group;
Aluviran (Lopinavir, ABT-378, RS-346 A157378 of Abbott) using the free secondary hydroxyl group;
Nelfmavir-octahydro-thienopyridine analog (from Lilly) using the free secondary hydroxyl group;
P9941 (from DuPot Merck) using either of the free secondary hydroxyl groups;
Palinavir (BILA 2011 BS from BIO-MEGA/Boehringer Ingelheim) using the free secondary hydroxyl group;
Penicillin, 2Isoquin-OHPrNH2 analog (from Glaxo Welcome) using the free secondary hydroxyl group, among numerous others.

The above active compounds, and other relevant bioactive agents for use in the dual antagonist aspect of the present invention may be found at the NIH website at http://www.ni-aid.nih.gov/daids/dtpdb/, relevant portions of which are incorporated by reference herein. Although not necessary or critical, it is preferred in the dual antagonist aspect of the present invention that the two active agents which form the dual antagonist have different mechanisms of action such as reverse transcriptase inhibition, protease inhibition, zinc finger inhibition, TAT inhibition, integrase inhibition or other inhibitory activity. Noted here is the fact that each of the above-described agents, without limitation, may be co-administered with any one or more of the compounds according to the present invention without being chemically linked.

The term "effective" is used herein, unless otherwise indicated, to describe an amount of a compound which, in context, is used to produce or effect an intended result, whether that result relates to the treatment of a viral disease state, disorder or condition associated with a viral disease or alternatively, is used to produce another compound, agent or composition. This term subsumes all other effective amount or effective concentration terms which are otherwise described in the present application.

The term "patient" is used throughout the specification to describe an animal, generally a mammal and preferably a human, to whom treatment, including prophylactic treatment, with the compositions according to the present invention is provided. For treatment of those infections, conditions or disease states which are specific for a specific animal such as a human patient, the term patient refers to that specific animal.

The term "virus" shall be used to describe all types of viruses, the growth or replication of which may be inhibited or disease states of which may be treated using one or more methods according to the present invention. Viruses which may be treated according to the present invention include, for example, human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, among numerous others.

The term "human immunodeficiency virus" shall be used to describe human immunodeficiency virus (HIV) and its infections, which term shall be used to embrace both human immunodeficieny virus 1 (HIV-1) and human immunodeficiency virus 2 (HIV-2).

The term "human T-cell leukemia virus" shall be used to describe human T-cell leukemia virus and its infections, which term shall be used to embrace both human T-cell leukemia virus 1 (HTLV-1) and human T-cell leukemia virus 2 (HTLV-2).

The term "Hepatitis B Virus (HBV)" is used to describe the virus (serum hepatitis virus) which produces viral heptatis type B in humans. This is a viral disease with a long incubation period (about 50 to 160 days) in contrast to Hepatitis A virus (infectious hepatitis virus) which has a short incubation period. The virus is usually transmitted by injection of infected blood or blood derivatives or merely by use of contaminated needles, lancets or other instruments. Clinically and pathologically, the disease is similar to viral hepatitis type A; however, there is no cross-protective immunity. Viral antigen (HBAg) is found in the serum after infection.

The term "Herpes Simplex Virus" (HSV) is used throughout the specification to describe HSV1 and HSV 2 which are the causative viral agents of Herpes infections, including genital Herpes infections.

The term "Hepatitis C Virus (HCV)" is used throughout the specification to describe the hepatitis virus which is the causative agent of non-A, non-B hepatitis. The disease in the acute stage is, in general, milder than hepatitis B, but a greater proportion of such infections become chronic.

The term "Epstein-Barr virus (EBV)" is used throughout the specification to describe a herpetovirus found in cell cultures of Burkitts lymphoma. EBV is the causative agent in infectious mononucleosis, as well as in a number of other related conditions/disease states, including EBV-associated lymphomas.

The term "Varicella-Zoster virus (VZV)" is used to describe Herpes virus varicellae, also known as chicken pox or herpes zoster. Varicella results from a primary infection with the virus; herpes zoster results from secondary invasion by the same or by reactivation of infection which in many instances may have been latent for a number of years. Both the primary and secondary infections of VZV may be treated using compositions according to the present invention.

The term "respiratory syncytial virus (RSV)" is used throughout the specification to describe an RNA-containing virus of the genus Pneumovirus that causes minor respiratory infection with rhinitis and cough in adults, but is capable of causing bronchitis and bronchopneumonia in young children. The virus is named for the tendency to form syncytia in tissue culture.

The term "adenovirus" is used throughout the specification to describe a virus of the family adenoviridae which are double-stranded DNA-containing viruses, which infect mammals and birds. The virion is 70 to 90 nm in diameter and is naked (has no envelope). The virus develops in nuclei of infected cells; isolation requires tissue cultures since laboratory animals are not susceptible to apparent infection. The family includes two genera, *Mastadenovirus* and *Acviadenovirus*.

The term "Human Herpes Virus 8 (HHV-8)" is used throughout the specification to describe a herpetovirus which is believed to be the causative agent of Kaposis sarcoma in AIDS patients.

The term "Human Papilloma Virus (HPV)" is used throughout the specification to describe a virus which causes genital warts. Also known as infectious warts virus, HPV is a universal, common, often recurrent viral infection with a large number of serotypes. HPV infection can lead to the formation of genital warts which can, in turn, lead to genital and/or cervical cancer. Genital warts caused by HPV types 1, 2, 6, 11, 16 and 18 are generally transmitted sexually and are often associated with cervical and/or genital cancer. HPV may mature to produce a papillary tumor or wart, which is a circumscribed benign epithelial tumor projecting from the surrounding surface. It is generally a benign epithelial neoplasm consisting of villous or arborescent outgrowths of fibrovascular stroma covered by neoplastic cells.

The term "*flavivirus*" is used throughout the specification to describe viruses belonging to the genus *Flavivirus* of the family Togaviridae. According to virus taxonomy, about 50 viruses including Hepatitis C virus (HCV), Yellow Fever virus, Dengue Virus, Japanese Encephalitis virus, West Nile virus and related flaviviruses are members of this genus. The viruses belonging to the genus *Flavivirus* are simply called flaviviruses. These viruses were formerly classified as group B arboviruses. The flaviviruses are agents of infectious disease and predominate in East, Southeast and South Asia and Africa, although they may be found in other parts of the world as well.

The term "Yellow Fever virus" is used to describe the *flavivirus* which is the causative agent of yellow fever. Yellow fever is a tropical mosquito-borne viral hepatitis, due to Yellow Fever virus (YFV), with an urban form transmitted by *Aedes aegypti*, and a rural, jungle or sylvatic form from tree-dwelling mammals by various mosquitos of the *Haemagogus* species complex. Yellow fever is characterized clinically by fever, slow pulse, albuminuria, jaundice, congesion of the face and hemorrhages, especially hematemesis (black vomit). It is fatal in about 5-10% of the cases.

The term "Dengue virus" is used throughout the specification to describe the *flavivirus* which is the causative agent(s) of dengue fever/dengue hemorrhagic fever. Dengue is a disease of tropical and subtropical regions occurring epidemically and caused by Dengue virus, one of a group of arboviruses which causes the hemorrhagic fever syndrome. Four grades of severity are recognized: grade I: fever and constitutional symptoms, grade II: grade I plus spontaneous bleeding (of skin, gums or gastrointestinal tract), grade III: grade II plus agitation and circulatory failure and grade IV: profound shock. The disease is transmitted by a mosquito of the genus *Aedes* (generally *A. aegyptiI*, but frequently, *A. albopictus*). Also called Aden, bouquet, breakbone, dandy, date, dengue (hemorrhagic) or polka, solar fever, stiffneck fever, scarlatina rheumatica or exanthesis arthorosia. Hemorrhagic dengue is a more pathogenic epidemic form of dengue which has erupted in a number of epidemic outbreaks in the Pacific region in recent years.

The term "pharmaceutically acceptable salt" is used throughout the specification to describe a salt form of one or more of the compositions (and in particularly preferred aspects according to the present invention, phosphate salts) herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of neoplasia, including cancer, the term "salt" shall mean a pharmaceutically acceptable salt, consistent with the use of the compounds as pharmaceutical agents.

The term "pharmaceutically acceptable derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "alkyl" shall mean within its context a $C_1$-$C_{20}$, preferably a $C_1$-$C_{10}$ linear, branch-chained or cyclic fully saturated hydrocarbon radical. The term "ether" shall mean a $C_1$ to $C_{20}$ ether group, formed from an oxygen and an alkyl group at a position on the sugar moiety of compounds according to the present invention, or alternatively, may also contain at least one oxygen group within the alkyl chain.

The term "acyl" is used throughout the specification to describe a group at the 5' position of the nucleoside analog (i.e., at the free hydroxyl position in the sugar synthon) which contains a $C_1$ to $C_{20}$ linear, branched or cyclic alkyl chain. The acyl group at the 5' position, in combination with the 5' hydroxyl group results in an ester, which, after administration, may be cleaved to produce the free nucleoside form of the present invention. Acyl groups according to the present invention are represented by the structure:

where $R_4$ is a $C_1$ to $C_{20}$ linear, branched or cyclic alkyl group, alkoxyalkyl, aryloxyalkyl, such as phenoxymethyl, aryl, alkoxy, among others. Preferred acyl groups are those where $R_4$ is a $C_1$ to $C_{10}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others including mesylate groups. One of ordinary skill in the art will recognize the acyl groups which will have utility in the present invention, either to synthesize the target pharmaceutical compounds or as prodrug forms of the nucleosides according to the present invention.

The term "phosphate ester" or "phosphodiester" is used throughout the specification to describe mono-phosphate groups at the 5' position of the dioxanyl moiety or sugar synthon which are diesterified such that the phosphate group is rendered neutral, i.e., has a neutral charge. Phosphate esters for use in the present invention include those represented by the structures:

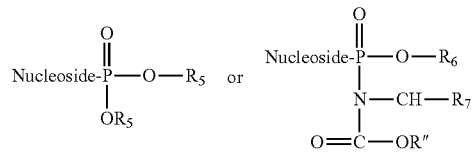

where $R_5$, $R_6$ and R" are selected from a $C_1$ to $C_{20}$ linear, branched or cyclic alkyl group, alkoxyalkyl, aryloxyalkyl, such as phenoxymethyl, aryl and alkoxy, among others, and $R_7$ is a $C_1$ to $C_{20}$ linear, branched or cyclic alkyl or acyl group, alkoxyalkyl, aryloxyalkyl, such as phenoxymethyl, aryl and alkoxy, among others. Preferred monophosphate esters for use in prodrug forms according to the present invention are those where $R_5$ is a $C_1$ to $C_{20}$ is a linear or branched chain alkyl group, more preferably a $C_1$ to $C_3$ alkyl group.

The term "protecting group" or "blocking group" shall mean, within its context, a chemical group or moiety which is used to prevent an otherwise active moiety such as an amine, hydroxyl or mercapto group from reacting in a given reaction scheme and which is readily removed under mild conditions which do not otherwise undesirably affect the molecule or compound to which the protecting group is bonded. In the present invention, numerous protecting groups may be used to produce compounds according to the present invention, preferred groups include the benzoate group to protect or block a primary or secondary hydroxyl group and silyl groups (in particular, a tertiary butyl dimethyl silyl, a tertiary butyl diphenyl silyl group or a trimethylsilyl group or a related silyl protecting group) to block primary (or secondary) hydroxyl groups. One of ordinary skill in the art will recognize the various protecting groups which may be utilized within context in producing compounds and intermediates according to the present invention.

The term "inhibitory effective concentration" or "inhibitory effective amount" is used throughout the specification to describe concentrations or amounts of compounds according to the present invention which substantially or significantly inhibit the growth or replication of susceptible viruses, especially including human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, among numerous others.

The term "preventing effective amount" is used throughout the specification to describe concentrations or amounts of compounds according to the present invention which are prophylactically effective in preventing, reducing the likelihood of infection or delaying the onset of infections in patients caused by human immunodeficiency viruses 1 and 2 (HIV-1 and HIV-2), human T-cell leukemia viruses 1 and 2 (HTLV-1 and HTLV-2), respiratory syncytial virus (RSV), human papilloma virus (HPV), adenovirus, hepatitis B virus (HBV), hepatitis C virus (HCV), Epstein-Barr virus (EBV), varicella zoster virus (VZV), cytomegalovirus (CMV), herpes simplex viruses 1 and 2 (HSV-1 and HSV-2), human herpes virus 8 (HHV-8, also known as Kaposi's sarcoma-associated virus) and flaviviruses, including Yellow Fever virus, Dengue virus, Japanese Encephalitis and West Nile viruses, among numerous others.

The term "coadministration" or "combination therapy" is used to describe a therapy in which at least two active compounds in effective amounts are used to treat a viral infection at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more anti-viral agent, including anti-HIV agents such as nucleoside reverse transcriptase inhibitors (NRTI), non-nucleoeoside reverse transcriptase inhibitors, protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development. Coadministration also embraces the administration of dinucleoside analogs (i.e., compounds wherein at least two biologically active nucleosides are chemically linked via a chemical linker such as, for example, without limitation, phosphate groups or carboxylate groups, among others) or other dual antagonists, where at least one of the active nucleoside compounds of the dinucleoside compound is a compound as otherwise described herein.

Compounds according to the present invention may be used in pharmaceutical compositions having biological/pharmacological activity for the treatment of, for example, viral infections, as well as a number of other conditions and/or disease states which may appear or occur secondary to the viral infection. These compositions comprise an effective amount of any one or more of the compounds disclosed hereinabove, optionally in combination with a pharmaceutically acceptable additive, carrier or excipient. Compounds according to the present invention may also be used as intermediates in the synthesis of compounds exhibiting biological activity as well as standards for determining the biological activity of the present compounds as well as other biologically active compounds.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of novel nucleoside of the instant invention that may be combined with the carrier materials to produce a single dosage form will vary depending upon the host treated, the particular mode of administration. Preferably, the compositions should be formulated so that a dosage of between about 0.01 and 150, preferably about 0.5 to about 25 mg/kg of patient/day of the novel nucleoside can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In particularly preferred embodiments according to the present invention, the compounds and compositions are used to treat, prevent or delay the onset of viral infections of mammals and in particular HIV, HBV, HSV1 and/or II, EBV, HHV-8 and *flavivirus* infections, among others. In its preferred embodiments, the compounds are used to treat HIV, HSV I and/or II, HBV, EBV or HHV-8 infections, especially HIV infections in humans. Preferably, to treat, prevent or delay the onset of a viral infection, the compositions will be administered in oral dosage form in amounts ranging from about 250 micrograms up to about 500 mg or more at least once a day, preferably, up to four times a day, within the dosage range used for therapeutic treatment. The present compounds are preferably administered orally, but may be administered parenterally, topically, in suppository or other form.

The compounds according to the present invention, because of their low toxicity to host cells, may advantageously be employed prophylactically to prevent a viral infection or to prevent the occurrence of clinical symptoms associated with the viral infection, for example AIDS secondary to HIV, lymphoma secondary to EBV or Kaposi's sarcoma secondary to HHV-8. Thus, the present invention also encompasses methods for the prophylactic treatment (preventing, reducing the likelihood or delaying the onset) of viral infections, and in particular HIV and EBV and in particular, conditions which occur secondary to those viruses. In this aspect according to the present invention, the present compositions are used to prevent reduce the likelihood of or delay the onset of a viral infection, in particular, HIV, HSV, EBV or another virus infection or a virus related disease or condition such as AIDS or EBV-related lymphoma or Kaposi's sarcoma (HHV-8). This prophylactic method comprises administering to a patient in need of such treatment or who is at risk for the development of an HIV, EBV, HHV-8 or other viral infection, an amount of a compound according to the present invention effective for alleviating, preventing or delaying the onset of the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of compounds of the present invention for the prophylactic treatment of viral infections, these compounds may be administered within the same dosage range for therapeutic treatment (as described hereinabove, as a prophylactic agent to prevent the proliferation of the viral infection or alternatively, to prolong the onset of or reduce the likelihood of a patient contracting a virus infection which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

As indicated, compounds according to the present invention may be administered alone or in combination with other anti-viral agents for the treatment of a virus infection as otherwise described herein, especially including other compounds of the present invention or compounds which are otherwise disclosed as being useful for the treatment of HIV or flaviviruses, including those presently used to treat HIV such as nucleoside reverse transcriptase inhibitors (NRTI), non-nucloeoside reverse transcriptase inhibitors, protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-D4FC, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development, among others as well as compounds which are disclosed in inter alia, U.S. Pat. Nos. 6,240,690; 6,316,505; 6,316,492; 6,232,120; 6,180,604; 6,114,327; 5,891,874; 5,821,242; 5,532,215; 5,491,135; 5,179,084; and 4,880,784, among others, relevant portions of which are incorporated by reference herein.

The compounds disclosed in the above-referenced patents may be used in combination with the present compounds for their additive activity or treatment profile against HIV and/or other viruses and in certain instances, for their synergistic effects in combination with compounds of the present invention. Preferred secondary or additional compounds for use with the present compounds are those which do not inhibit HIV or another virus. Certain compounds according to the present invention may be effective for enhancing the biological activity of certain agents according to the present invention by reducing the metabolism or inactivation of other compounds and as such, are co-administered for this intended effect.

The present invention is now described, purely by way of illustration, in the following examples. It will be understood by one of ordinary skill in the art that these examples are in no way limiting and that variations of detail can be made without departing from the spirit and scope of the present invention.
Chemistry The novel compounds of the instant invention were generally prepared in the manner following the general synthetic description set forth in FIGS. 4-7C. The remaining compounds may be readily synthesized by analogy. In general, the nucleoside analog (i.e., a compound containing the base and sugar synthon) is prepared initially and the corresponding 4' group is introduced as depicted generally in Schemes A and B and as otherwise described in the experimental. One of ordinary skill will readily be able to synthesize compounds according to the present invention by analogy following the synthesis presented in the experimental without engaging in undue experimentation.

Figure 4:
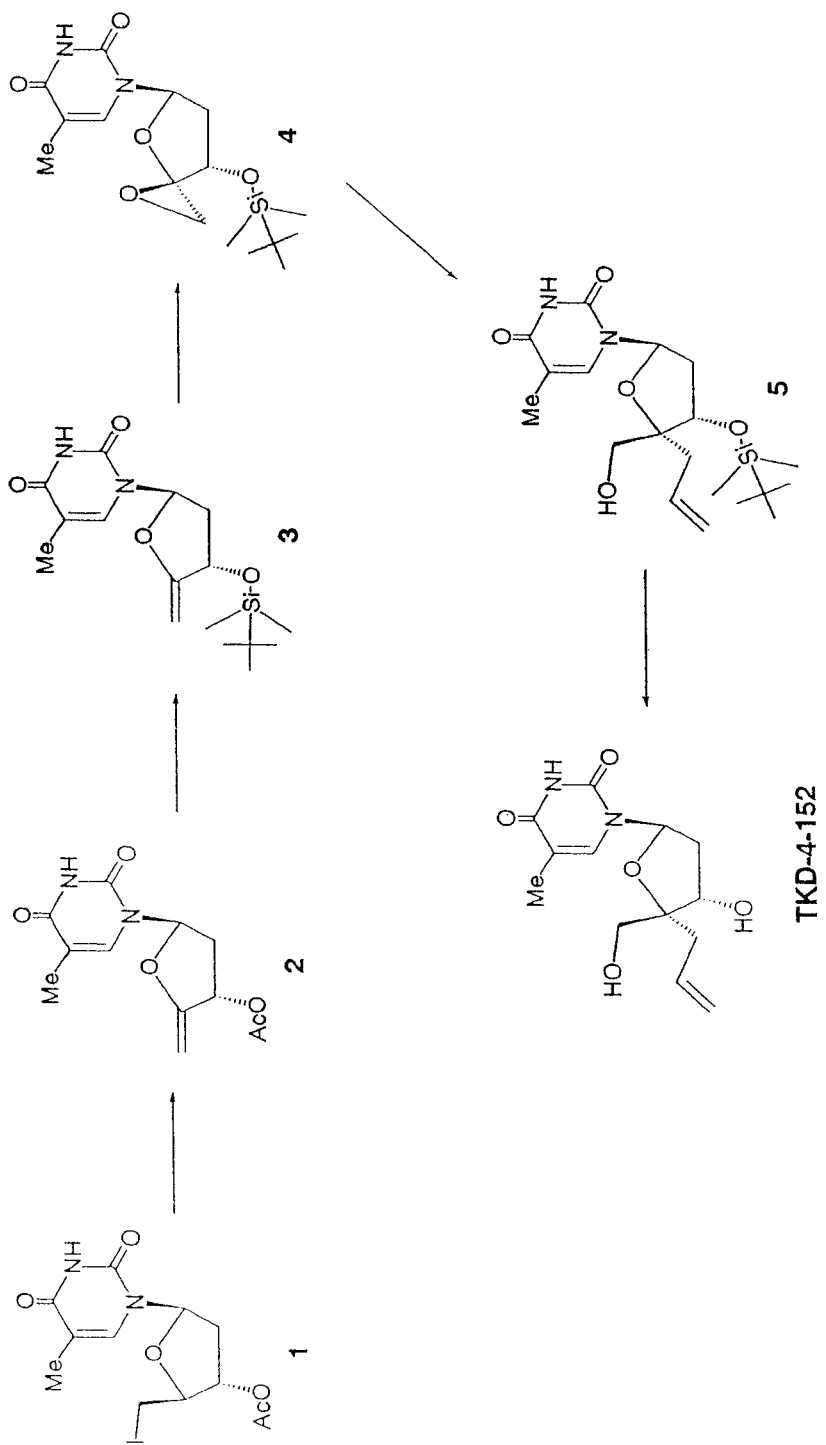
FIG. 4 shows the chemical synthesis of TDK-4-152 in Scheme A.

As set forth in FIG. 4, the 5'-iodo, 3'-O-blocked 2'-deoxynucleoside is converted to a 4'5'-vinyl blocked nucleoside 2 which is then converted in a series of steps through a 4'5'-oxirane blocked nucleoside 4 to the 4'-vinyl compound TDK-4-152. As set forth in FIG. 5, TKD-4-114 is synthesized from a 5'-iodo-3'-O-blocked nucleoside compound 7 by forming the 4',5'-vinyl compound 8, introducing the ethynyl group at the 4'-position of the blocked nucleoside to form nucleoside 10a and then ultimately forming the 2',3' unsaturated double bond through elimination of a mesylated hydroxyl group at the 3' position of compound 13. Other compounds according to the present invention are synthesized by analogy using the above-described chemical schemes.

Figure 5:
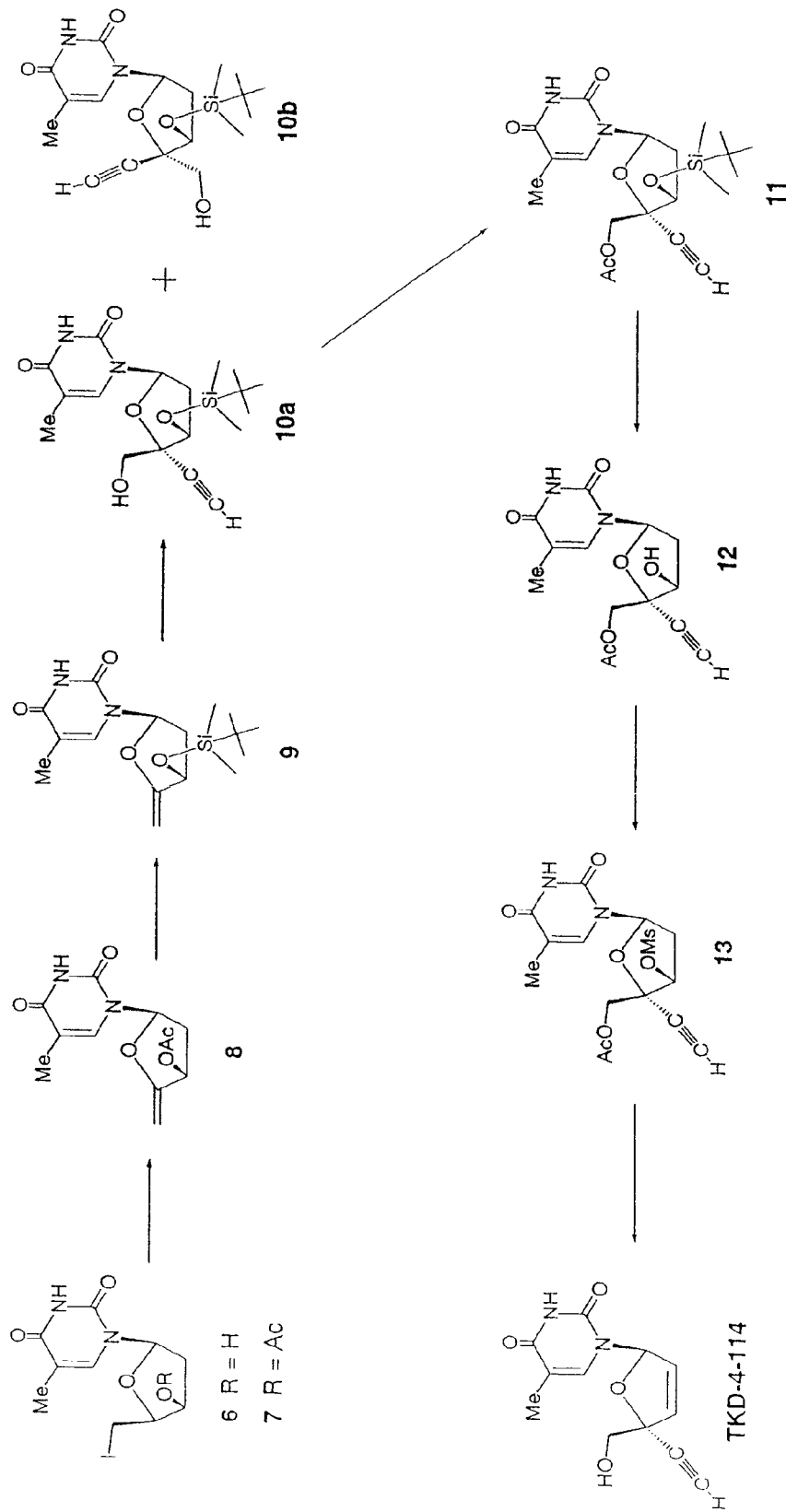
FIG. 5 shows the chemical synthesis of TDK-4-114 in Scheme B.
Figure 5A:
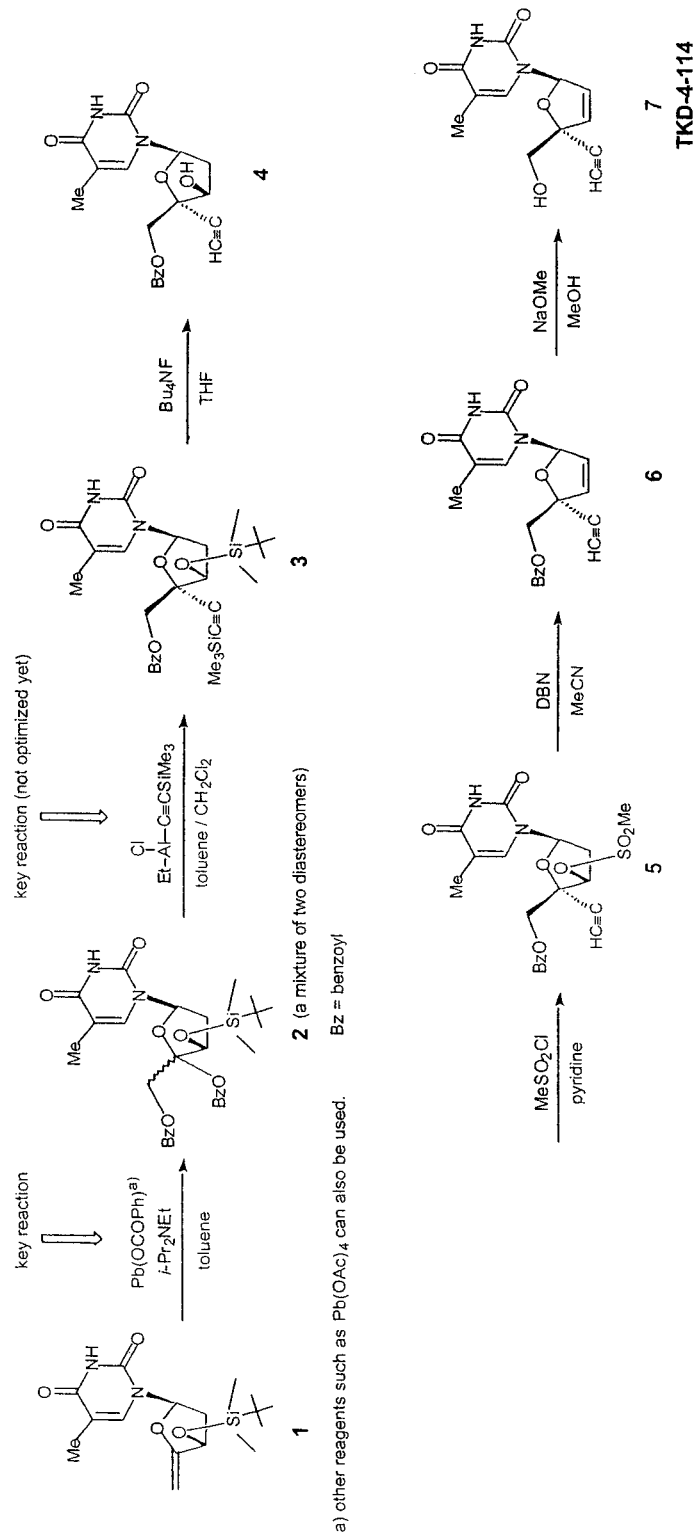
FIG. 5A shows an alternative chemical synthesis of TDK-4-114.
Figure 5B:
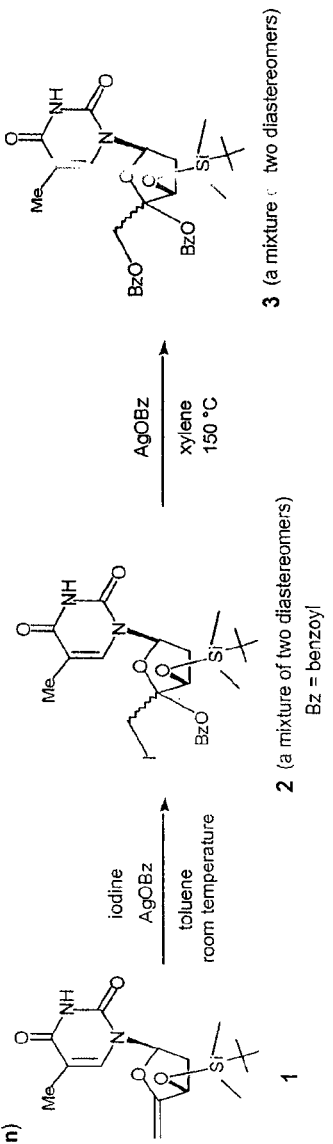
FIG. 5B shows an alternative preparation of acyloxy nucleoside compound intermediates according to the invention, which may be used to produced TKD-4-114 of FIG. 5A.
Figure 5B:
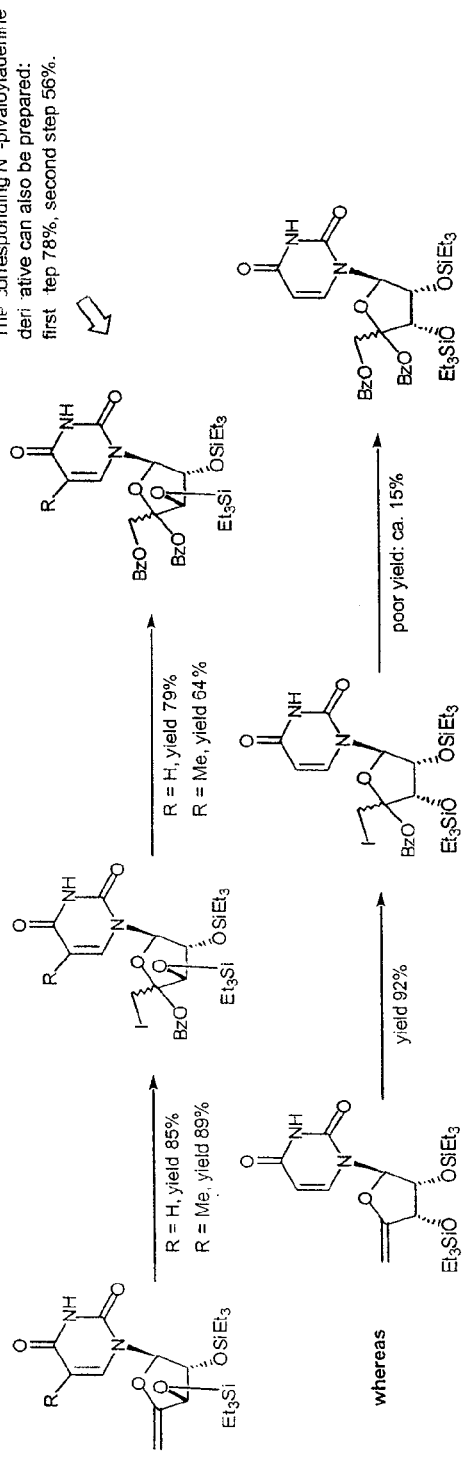

FIG. 5A shows an alternative synthesis of TDK-4-114 from intermediate 9 of FIG. 5. In this aspect of the invention, intermediate 9 is reacted with lead benzoate Pb(OCOPh) or lead tetraacetate Pb(OAc)$_4$ in a scavenging base such as triethyl amine, diisopropylethylamine, or pyridine in an appropriate solvent to produce the 4'5'-diacyl (benzoyl or acetyl) blocked nucleoside 2 (FIG. 5A), depending upon the lead (Pb) acylating agent used. Introduction of a 4'ethynyl group proceeds through intermediate blocked nucleoside 2 by action of aluminum acetylene agent EtAl(Cl)—C≡SiMe$_3$ (See FIG. 5A) in a solvent to produce 4'acetylene nucleoside compound 3 (FIG. 5A). Synthesis of TDK-4-114 proceeds in a straightforward manner by elimination of the mesylated hydroxyl group to form the 4'-ethynyl-2',3' unsaturated nucleoside compound 7. Note that intermediate 3 of FIG. 5A (and 5B) may alternatively be synthesized from the 4',5'vinyl blocked nucleoside compound 1 of FIGS. 5A and 5B (identical to compound 9 of FIG. 5) by a two step reaction to form the di-O-benzoyl compound 3 (or di-O-acetyl) of FIG. 5B using a first step of iodine and silver benzoate (silver acetate) in solvent to form intermediate 2 (FIG. 5B) which can be reacted further with silver benzoate (silver acetate) in solvent at elevated temperature to form intermediate 3 (or the di-O-acetyl compound by analogy).

Figure 6:
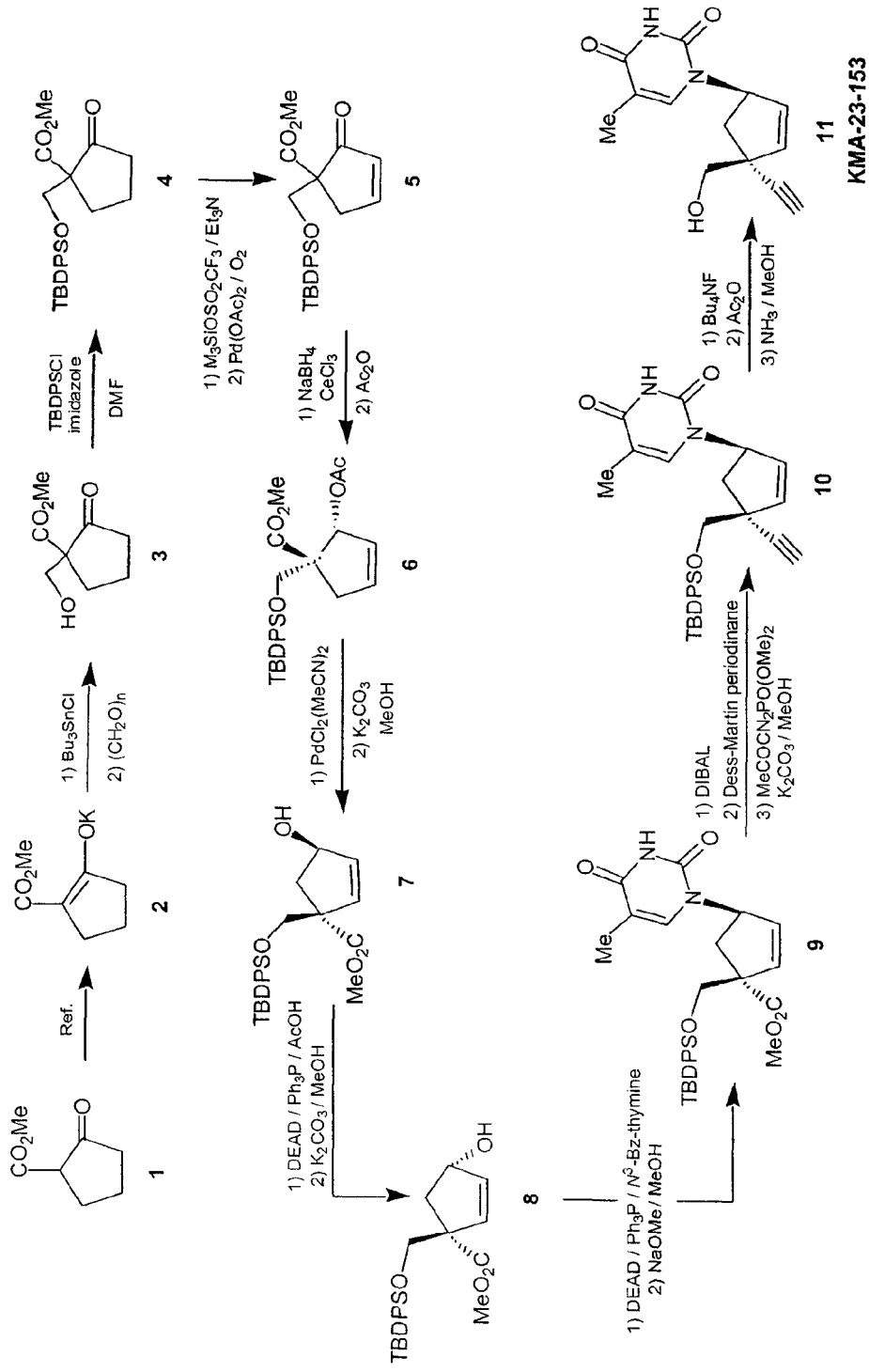
FIG. 6 shows a chemical synthesis of KMA-23-153.

The chemical synthetic scheme in FIG. 6 exemplifies the synthesis of the unsaturated carbocyclic analog KMA-23-153

(FIG. 6) from cyclopentanone ester 1 (FIG. 6) which proceeds through a number of intermediates to form intermediate 8 (FIG. 6) which can be condensed with a nucleoside base to form intermediate 9 wherein the 4' ester can be converted to the 4'-ethynyl compound 10 followed by removal of the 5' blocking group to produce KMA-23-153.

Figure 7B:
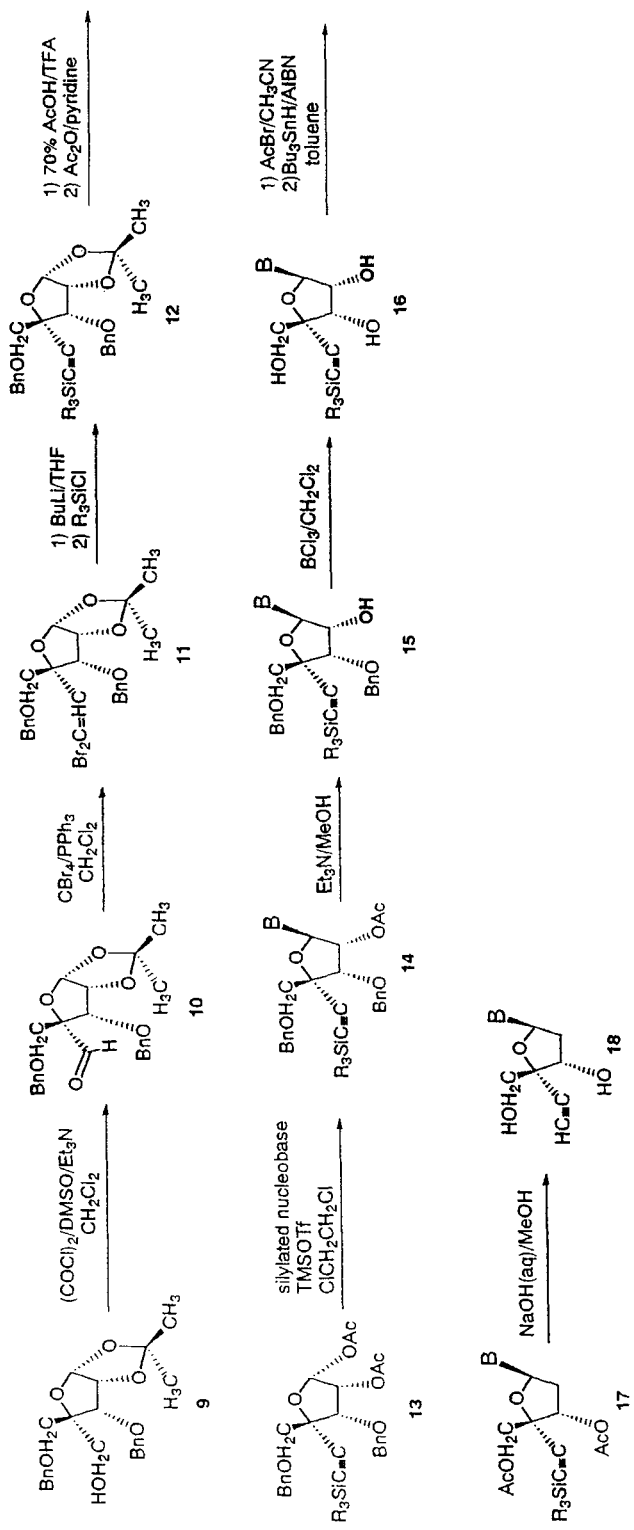
FIG. 7B shows the synthesis of 4'-ethynyl-2'-deoxynucleosides from a blocked sugar precursor according to the methodology of Ohrui, et al., *J. Med. Chem.* 43, 4516-4525 (2000). Note that B is a nucleoside base.
Figure 7C:
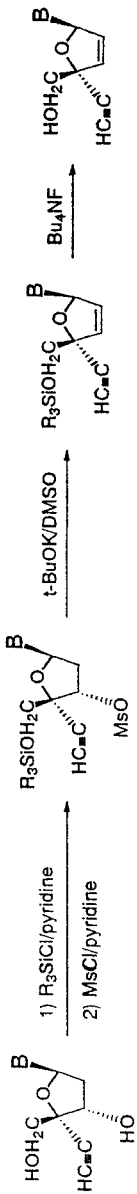
FIG. 7C shows a general chemical synthesis of 2',3'-didehydro nucleoside compounds from the corresponding 2' deoxynucleoside analogs according to the present invention.
Figure 7C:
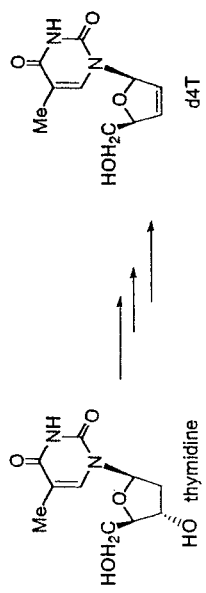

FIG. 7A shows the chemical synthesis of 4'-ethynyl-2'-deoxy nucleoside compounds following the general method of Nomura, et al., *J. Med. Chem.*, 42, 2901-2908 (1999) by introducing a halogenated vinyl group at the 4' position of the nucleoside which undergoes dehydrohalogenation to form the 4'-ethynyl nucleoside compound 8 (FIG. 7A). FIG. 7B shows the synthesis of the 4'-ethynyl-2'-deoxy nucleoside from a readily available sugar precursor 9 (FIG. 7B) which proceeds through the introduction of a 4'-halogenated vinyl group to a 4'-formyl group of the sugar synthon 10 to form 11 (FIG. 7B) followed by dehydrohalogenation, introduction of the nucleoside base and eventual conversion of the 2' hydroxyl group in a series of steps to form compound 18. FIG. 7C Scheme 3 shows the introduction of a 2',3'-double bond in a 4'-ethynyl analog by mesylating the 3'OH group followed by reacting mesylated intermediate with strong base to produce the double bond at the 2',3' position of the sugar.

Following one or more of the above-described synthetic methods and using routine synthetic methods well-known in the art, one of ordinary skill may readily produce compounds according to the present invention.

SPECIFIC EXAMPLES

Chemical Synthesis Following Schemes A and B in FIG. 5 and FIG. 6

Synthesis of TKD-4-152 (FIG. 4)

TKD-4-152

(4'-allylthymidine) was synthesized by a series of reactions shown in FIG. 5, Scheme A, starting from compound 1 which was prepared according to the published procedure: J. P. H. Verheyden and J. G. Moffatt, *J. Org. Chem.*, 39, 3573-3579 (1974).

1-[3-O-(t-Butyldimethylsilyl)-2,5-dideoxy-β-D-glycero-pent-4-enofuranosyl]thymine (3)

To an $CH_3CN$ (150 mL) solution of 1 (11.9 g, 30.19 mmol) was added DBN (11.2 mL, 90.57 mmol) at 0° C. under Ar atmosphere, and the whole was stirred at room temperature overnight. After neutralization with AcOH, the reaction mixture was evaporated to dryness and the residue was partitioned between $CHCl_3$/saturated aqueous $NaHCO_3$ (200 mL×2/50 mL). Silica gel column chromatography (hexane/AcOEt=5/1-1/2) of the organic layer gave 2 (6.98 g, 87%) as a foam. Compound 2 (6.90 g, 25.92 mmol) was treated with saturated $NH_3$ in MeOH (350 mL) at 0° C. overnight. The reaction mixture was evaporated to dryness and dried overnight in vacuo. To a DMF (60 mL) solution of the residue were added imidazole (5.29 g, 77.75 mmol) and tert-butyldimethylsilyl chloride (7.81 g, 51.83 mmol) at 0° C. under Ar atmosphere, and the mixture was stirred at room temperature overnight. The reaction mixture was partitioned between $AcOEt/H_2O$ (300 mL/100 mL×5). Silica gel column chromatography (hexane/AcOEt=10/1-3/1) of the organic layer gave 3 (7.87 g, 90%) as a foam: UV (MeOH)$\lambda_{max}$ 264 nm (ε11100), $\lambda_{min}$ 234 nm (ε4900); $^1H$ NMR ($CDCl_3$) δ0.13 (6H, s, SiMe), 0.91 (9H, s, SiBu-t), 1.94 (3H, d, $J_{6,Me}$=1.2 Hz, Me), 2.13-2.20 (1H, m, H-2'a), 2.40 (1H, ddd, $J_{gem}$=13.6 Hz, $J_{2'b,3'}$=3.4 Hz and $J_{1',2'b}$=6.2 Hz, H-2'b), 4.24 (1H, d, $J_{gem}$=2.0 Hz, H-5'a), 4.54 (1H, d, $J_{gem}$=2.0 Hz, H-5'b), 4.75 (1H, dd, $J_{2'a,3'}$=6.0 and $J_{2'b,3'}$=3.4 Hz, H-3'), 6.49 (1H, t, $J_{1',2'a}$=$J_{1',2'b}$=6.2 Hz, H-1'), 6.98 (1H, d, $J_{6,Me}$=1.2 Hz, H-6), 8.47 (1H, br, NH); FAB-MS m/z 339 (M$^+$+H). Anal. Calcd for $C_{16}H_{26}N_2O_4Si$: C, 56.78; H, 7.74; N, 8.28. Found: C, 57.04; H, 7.99; N, 8.14.

3'-O-(t-Butyldimethylsilyl)thymidine 4',5'-epoxide (4)

To a $CH_2Cl_2$ (3 mL) solution of 3 (20 mg, 0.059 mmol) was added dimethyldioxirane (0.072 M in acetone, 1.2 mL, 0.089 mmol) at −30° C. under Ar atmosphere, and the reaction mixture was stirred for 30 min at −30° C. Evaporation of the solvents gave 4 as a solid: $^1H$ NMR ($CDCl_3$) δ0.09, 0.10 (6H, each as s, SiMe), 0.90 (9H, s, SiBu-t), 1.95 (311, d, $J_{6,Me}$=1.3 Hz, Me), 2.25 (1H, ddd, $J_{gem}$=14.0 Hz, $J_{2'a,3'}$=4.9 Hz and $J_{1',2'a}$=7.1 Hz, H-2'a), 2.52 (1H, ddd, $J_{gem}$=14.0 Hz, $J_{2'b,3'}$=1.6 Hz and $J_{1',2'b}$=6.2 Hz, H-2'b), 3.07 (1H, d, $J_{gem}$=3.3 Hz, H-5'a), 3.36 (1H, d, $J_{gem}$=3.3 Hz, H-5'b), 4.26 (1H, dd, $J_{2'a,3'}$=4.9 and $J_{2'b,3'}$=1.6 Hz), 6.12 (1H, dd, $J_{1',2'a}$=7.1 Hz and $J_{1',2'b}$=6.2 Hz, H-1'), 7.27 (1H, d, $J_{6,Me}$=1.3 Hz, H-6), 9.06 (1H, br, NH); FAB-MS m/z 355 (M$^+$+H).

3'-O-(t-Butyldimethylsilyl)-4'-α-allylthymidine (5)

To a $CH_2Cl_2$ (5 mL) solution of 3 (80 mg, 0.24 mmol) was added dimethyldioxirane (0.098 M in acetone, 3.6 mL, 0.36 mmol) at −30° C. under Ar atmosphere, and the mixture was stirred for 30 min at −30° C. The solvents were evaporated and the residue was dried in vacuo for 1 h to give 4. To a $CH_2Cl_2$ (5 mL) solution of 4 were added allyltrimethylsilane (0.11 mL, 0.71 mmol) and $SnCl_4$ (1 M in $CH_2Cl_2$, 0.71 mL, 0.71 mmol) at −30° C. under Ar atmosphere, and the mixture was stirred for 4 h at −30° C. After being quenched with saturated aqueous $NaHCO_3$, the reaction mixture was filtered through celite pad. The filtrate was partitioned between $CHCl_3$/saturated aqueous $NaHCO_3$ (60 mL×3/20 mL). The organic layer was evaporated to dryness and the residue was treated with saturated $NH_3$ in MeOH (30 mL) at room temperature for 12 h. Evaporation followed by preparative TLC (hexane/EtOAc=2/3) purification of the organic layer gave 5 (75 mg, 80%) as a foam: UV (MeOH)$\lambda_{max}$ 267 nm (ε12700), $\lambda_{min}$ 235 nm (ε5900); $^1H$ NMR ($CDCl_3$) δ0.08, 0.08 (6H, each as s, SiMe), 0.89 (9H, s, SiBu-t), 1.87 (3H, d, $J_{6,Me}$=1.1 Hz, Me), 2.16 (1H, dd, $J_{gem}$=14.5 Hz and $J_{6'a,7'}$=8.1 Hz, C$\underline{H}_2$CH=$CH_2$), 2.27-2.39 (2H, m, H-2'), 2.44 (1H, dd, $J_{gem}$=14.5 Hz and $J_{6'b,7'}$=6.3 Hz, C$\underline{H}_2$CH=$CH_2$), 2.94 (1H, br, OH), 3.52 (1H, dd, $J_{gem}$=11.8 Hz and $J_{5',OH}$=6.1 Hz, H-5'a), 3.73 (1H, dd, $J_{gem}$=11.8 Hz and $J_{5',OH}$=2.7 Hz, H-5'b), 4.62 (1H, dd, $J_{2'a,3'}$=5.8 Hz and $J_{2'b,3'}$=7.0 Hz, H-3'), 5.07-5.13 (2H, m, $CH_2CH=C\underline{H}_2$), 5.83-5.93 (1H, m, $CH_2C\underline{H}=CH_2$), 6.11 (1H, dd, $J_{1',2'a}$=5.8 Hz and $J_{1',2'b}$=6.9 Hz, H-1'), 7.45 (1H, d, $J_{6,Me}$=1.1 Hz, H-6), 9.40 (1H, br, NH); nOe experiment, H-1'/C$\underline{H}_2$CH=$CH_2$ (0.8%), $CH_2$-5'/H-3' (5.3%), $CH_2$-5'/H-6 (0.6%), HO-5'/H-3' (0.7%) and HO-5'/H-6 (1.2%); FAB-MS m/z 397 (M$^+$+H). Anal. Calcd for $C_{19}H_{32}N_2O_5Si·⅓H_2O$: C, 56.69; H, 8.18; N, 6.96. Found: C, 56.46; H, 8.18; N, 6.87.

TKD-4-152 (4'-allylthymidine) FIG. 4

A mixture of 5 (59 mg, 0.149 mmol) and tetrabutylammonium fluoride (58 mg, 0.223 mmol) in THF (3 mL) was stirred at room temperature for 12 h. Silica gel column chromatography ($CHCl_3$/MeOH=20/1) of the evaporated reaction mixture gave TKD-4-152 (37.7 mg, 90%) as a foam: UV (MeOH) $\lambda_{max}$ 267 nm (ε9300), $\lambda_{min}$ 235 nm (ε2000); $^1H$ NMR δ 1.86

(3H, d, $J_{6,Me}$=1.2 Hz, Me), 2.27-2.35 (3H, m, H-2' and CH$_2$CH=CH$_2$), 2.42-2.48 (1H, m, CH$_2$CH=CH$_2$), 3.56 (1H, d, $J_{gem}$=11.8 Hz, H-5'a), 3.64 (1H, d, $J_{gem}$=11.8 Hz, H-5'b), 4.48 (1H, t, $J_{2'a,3'}$=$J_{2'b,3'}$=5.8 Hz, H-3'), 5.04-5.13 (2H, m, CH$_2$CH=CH$_2$), 5.88-5.98 (1H, m, CH$_2$CH=CH$_2$), 6.23 (1H, t, $J_{1',2'a}$=$J_{1',2'b}$=6.5 Hz, H-1'), 7.89 (1H, d, $J_{6,Me}$=1.2 Hz, H-6); FAB-MS m/z 283 (M$^+$+H), 321 (M$^+$+K). Anal. Calcd for C$_{13}$H$_{18}$N$_2$O$_5$·½H$_2$O: C, 54.16; H, 6.57; N, 9.62. Found: C, 53.87; H, 6.49; N, 9.28.

TKD-4-114

(2',3'-didehydro-3'-deoxy-4'-ethynylthymidine, 4'-ethynyl-d4T) was synthesized by a series of reactions shown in Scheme B, starting from compound 6 which was prepared according to the published procedure: B. V. Joshi and C. B. Reese, *Tetrahedron Lett.*, 32, 2371-2374 (1992).

1-(3-O-Acetyl-2,5-dideoxy-5-iodo-β-D-threo-pento-furanosyl)-thymine (7)

A mixture of 6 (5.3 g, 15.05 mmol) and Ac$_2$O (4.3 mL, 45.15 mmol) in pyridine (30 mL) was stirred at room temperature for 13 h. The reaction mixture was partitioned between CHCl$_3$/saturated aqueous NaHCO$_3$ (250 mL×3/50 mL). Silica gel column chromatography (hexane/EtOAc=1/1-1/2) of the organic layer gave 7 (5.53 g, 93%) as a foam: $^1$H NMR (CDCl$_3$) δ1.96 (3H, s, Me), 2.11 (3H, s, Ac), 2.11-2.16 (1H, m, H-2'a), 2.82 (1H, ddd, $J_{gem}$=15.8 Hz, $J_{1',2'b}$=8.0 Hz and $J_{2'b,3'}$=5.7 Hz, H-2'b), 3.32-3.39 (2H, m, H-5'), 4.28 (1H, dt, $J_{3',4'}$=3.3 Hz and $J_{4',5'}$=7.1 Hz, H-4'), 5.48 (1H, dd, $J_{2'b,3'}$=5.7 Hz and $J_{3',4'}$=3.3 Hz H-3'), 6.30 (1H, dd, $J_{1',2'a}$=2.8 Hz and $J_{1',2'b}$=8.0 Hz, H-1'), 7.38 (1H, d, $J_{6,Me}$=0.7 Hz, H-6), 8.59 (1H, br, NH); FAB-MS m/z 395(M$^+$+H).

1-(3-O-Acetyl-2,5-dideoxy-β-L-glycero-pent-4-eno-furanosyl)-thymine (8)

To an CH$_3$CN (40 mL) solution of 7 (5.5 g, 13.95 mmol) was added DBN (6.9 mL, 55.81 mmol) at 0° C., and the reaction mixture was stirred at room temperature for 17 h. After neutralization with AcOH, the reaction mixture was evaporated to dryness. The residue was partitioned between CHCl$_3$/saturated aqueous NaHCO$_3$ (200 mL×3/50 mL). Silica gel column chromatography (hexane/EtOAc=2/1-1/1) of the organic layer gave 8 (3.34 g, 90%) as a foam: $^1$H NMR (CDCl$_3$) δ: 1.96 (3H, d, $J_{6,Me}$=1.3 Hz, Me), 2.06 (3H, s, Ac), 2.21 (1H, dt, $J_{gem}$=15.2 Hz, $J_{1',2'a}$=$J_{2'a,3'}$=2.7 Hz, H-2'a), 2.83 (1H, dt, $J_{gem}$=15.2 Hz, $J_{1',2'b}$=$J_{2'b,3'}$=7.1 Hz, H-2'b), 4.51 (1H, dd, $J_{gem}$=2.4 Hz, $J_{3',5'a}$=0.8 Hz, H-5'a), 4.73 (1H, dd, $J_{gem}$=2.4 Hz and $J_{3',5'b}$=0.7 Hz, H-5'b), 5.70-5.73 (1H, m, H-3'), 6.44 (1H, dd, $J_{1',2'a}$=2.7 Hz and $J_{1',2'b}$=7.1 Hz, H-1'), 7.25 (1H, d, $J_{6,Me}$=1.3 Hz, H-6), 8.54 (1H, br, NH); FAB-MS m/z 267 (M$^+$+H).

1-[3-O-(t-Butyldimethylsilyl)-2,5-dideoxy-β-L-glycero-pent-4-enofuranosyl]thymine (9)

Compound 8 (5.2 g, 19.53 mmol) in saturated NH$_3$ in MeOH (150 mL) was kept at room temperature for 9 h. After evaporation, the residue was dissolved in DMF (60 mL). To this were added imidazole (5.32 g, 78.12 mmol) and tert-butyldimethylsilyl chloride (8.83 g, 58.59 mmol) at 0° C. The reaction mixture was stirred at room temperature for 11 h, and then partitioned between EtOAc/H$_2$O (250 mL/50 mL×4). Silica gel column chromatography (hexane/EtOAc=10/1) of the organic layer gave 9 (6.43 g, 97%) as a foam: UV (MeOH) $\lambda_{max}$ 266 nm (ε11600), $\lambda_{min}$ 236 nm (ε5700); $^1$H NMR (CDCl$_3$) δ 0.11 and 0.14 (6H, each as s, SiMe), 0.88 (9H, s, SiBu-t), 1.92 (3H, d, $J_{6,CH3}$=1.2 Hz, Me), 2.03 (1H, dt, $J_{gem}$=10.8 Hz, $J_{1',2'a}$=3.2 Hz and $J_{2'a,3'}$=3.2 Hz, H-2'a), 2.61-2.68 (1H, m, H-2'b), 4.25 (1H, d, $J_{gem}$=2.2 Hz, H-5'a), 4.57 (1H, d, $J_{gem}$=2.2 Hz, H-5'b), 4.68 (1H, dd, $J_{2'a,3'}$=3.2 Hz, $J_{2'b,3'}$=6.8 Hz H-3'), 6.46 (1H, dd, $J_{1',2'a}$=3.2 Hz and $J_{1',2'b}$=7.2 Hz, H-1'), 7.44 (1H, d, $J_{6,CH3}$=1.2 Hz, H-6), 9.12 (1H, br, NH); FAB-MS m/z 339(M$^+$+H). Anal. Calcd for C$_{16}$H$_{26}$N$_2$O$_4$Si: C, 56.78; H, 7.74; N, 8.28. Found: C, 56.61; H, 7.87; N, 8.17.

1-[2-Deoxy-3-O-(t-butyldimethylsilyl)-4-ethynyl-β-D-threo-pento-furanosyl]thymine (10a) and 1-[2-Deoxy-3-O-(t-butyldimethyl-silyl)-4-ethynyl-α-L-erythro-pentofuranosyl]thymine (10b)

To a solution of 9 (60 mg, 0.177 mmol) in CH$_2$Cl$_2$ (5 mL) was added dimethyldioxirane (0.09 M in acetone, 3.0 mL, 0.266 mmol) at −30° C. After stirring for 0.5 h, the mixture was evaporated and dried in vacuo for 1 h. The residue was dissolved in CH$_2$Cl$_2$ (5 mL). To this solution was added triethynylaluminum (0.3 M in CH$_2$Cl$_2$, 1.8 mL, 0.532 mmol) at −30° C. under Ar atmosphere, and the reaction mixture was stirred at room temperature for 17 h. After being quenched with saturated aqueous NH$_4$Cl, the reaction mixture was filtered through celite pad. The filtrate was partitioned between CHCl$_3$/saturated aqueous NH$_4$Cl (60 mL×3/20 mL). HPLC separation (hexane/EtOAc=2/3) of the organic layer gave 10a ($t_R$=10.8 min, 39.3 mg, 58%, foam) and 10b ($t_R$=16.2 min, 18.8 mg, 28%, solid). Physical data for 10a: UV (MeOH): $\lambda_{max}$ 266 nm (ε12100), $\lambda_{min}$ 235 nm (ε6000); $^1$H NMR (CDCl$_3$) δ0.11 and 0.16 (6H, each as s, SiMe), 0.90 (9H, s, SiBu-t), 1.91 (3H, d, $J_{6,Me}$=1.3 Hz, Me), 1.91-1.96 (1H, 1H-2'a), 2.33 (1H, br, OH), 2.62 (1H, s, ethynyl), 2.95 (1H, ddd, $J_{gem}$=14.6 Hz, $J_{1',2'b}$=7.9 Hz and $J_{2'b,3'}$=5.5 Hz, H-2'b), 3.93 (1H, d, $J_{gem}$=11.6 Hz, H-5'a), 3.99 (1H, d, $J_{gem}$=11.6 Hz, H-5'b), 4.49 (1H, dd, $J_{2'a,3'}$=2.0 Hz and $J_{2'b,3'}$=5.5 Hz, H-3'), 6.39 (1H, dd, $J_{1',2'a}$=3.7 Hz and $J_{1',2'b}$=7.9 Hz, H-1'), 7.65 (1H, d, $J_{6,CH3}$=1.3 Hz, H-6), 8.72 (1H, br, NH); FAB-MS m/z 381 (M$^+$+H). Anal. Calcd for C$_{18}$H$_{28}$N$_2$O$_5$Si·H$_2$O: C, 54.24; H, 7.59; N, 7.03. Found: C, 54.46; H, 7.20; N, 6.72.

Physical data for 10b: mp 96-98° C.; UV (MeOH):$\lambda_{max}$ 267 nm (ε9300), $\lambda_{min}$ 235 nm (ε1700). $^1$H NMR (CDCl$_3$) δ0.08 and 0.13 (6H, each as s, SiMe), 0.89 (9H, s, SiBu-t), 1.93 (3H, d, $J_{6,CH3}$=0.9 Hz, Me), 2.12-2.17 (1H, m, H-2'a), 2.63 (1H, br, OH), 2.71-2.77 (1H, m, H-2'b), 2.75 (1H, s, ethynyl), 3.67 (1H, d, $J_{gem}$=11.5 Hz, H-5'a), 3.74 (1H, d, $J_{gem}$=11.5 Hz, H-5'b), 4.47 (1H, t, $J_{2'a,3'}$=$J_{2'b,3'}$=5.3 Hz, H-3'), 6.30 (1H, dd, $J_{1',2'a}$=4.8 Hz and $J_{1',2'b}$=6.9 Hz, H-1'), 7.80 (1H, d, $J_{6,CH3}$=0.9 Hz, H-6), 9.00 (1H, brs, NH); FAB-MS m/z 381 (M$^+$+H). Anal. Calcd for C$_{18}$H$_{28}$N$_2$O$_5$Si: C, 56.82; H, 7.42; N, 7.36. Found: C, 56.57; H, 7.58; N, 7.19.

1-[5-O-Acetyl-2-deoxy-3-O-(t-butyldimethylsilyl)-4-ethynyl-β-D-threo-pentofuranosyl]thymine (11)

To a pyridine (4 mL) solution of 10a (161 mg, 0.423 mmol) was added Ac$_2$O (120 mL, 1.269 mmol) at 0° C., and the mixture was stirred at room temperature for 11 h. The reaction mixture was partitioned between CHCl$_3$/saturated aqueous NaHCO$_3$ (60 mL×3/20 mL). Silica gel column chromatography (hexane/EtOAc=3/1) of the organic layer gave 11 (169.7 mg, 95%) as a foam: UV (MeOH):$\lambda_{max}$ 266 nm (ε9200), $\lambda_{min}$ 234 nm (ε2000); $^1$H NMR (CDCl$_3$) δ0.10 and 0.14 (6H, each as s, SiMe), 0.90 (9H, s, SiBu-t), 1.90-1.94 (4H, m, H-2'a and Me), 2.14 (3H, s, Ac), 2.58 (1H, s, ethynyl), 3.01 (1H, ddd, $J_{gem}$=14.8 Hz, $J_{1',2'b}$=8.3 Hz and $J_{2'b,3'}$=5.0 Hz, H-2'b), 4.37 (1H, d, $J_{gem}$=11.1 Hz, H-5'a), 4.45 (1H, d, $J_{2'b,3'}$=5.0 Hz, H-3'), 4.53 (1H, d, $J_{gem}$=11.1 Hz, H-5'b), 6.40 (1H, dd, $J_{1',2'a}$=2.8 Hz and $J_{1',2'b}$=8.3 Hz, H-1'), 7.53 (1H, d, $J_{6,Me}$=1.3 Hz, H-6), 8.04 (1H, br, NH); FAB-MS m/z 461 (M++K). Anal. Calcd for $C_{20}H_{30}N_2O_6Si$: C, 56.85; H, 7.16; N, 6.63. Found: C, 56.84; H, 7.35; N, 6.26.

1-(5-O-Acetyl-2-deoxy-4-ethynyl-β-D-threo-pentofuranosyl)-thymine (12)

To a THF (4 mL) solution of 11 (169.7 mg, 0.402 mmol) was added tetrabutylammonium fluoride (1M in THF, 602 μL, 0.602 mmol) under Ar atmosphere. After being stirred for 1 h at room temperature, the solvent was evaporated. Silica gel column chromatography ($CHCl_3$/MeOH=100/1) of the residue gave 12 (114.7 mg, 93%) as a foam: UV (MeOH), $\lambda_{max}$ 265 nm (ε8400), $\lambda_{min}$ 233 nm (ε1700); $^1$H NMR ($CDCl_3$ after addition of $D_2O$) δ1.93 (3H, d, $J_{6,Me}$=1.3 Hz, Me), 2.14-2.18 (1H, m, H-2'a), 2.18 (3H, s, Ac), 2.59 (1H, s, ethynyl), 2.94-3.02 (1H, m, H-2'b), 4.22 (1H, d, $J_{gem}$=11.4 Hz, H-5'a), 4.31 (1H, d, $J_{2'b,3'}$=5.5 Hz, H-3'), 4.68 (1H, d, $J_{gem}$=11.4 Hz, H-5'b), 6.24 (1H, dd, ss$J_{1'2'a}$=2.9 Hz and $J_{1',2'b}$=9.0 Hz, H-1'), 7.60 (1H, d, $J_{6,Me}$=1.3 Hz, H-6); $^{13}$C NMR ($CDCl_3$) δ12.52, 20.84, 38.76, 63.30, 74.73, 76.23, 79.85, 82.08, 85.33, 111.41, 137.93, 150.53, 163.63, 171.98; FAB-HR-MS m/z calcd for $C_{14}H_{17}N_2O_6$ 309.1087 ($M^+$+H). Found 309.1074.

1-(5-O-Acetyl-2-deoxy-3-O-methanesulfonyl-4-ethynyl-3-D-threo-pentofuranosyl)thymine (13)

To a pyridine (4 mL) solution of 12 (76 mg, 0.247 mmol) was added methanesulfonyl chloride (57 μL, 0.74 mmol) at 0° C., and the mixture was stirred at room temperature for 16 h. The reaction mixture was partitioned between $CHCl_3$/saturated aqueous $NaHCO_3$ (60 mL×3/20 mL). Silica gel column chromatography ($CHCl_3$/MeOH=100/0-100/1) of the organic layer gave 13 (95.0 mg, 100%) as a foam: $^1$H NMR ($CDCl_3$) δ1.96 (3H, d, $J_{6,Me}$=1.2 Hz, Me), 2.16 (3H, s, Ac), 2.38 (1H, ddd, $J_{gem}$=16.0 Hz, $J_{1',2'a}$=3.5 Hz and $J_{2'a,3'}$=0.7 Hz, H-2'a), 2.70 (1H, s, ethynyl), 3.11 (1H, s, Ms), 3.19 (1H, ddd, $J_{gem}$=16.0 Hz, $J_{1',2'b}$=8.4 Hz and $J_{2'b,3'}$=5.5 Hz, H-2'b), 4.48 (1H, d, $J_{gem}$=11.3 Hz, H-5'a), 4.53 (1H, d, $J_{gem}$=11.3 Hz, H-5'b), 5.27-5.28 (1H, m, H-3'), 6.52 (1H, dd, $J_{1',2'a}$=3.5 Hz and $J_{1',2'b}$=8.4 Hz, H-1'), 7.33 (1H, d, $J_{6,Me}$=1.2 Hz, H-6), 8.86 (1H, brs, NH); FAB-MS m/z 387($M^+$+H).

TKD-4-114 (2',3'-didehydro-3'-deoxy-4'-ethynylthymidine)

A mixture of 13 (105 mg, 0.272 mmol) and DBN (101 μL, 0.815 mmol) in $CH_3CN$ (10 mL) was refluxed for 11 h. After being quenched with AcOH, the reaction mixture was partitioned between $CHCl_3$/saturated aqueous $NaHCO_3$ (60 mL×3/20 mL). The product, obtained after purification by silica gel column chromatography (hexane/EtOAc=1/1) of the organic layer, was dissolved in saturated $NH_3$ in MeOH (30 mL), and kept at room temperature for 12 h. Evaporation of the solvent followed by preparative TLC (hexane/EtOAc=1/1) purification gave TKD-4-114 (49.6 mg, 74%) as a solid: mp 207-209° C.; UV (MeOH) $\lambda_{max}$ 264 nm (ε10800), $\lambda_{min}$ 235 nm (ε4800); $^1$H NMR ($CDCl_3$) δ1.83 (3H, s, Me), 2.63 (1H, s, ethynyl), 3.47 (1H, br, OH), 3.88 (1H, d, $J_{gem}$=12.5 Hz, H-5'a), 3.96 (1H, d, $J_{gem}$=12.5 Hz, H-5'b), 5.91 (1H, dd, $J_{1',2'}$=1.1 Hz and $J_{2',3'}$=5.9 Hz, H-2'), 6.30 (1H, dd, $J_{1',3'}$=2.0 Hz and $J_{2',3'}$=5.9 Hz, H-3'), 7.16-7.17 (1H, m, H-1'), 7.44 (1H, d, $J_{6,Me}$=1.1 Hz, H-6), 9.06 (1H, br, NH); FAB-MS m/z 249 ($M^+$+H). Anal. Calcd for $C_{12}H_{12}N_2O_4$·⅙$H_2O$: C, 57.37; H, 4.95; N, 11.15. Found: C, 57.36; H, 4.69; N, 10.98.

Alternative Chemical Synthesis of TDK-4-114 (FIG. 5A)

TKD-4-114 (2',3'-didehydro-3'-deoxy-4'-ethynylthymidine, 4'-ethynyl-d4T) was synthesized by a series of reactions shown in the Scheme (See FIG. 5A), starting from compound 1, the preparation of which has been reported previously.

Preparation of Dibenzoyl Compound 2 (a Mixture of Two Diastereomers)

To a toluene (70 mL) solution of 1 (3.98 mg, 11.76 mmol) was added i-$Pr_2$NEt (5.1 mL, 29.4 mmol) and Pb(OCOPh)$_4$ (20.33 g, 29.4 mmol) at 0° C. under Ar atmosphere, and the mixture was stirred for 4 h. The reaction mixture was quenched with sat. aqueous $NaHCO_3$, and filtered through celite. The filtrate was partitioned between $CHCl_3$/sat. aqueous $NaHCO_3$. The organic layer was purified by silica gel column chromatography (hexane/AcOEt=2/1) to give 2 (4.84 g, 71%) as a foam: $^1$H NMR ($CDCl_3$) δ0.02, 0.07, 0.15 and 0.20 (6H, each as s, SiMe), 0.75 and 0.93 (9H, each as s, SiBu-t), 1.69 and 1.91 (3H, each as d, $J_{6,Me}$=1.2 Hz, Me-5), 1.91-2.00, 2.33-2.40, 2.76-2.83 and 2.94-3.01 (2H, each as m, H-2'), 4.73 and 4.95 (1H, t and d, $J_{2',3'}$=6.8 and 4.4 Hz, H-3'), 4.91, 5.08, 5.11 and 5.19 (2H, each as d, $J_{gem}$=12.0 Hz, $CH_2$-5'), 4.24 (1H, d, $J_{gem}$=2.0 Hz), 6.34 and 6.64 (1H, d and dd, $J_{1',2'}$=6.4 and $J_{1',2'}$=2.8, 8.2 Hz, H-1'), 7.32-7.37, 7.45-7.51, 7.58-7.67, 7.92-7.94, 8.02-8.04 and 8.04-8.13 (11H, each as m, H-6 and Ph), 8.92 (1H, br, NH); FAB-MS (m/z) 581 ($M^+$+H). Anal. Calcd for $C_{30}H_{36}N_2O_8Si$: C, 62.05; H, 6.25; N, 4.82. Found: C, 61.85; H, 6.37; N, 4.70.

1-[5-O-Benzoyl-3-O-(t-butyldimethylsilyl)-2-deoxy-4-(trimethylsilyl)ethynyl-β-D-threo-pentofuranosyl]thymine (3)

To a toluene (40 mL) solution of HC≡CSiMe$_3$ (3.2 mL, 22.44 mmol) was added BuLi (2.44 M in hexane) (9.2 mL, 22.44 mmol) at 0° C. under Ar atmosphere, and the mixture was stirred for 30 min. To this solution was added EtAlCl$_2$ (0.94 M in hexane) (23.4 mL, 22.44 mmol) at 0° C. After the mixture being stirred for 30 min, 2 (3.26 g, 5.61 mmol) in $CH_2Cl_2$ (50 mL) was added at 0° C., and the mixture was stirred overnight. The reaction mixture was partitioned between $CHCl_3$/sat. aqueous $NaHCO_3$. The organic layer was purified by silica gel column chromatography (hexane/EtOAc=3/1) to give 3 (1.14 g, 37%) as a foam: $^1$H NMR ($CDCl_3$) δ0.09 and 0.13 (6H, each as s, SiMe), 0.12 (9H, s, C≡CSiMe$_3$), 0.89 (9H, s, SiBu-t), 1.90 (3H, d, $J_{Me,6}$=0.8 Hz, Me-5), 1.95 (1H, ddd, $J_{1',2'a}$=2.8, $J_{2'a,3'}$=1.2 and $J_{2'a,2'b}$=14.6 Hz, H-2'a), 3.02 (1H, ddd, $J_{1',2'b}$=8.2, $J_{2'b,3'}$=5.2 and $J_{2'a,2'b}$=14.6 Hz, H-2'b), 4.50 (1H, dd, $J_{2'a,3'}$=1.2 and $J_{2'b,3'}$=5.2 Hz, H-3'), 4.64 (1H, d, $J_{5'a,5'b}$=10.8 Hz, H-5'a), 4.68 (1H, d, $J_{5'a,5'b}$=10.8 Hz, H-5'b), 6.40 (1H, d, $J_{1',2'a}$=2.8 and $J_{1',2'b}$=8.2 Hz, H-1'), 7.44-7.48, 7.57-7.61 and 8.07-8.10 (6H, each as m, H-6 and Ph), 8.24 (1H, br); FAB-MS (m/z) 557 ($M^+$+H)

1-[5-O-Benzoyl-2-deoxy-4-ethynyl-β-D-threo-pentofuranosyl]thymine (4)

To a THF (5 mL) solution of 3 (208.2 mg, 0.37 mmol) was added Bu$_4$NF·3$H_2O$ (290.2 mg, 1.11 mmol) at 0° C., and the mixture was stirred for 1 h. The reaction mixture was evaporated to dryness. Silica gel column chromatography (2% MeOH in $CH_2Cl_2$) of the residue gave 3 (115.3 mg, 84%) as a foam: $^1$H NMR ($CDCl_3$+$D_2O$) δ1.94 (3H, d, $J_{Me,6}$=1.2 Hz, Me-5), 2.15 (1H, dd, $J_{1',2'a}$=3.2 and $J_{2'a,2'b}$=15.0 Hz, H-2'a), 2.60 (1H, s, C≡CH), 3.01 (1H, ddd, $J_{1',2'b}$=9.0, $J_{2'b,3'}$=5.2 and $J_{2'a,2'b}$=15.0 Hz, H-2'b), 4.34 (1H, d, $J_{2'b,3'}$=5.2 Hz, H-3'), 4.40 (1H, d, $J_{5'a,5'b}$=11.2 Hz), 4.96 (1H, d, $J_{5'a,5'b}$=11.2 Hz), 6.34 (1H, d, $J_{1',2'a}$=3.2 and $J_{1',2'b}$=9.0 Hz, H-1'), 7.46-7.51, 7.61-7.65 and 8.09-8.11 (5H, each as m, Ph), 7.70 (1H, d, $J_{Me,6}$=1.2 Hz), 8.47 (1H, br); FAB-MS (m/z) 371 (M$^+$+H).

1-[5-O-Benzoyl-2-deoxy-4-ethynyl-3-O-methane-sulfonyl-β-D-threo-pentofuranosyl]thymine (5)

To a pyridine (3.5 mL) solution of 4 (110.9 mg, 0.30 mmol) was added MsCl (0.12 mL, 1.5 mmol) at 0° C. under Ar atmosphere, and the mixture was stirred for 6 h. The reaction mixture was partitioned between CHCl$_3$/sat. aqueous NaHCO$_3$. Silica gel column chromatography (1.5% MeOH in CH$_2$Cl$_2$) of the organic layer gave 5 (105.2 mg, 78%) as a foam: $^1$H NMR (CDCl$_3$) δ1.92 (3H, d, $J_{Me,6}$=1.2 Hz, Me-5), 2.43 (1H, dd, $J_{1',2'a}$=3.6 and $J_{2'a,2'b}$=16.0 Hz, H-2'a), 2.72 (1H, s, C≡CH), 3.07 (3H, s, SO$_2$Me), 3.23 (1H, ddd, $J_{1',2'b}$=8.2, $J_{2'b,3'}$=5.2 and $J_{2'a,2'b}$=16.0 Hz, H-2'b), 4.72 (1H, d, $J_{5'a,5'b}$=11.2 Hz), 4.76 (1H, d, $J_{5'a,5'b}$=11.2 Hz), 5.37 (1H, d, $J_{2'b,3'}$=5.2 Hz, H-3'), 6.56 (1H, d, $J_{1',2'a}$=3.6 and $J_{1',2'b}$=98.2 Hz, H-1'), 7.36 (1H, d, $J_{Me,6}$=1.2 Hz), 7.47-7.51, 7.60-7.64 and 8.07-8.10 (5H, each as m, Ph), 8.32 (1H, br); FAB-MS (m/z) 449 (M$^+$+H).

5'-O-Benzoyl-2',3'-didehydro-3'-deoxy-4'-ethynylthymidine (6)

To an CH$_3$CN (4 mL) solution of 5 (101.9 mg, 0.18 mmol) was added DBN (67 μL, 0.54 mmol) at 0° C. under Ar atmosphere, and the mixture was stirred at 80° C. for 9 h. The reaction mixture was neutralized by adding AcOH, and partitioned between CHCl$_3$/sat. aqueous NaHCO$_3$. Silica gel column chromatography (1.5% MeOH in CH$_2$Cl$_2$) of the organic layer gave 6 (60 mg, 95%) as solid: $^1$H NMR (CDCl$_3$) δ1.42 (3H, d, $J_{Me,6}$=1.2 Hz, Me-5), 2.70 (1H, s, C≡CH), 4.59 (1H, d, $J_{5'a,5'b}$=12.0 Hz, H-5'a), 4.76 (1H, d, $J_{5'a,5'b}$=12.0 Hz, H-5'b), 5.99 (1H, dd, $J_{1',2'}$=1.2, $J_{2',3'}$=5.9, H-2'), 6.38 (1H, dd, $J_{1',3'}$=2.0 and $J_{2',3'}$=5.9 Hz, H-3'), 6.98 (1H, d, $J_{Me,6}$=1.2 Hz), 7.12 (1H, m, H-1'), 7.45-7.49, 7.60-7.63 and 8.00-8.03 (5H, each as m, Ph), 8.37 (1H, br); FAB-MS (m/z) 353 (M$^+$+H).

2',3'-Didehydro-3'-deoxy-4'-ethynylthymidine (7) (TKD-4-114, 4'-Ethynyl-d4T)

To a MeOH (3 mL) suspension of 6 (56 mg, 0.16 mmol) was added 1 M NaOMe (0.32 mL, 0.32 mmol) at 0° C. under Ar atmosphere, and the mixture was stirred at r.t. for 0 h. The reaction mixture was neutralized by adding AcOH and chromatographed on a silica gel column (2% MeOH in CH$_2$Cl$_2$) gave 7(35.8 mg, 90%) as solid.

Physical data of 7 (TKD-4-114) as set foreth above.

Chemical Synthesis of KMA-23-153: the carbocyclic analogue of TKD-4-114 (See FIG. 6)

KMA-23-153 was prepared as racemic a modification (a mixture of equal amount of D- and L-enantiomers) by a sequence of reactions shown in the Scheme set forth in FIG. 6. The Method for the preparation of starting material 2 has already been published: See, Kato, et al., *Chem. Pharm. Bull.,* 47, 1256-1264 (1999).

1-Hydroxymethyl-2-oxocyclopentanecarboxylic acid methyl ester (3 of FIG. 6)

To a suspension of 2 (10 g, 55.48 mmol) and HMPA (29 mL, 166.44 mmol) in THF (450 ml) was added Bu$_3$SnCl (16.5 mL, 61.0 mmol) at 0° C. under positive pressure of dry Ar. After stirring at 0° C. for 30 min, (CH$_2$O)$_n$ (8.32 g, 277.4 mmol) was added to the mixture and the whole reaction mixture was stirred for 48 h at room temperature. The reaction mixture was partitioned between AcOEt and brine. The organic layer was dried (Na$_2$SO$_4$), evaporated, and chromatographed on a silica gel column (hexane/EtOAc=1/1). This gave 3 (7.13 g, 77%) as an oil.

$^1$HNMR (CDCl$_3$) δ: 1.97-2.18 (2H, m, CH$_2$), 2.21-2.25 (1H, m, CH$_2$), 2.29-2.53 (3H, m, OH and CH$_2$), 2.62-2.66 (1H, m, CH$_2$), 3.74 (3H, s, Me), 3.81 (1H, dd, J=11.2 and 8.0 Hz, CH$_2$OH), 3.89 (1H, dd, J=11.2 and 4.4 Hz, CH$_2$OH).

1-(tert-Butyldiphenylsilyloxymethyl)-2-oxo-cyclopentanecarboxylic acid methyl ester (4 of FIG. 6)

A mixture of 3 (10.35 g, 60.1 mmol), imidazole (8.18 g, 120.2 mmol), and TBDPSCl (15.6 ml, 60.1 mmol) in DMF (40 ml) was stirred for 16 h at room temperature under positive pressure of dry Ar. The mixture was partitioned between EtOAc and sat. aqueous NaHCO$_3$. The organic layer was dried (Na$_2$SO$_4$) and evaporated. The resulting syrupy residue was treated with MeOH (ca. 40 ml) to give the precipitated 4. This procedure was repeated further 3 times to give 4 (18.97 g, 77%) as a white solid.

$^1$HNMR (CDCl$_3$) δ: 1.02 (9H, s, SiBu-t), 2.03-2.11 (2H, m, CH$_2$), 2.26-2.35 (1H, m, CH$_2$), 2.41-2.53 (3H, m, CH$_2$), 3.65 (3H, s, Me), 3.87 (1H, d, J=9.6 Hz, CH$_2$OSi), 4.09 (1H, d, J=9.6 Hz, CH$_2$OSi), 7.37-7.46 (6H, m, Ph), 7.61-7.65 (4H, m, Ph).

1-(tert-Butyldiphenylsilyloxymethyl)-2-oxocyclopent-3-enecarboxylic acid methyl ester (5 of FIG. 6)

To a stirring mixture of 4 (3.58 g, 8.72 mmol) and Et$_3$N (6.1 ml, 43.6 mmol) was added Me$_3$SiOSO$_2$CF$_3$ (2.56 mL, 13.0 mmol) at 0° C. under positive pressure of dry Ar. The mixture was stirred for 30 min at the same temperature, and then partitioned between CH$_2$Cl$_2$ and sat. aqueous NaHCO$_3$. The organic layer was dried (Na$_2$SO$_4$) and evaporated. The residue was dissolved in DMSO (12 mL). To this solution was added Pd(OAc)$_2$ (98 mg, 0.44 mmol), and the mixture was stirred for 36 h under positive pressure of O$_2$. The mixture was partitioned between EtOAc and brine. The organic layer was dried (Na$_2$SO$_4$), evaporated, and chromatographed on a silica gel column (hexane/EtOAc=5/1) to give 5 (3.13 g, 88%) as a white solid.

$^1$HNMR (CDCl$_3$) δ: 0.97 (9H, s, SiBu-t), 2.99-3.05 (1H, m, CH$_2$), 3.21-3.26 (1H, m, CH$_2$), 3.66 (3H, s, Me), 3.98 (1H, d, J=10.0 Hz, CH$_2$OSi), 4.18 ((1H, d, J=10.0 Hz, CH$_2$OSi), 6.24-6.26 (1H, m, CH=CH), 7.37-7.45 (6H, m, Ph), 7.58-7.62 (4H, m, Ph), 7.86-7.88 (1H, m, CH=CH).

1-(tert-Butyldiphenylsilyloxymethyl)-(trans-2-acetoxy)cyclopent-3-enecarboxylic acid methyl ester (6 of FIG. 6)

A mixture of NaBH$_4$ (628 mg, 16.6 mmol) and MeOH (50 ml) was cooled and stirred at −70° C. To this was added a mixture of 5 (3.39 g, 8.3 mmol) and CeCl$_3$.7H$_2$O (3.1 g, 8.3 mmol) in THF/MeOH=1/1 (50 ml) dropwise over 15 min. The resulting suspension was stirred for 1 h at the −70□. The reaction was quenched by adding AcOH (ca. 1 mL). The reaction mixture was evaporated. The residue was suspended in MeCN (15 ml). To this suspension were added DMAP (1.02 g, 8.3 mmol), i-Pr$_2$NEt (1.45 mL, 8.3 mmol) and Ac$_2$O (1.57 mL, 16.6 mmol). The mixture was stirred for 30 min at 0° under positive pressure of dry Ar, and partitioned between $CH_2Cl_2$ and sat. aqueous $NaHCO_3$. The organic layer was dried ($Na_2SO_4$), evaporated, and chromatographed on a silica gel column (hexane/EtOAc=4/1). This gave 6 (3.74 g, 100%) as an oil.

$^1$HNMR ($CDCl_3$) δ: 1.02 (9H, s, SiBu-t), 1.87 (3H, s, Ac), 2.50-2.55 (1H, m, $CH_2$), 2.91-2.97 (1H, m, $CH_2$), 3.71 (3H, s, Me), 3.87 (1H, d, J=9.6 Hz, $CH_2OSi$), 4.08 (1H, d, J=9.6 Hz, $CH_2OSi$), 5.76-5.78 (1H, m, CH=CH), 5.99-6.00 (1H, m, CH=CH), 6.07-6.08 (1H, m, AcOCH), 7.29-7.45 (4H, m, Ph), 7.61-7.65 (4H, m, Ph).

1-(tert-Butyldiphenylsilyloxymethyl)-(trans-4-hydroxy)cyclopent-2-enecarboxylic acid methyl ester (7 of FIG. 6)

A mixture of 6 (1.87 g, 4.13 mmol), $PdCl_2$ $(MeCN)_2$ (106 mg, 0.41 mmol) and p-quinone 224 mg, 2.07 mmol) in THF (17 mL) was refluxed for 3 h under positive pressure of dry Ar. The mixture was partitioned between $CH_2Cl_2$ and sat. aqueous $Na_2S_2O_3$. The organic layer was dried ($Na_2SO_4$), evaporated. The residue was dissolved in MeOH (5 ml) and treated with $K_2CO_3$ (685 mg, 4.96 mmol) for 1 h with stirring. The mixture was partitioned between $CHCl_3$ and brine. The organic layer was dried ($Na_2SO_4$), evaporated, and chromatographed on a silica gel column (hexane/EtOAc=6/1). This gave 7 (1.14 g, 67%) as an oil.

$^1$HNMR ($CDCl_3$) δ: 1.02 (9H, s, SiBu-t), 1.87 (1H, dd, J=14.4 and 2.4 Hz, $CH_2$), 2.73 (1H, dd, J=14.4 and 7.2 Hz, $CH_2$), 3.65 (3H, s, Me), 3.79 (1H, d, J=9.6 Hz, $CH_2OSi$), 3.85 (1H, d, J=9.6 Hz, $CH_2OSi$), 4.82-4.87 (1H, m, CHOH), 5.84-5.87 (1H, m, CH=CH), 6.02-6.04 (1H, m, CH=CH), 7.38-7.44 (6H, m, Ph), 7.63-7.65 (4H, m, Ph).

1-(tert-Butyldiphenylsilyloxymethyl)-(cis-4-hydroxy)cyclopent-2-enecarboxylic acid methyl ester (8 of FIG. 6)

A mixture of 7 (1.08 g, 2.63 mmol), $Ph_3P$ (897 mg, 3.42 mmol) and AcOH (301 μL, 5.26 mmol) in THF (10 mL) was cooled to 0 under positive pressure of dry Ar. To this was added dropwise diethyl azodicarboxylate (2.3 M solution in toluene, 1.49 mL, 3.42 mol). After stirring for 30 min, the mixture was partitioned between $CH_2Cl_2$ and sat. aqueous $NaHCO_3$. The organic layer was dried ($Na_2SO_4$) and evaporated. The residue was treated with $K_2CO_3$ (727 mg, 5.26 mmol) in MeOH (5 mL) for 1 h. The mixture was partitioned between $CHCl_3$ and brine. The organic layer was dried ($Na_2SO_4$), evaporated, and chromatographed on a silica gel column (hexane/EtOAc=4/1). This gave 8 (892 mg, 83%) as an oil.

$^1$HNMR ($CDCl_3$) δ: 1.02 (9H, s, SiBu-t), 2.20-2.31 (3H, m, $CH_2$ and OH), 3.70 (1H, d, J=9.6 Hz, $CH_2OSi$), 3.71 (3H, s, Me), 3.87 (1H, d, J=9.6 Hz, $CH_2OSi$), 4.76-4.81 (1H, m, CHOH), 5.88 (1H, d, J=5.6 Hz, CH=CH), 6.03 (1H, dd, J=5.6 and 2.4 Hz, CH=CH), 7.36-7.46 (6H, m, Ph), 7.61-7.65 (4H, m, Ph).

1-[cis-4-(tert-Butyldiphenylsilyloxymethyl)-trans-4-methoxycarbonylcyclopent-2-en-1-yl]thymine (9 of FIG. 6)

To a THF (25 mL) solution of $PPh_3$ (2.28 g, 8.68 mmol) was added dropwise diethyl azodicarboxylate (2.3 M solution in toluene, 3.63 mL, 8.35 mol) at 0° under positive pressure of dry Ar. After stirring for 30 min, a THF (76 mL) suspension containing 8 (1.37 g, 3.34 mmol) and $N^3$-benzoylthymine (1.15 g, 5.01 mmol) was added dropwise. The mixture was stirred for 70 h at room temperature, evaporated, and then treated with 2 M NaOMe in MeOH (6.7 mL) for 2 h. Neutralization of the reaction mixture with AcOH (1.15 mL) was followed by partition between $CH_2Cl_2$ and sat. aqueous $NaHCO_3$. The organic layer was dried ($Na_2SO_4$), evaporated, and chromatographed on a silica gel column (hexane/EtOAc=1/1). This gave 9 (1.21 g, 70%) as a white foam.

$^1$HNMR ($CDCl_3$) δ: 1.05 (9H, s, SiBu-t), 1.74 (3H, d, J=1.2 Hz, thymine-5-Me), 1.75 (1H, dd, J=14.0 and 6.8 Hz, $CH_2$), 3.01 (1H, dd, J=14.0 and 8.4 Hz, $CH_2$), 3.70 (3H, s, Me), 3.87 (1H, d, J=10.0 Hz, $CH_2OSi$), 3.90 (1H, d, J=10.0 Hz, $CH_2OSi$), 5.79 (1H, dd, J=5.2 and 2.0 Hz, CH=CH), 5.83-5.88 (1H, m, CHN), 6.10 (1H, dd, J=5.2 and 2.4 Hz, CH=CH), 6.88 (1H, q, J=1.2 Hz, thymine-H-6), 4.36-7.47 (6H, m, Ph), 7.61-7.64 (4H, m, Ph), 8.89 (1H, br, thymine-NH).

1-[cis-4-(tert-Butyldiphenylsilyloxymethyl)-trans-4-ethynylcyclopent-2-en-1-yl]thymine (10 of FIG. 6)

To a $CH_2Cl_2$ (10 mL) solution of 9 (550 mg, 1.06 mmol) was added dropwise i-$Bu_2AlH$ (1.01 M in toluene, 1.16 mL, 1.17 mmol) at −70° C. under positive pressure of dry Ar. After stirring for 20 min, an additional i-$Bu_2AlH$ (2.32 mL, 2.34 mmol) and added, and stirring was continued for further 20 min. Quenching with AcOH (200 mL) was followed by evaporation. Short silica gel column chromatography (hexane/EtOAc=1/5) gave the trans-4-hydroxymethyl derivative (294 mg). The trans-4-hydroxymethyl derivative was dissolved in $CH_2Cl_2$ (10 mL), and oxidized with Dess-Martin periodinane (477 mg, 1.12 mmol). After stirring for 1.5 h, the mixture was partitioned between $CH_2Cl_2$ and sat. aqueous $NaHCO_3$. The organic layer was dried ($Na_2SO_4$) and evaporated to give a crude trans-4-aldehyde (274 mg). The aldehyde was dissolved in MeOH containing $K_2CO_3$ (310 mg, 2.24 mmol), and stirred for 10 min at 0° under positive pressure of dry Ar. To this was added dimethyl(1-diazo-2-oxopropyl)phosphonate* (270 mg, 1.4 mmol). The mixture was stirred for 1 h, and then partitioned between EtOAc and sat. aqueous $NaHCO_3$. The organic layer was dried ($Na_2SO_4$), evaporated, and chromatographed on a silica gel column (hexane/EtOAc=1/1). This gave 10 (138 mg, 27%) as a white foam.

*For the preparation of this reagent, see: P. Callant, L. D'Haenes, and M. Vandewalle, Synth. Commun., 14, 155-161 (1984).

*The use of this reagent for the conversion of RCHO to RC=CH:I. Gillaizeau, I. M. Lagoja, S. P. Nolan, V. Aucagne, J. Rozenski, P. Herdewijn, and L. A. Agrofoglio, Eur. J. Org. Chem., 666-671 (2003).

$^1$HNMR ($CDCl_3$) δ: 1.07 (9H, s, SiBu-t), 1.71 (3H, d, J=1.2 Hz, thymine-5-Me), 2.02 (1H, dd, J=13.2 and 7.6 Hz, $CH_2$), 2.20 (1H, s, C≡CH), 2.70 (1H, dd, J=13.2 and 8.0 Hz, $CH_2$), 3.69 (1H, d, J=9.6 Hz, $CH_2OSi$), 3.83 (1H, d, J=9.6 Hz, $CH_2OSi$), 5.76 (1H, dd, J=5.2 and 2.0 Hz, CH=CH), 5.91-5.95 (1H, m, CHN), 6.02 (1H, dd, J=5.2 and 2.4 Hz, CH=CH), 6.98 (1H, q, J=1.2 Hz, thymine-H-6), 7.37-7.48 (6H, m, Ph), 7.63-7.66 (4H, m, Ph), 8.20 (1H, br, thymine-NH).

FAB-MS (m/z): 485 ($M^+$+H).

1-(cis-4-Hydroxymethyl-trans-4-ethynylcyclopent-2-en-1-yl)thymine (11, FIG. 6): KMA-23-153

A mixture of 10 (101 mg, 0.21 mmol) and $Bu_4NF$ (1M solution in THF, 230 μL, 0.23 mmol) in THF (3 mL) was stirred for 2 h at room temperature. To this mixture were added 4-dimethylaminopyridine (51 mg, 0.42 mmol), i-$Pr_2NEt$ (73 μL, 0.42 mmol), and $Ac_2O$ (80 μL, 0.84 mmol).

The reaction mixture was stirred for 30 min, and then partitioned between $CH_2Cl_2$ and sat. aqueous $NaHCO_3$. The organic layer was dried ($Na_2SO_4$), evaporated, and chromatographed on a silica gel column (AcOEt). This gave the acetate (52 mg) as a white solid. This acetate was treated with $NH_3$/MeOH (35 ml) below 0° C. for 12 h. During evaporation of the solvent, precipitation occurred. The precipitate was washed with hot benzene (50 ml) to give an analytically pure 11 (31 mg, 60%).

$^1$HNMR ($CDCl_3$) δ: 1.96-1.94 (5H, m, $CH_2$, OH and thymine-5-Me), 2.30 (1H, s, C≡CH), 2.81 (1H, dd, J=13.6 and 8.8 Hz, $CH_2$), 3.65 (1H, dd, J=10.0 and 7.6 Hz, $CH_2OH$), 3.78 (1H, dd, J=10.0 and 4.8 Hz, $CH_2OH$), 5.78-5.80 (1H, m, CH=CH), 5.85-5.89 (1H, m, CHN), 6.04-6.06 (1H, m, CH=CH), 7.10 (1H, q, J=1.2 Hz, thymine-H-6), 8.09 (1H, br, thymine-NH). Anal. Calcd for $C_{13}H_{14}N_2O_3 \cdot \frac{1}{5}H_2O$: C, 62.49; H, 5.81; N, 11.21. Found: C, 62.57; H, 5.65; N, 11.22.

Biological Activity
Methods and Materials:

Chemicals: The 4'-D4T analogs (FIG. 1) were synthesized in the laboratory of Dr. Hiromichi Tanaka, School of Pharmaceutical Sciences, Showa University, Japan. The dThd, D4T and AZT were purchased from Sigma-Aldrich Corp. St. Louis, Mo. The ddI was purchased from ICN Biochemicals Inc., Aurora, Ohio. The 3TC was received from Triangle Pharmaceuticals, Durham, N.C. The LFd4C was received from Vion Inc., New Haven, Conn. All other chemicals used were of reagent grade or higher.

Cell lines and virus: Both the H9 cell line, used for toxicity studies and virus propagation, and the MT-2 cell line, used for the antiviral activity studies were received from the AIDS Research and Reference Reagent Program of the National Institutes of Health and were contributed by Dr. Robert Gallo and Dr. Douglas Richman respectively. The HIV-1 strain IIIB was received from Dr. John Mellors.

Determination of antiviral activity: Compounds were tested in MT-2 cells infected with HIV-1 strain IIIB essentially as described previously (31). Briefly, serial dilutions of drugs are placed in triplicate wells of a 96 well tissue culture plate, then MT-2 cells grown in RPMI 1640 media supplemented with 10% dialyzed fetal bovine serum and 100 µg/ml kanamycin are added at $10^4$ cells/100 µl plus and minus 0.1 m.o.i. of HIV-1 IIIB. Five days later MTT dye is added to the wells and the color of the tetrazolium dye measured at 595 nm was used to quantitate the cellular viability (20). Calculations of the percent protection and isobologram combination studies are described (12).

Cellular Toxicity of Nucleoside Analogs:

These dThd analogs have been evaluated in several cell lines; H9, CEM, MT-2 and HepG2. The basic procedures are similar. The cells are seeded a low concentration, then serial dilutions of test compound are added. The CEM, MT-2 and H9 cell lines we use are grown in RPMI 1640 supplemented with 10% dialyzed fetal bovine serum and 10 µg/ml kanamycin. After 48 to 96 h incubation at 37° C. in a 5% $CO_2$ humidified incubator the assay is ended. The drug treated samples are compared to the untreated controls. This is accomplished in suspension cell lines by counting cell numbers either with a hemocytometer or by using a Coulter Counter. The HepG2 cells, a human hepatoma cell line, were grown in DMEM medium supplemented with 10% dialyzed fetal bovine serum and 10 µg/ml kanamycin. The effect on HepG2, a monolayer cell line, was quantified by staining with 1.0% methylene blue dye dissolved in 50% ethanol, after decanting the growth medium. The cell layer is then solubilized in a 5% sarkosyl solution and the resulting color is measured at 595 nm on a Molecular Devices model Vmax plate reading spectrophotometer (Menlo Park, Calif.). The color of the untreated controls is compared to the drug treated samples.

Mitochondrial DNA:

The effect of nucleoside analogs on mtDNA content was assessed as described previously (2). Briefly, CEM cells maintained in RPMI 1640 supplemented with 10% dialyzed fetal bovine serum were plated at $2 \times 10^5$/ml into a 24 well tissue culture plate. Cells treated with drugs at various concentrations either as single agents or in combination were grown for four days. Cells were then harvested, treated with proteinase K and DNase free RNase. Extracts were applied to nylon membranes and hybridized with an mtDNA probe. After stripping the membrane the load was normalized by rehybridizing the membrane with an Alu probe. Blots were quantitated with a Molecular Dynamics personal densitometer SI with ImageQuaNT analysis software.

Monophosphorylation of Analogs by Thymidine Kinase:

All the analogs were tested for their ability to be phosphorylated by thymidine kinase (TK-1) from CEM cells. This enzyme was purified by an affinity column technique developed in this laboratory (7). Thymidine analogs (250 uM) were incubated in a mixture that contained 150 mM Tris HCl pH 7.5, 2.4 mM ATP, 2.4 mM MgCl2, 0.6 mgs creatine phosphate, 5.8 units of creatine phosphokinase, 0.19 mgs albumin and 0.07 units of TK-1 in a total volume of 200 ul. At the end of the incubation time the reaction was stopped by the addition of 3 parts cold HPLC grade methanol. After incubating on ice for at least 10 min. the methanol insoluble material is precipitated by centrifugation and the methanol soluble supernatants were placed into clean microfuge tubes. These samples were brought to dryness in a Speedvac Centrifuge. The samples were dissolved in water and separated on a Shimatzu HPLC model SCL 10Avp using a gradient of water to 300 mM potassium phosphate and a Whatman 10/25 particle SAX column. Km and relative Vmax studies were done in a similar fashion, using the same mixture and different amounts of substrate and enzyme.

Acid Stability Studies:

Nucleoside samples were mixed with 1N HCl and incubated at 37° C. for 2.5 h. Then the samples were examined by HPLC using a Bechman ODS column employing a gradient of water to 80% methanol.

Thymidine Phosphorylase Assays:

Nucleoside analogs (100 µM) were incubated in 75 mM potassium phosphate buffer pH 7.3 at 37° C. using a partially purified preparation of human liver extract (28) as a source of the thymidine phosphorylase (TP). After incubation, the reaction was stopped by the addition of trichloroacetic acid to a final concentration of 15%. The samples were then incubated on ice. After the acid insoluble components were removed by centrifugation, the supernatant was neutralized by two extractions with one half volume of trioctylamine/freon (45:55). The aqueous supernatants were examined by HPLC using the Beckman ODS column method, as described in Acid Stability Studies.

Thymidine Kinase Assays:

The thymidine kinase assays were the same as that described previously (21). Briefly, the assay uses [$^{14}$C]-dThd (100 µM, 6.7 mCi/mmol) in a mixture that contains 2.4 mM ATP-Mg, 156 mM Tris-HCl pH 7.5, 0.23 mg creatine phosphate, 7 µg creatine phospho kinase, 67 µg BSA and 1.9 mM DTT in a 75 µl volume. The reactions were incubated for various amounts of time, then they were terminated by spotting 50 µl aliquots onto DE-81 anion exchange discs (Whatman Inc., Clifton, N.J.) that was immersed immediately in 95% ethanol. After two additional washes in ethanol, the discs were dried and placed in scintillation vials that contained 5 ml SafeScint Scintillation Cocktail (American Bioanalytical, Natick, Mass.). The amount of radioactivity, which represents the amount of dTMP formed, was quantitated in a Beckman LS5000TD Scintillation Counter (Beckman Instruments Inc., Palo Alto, Calif.).

Figure 8:
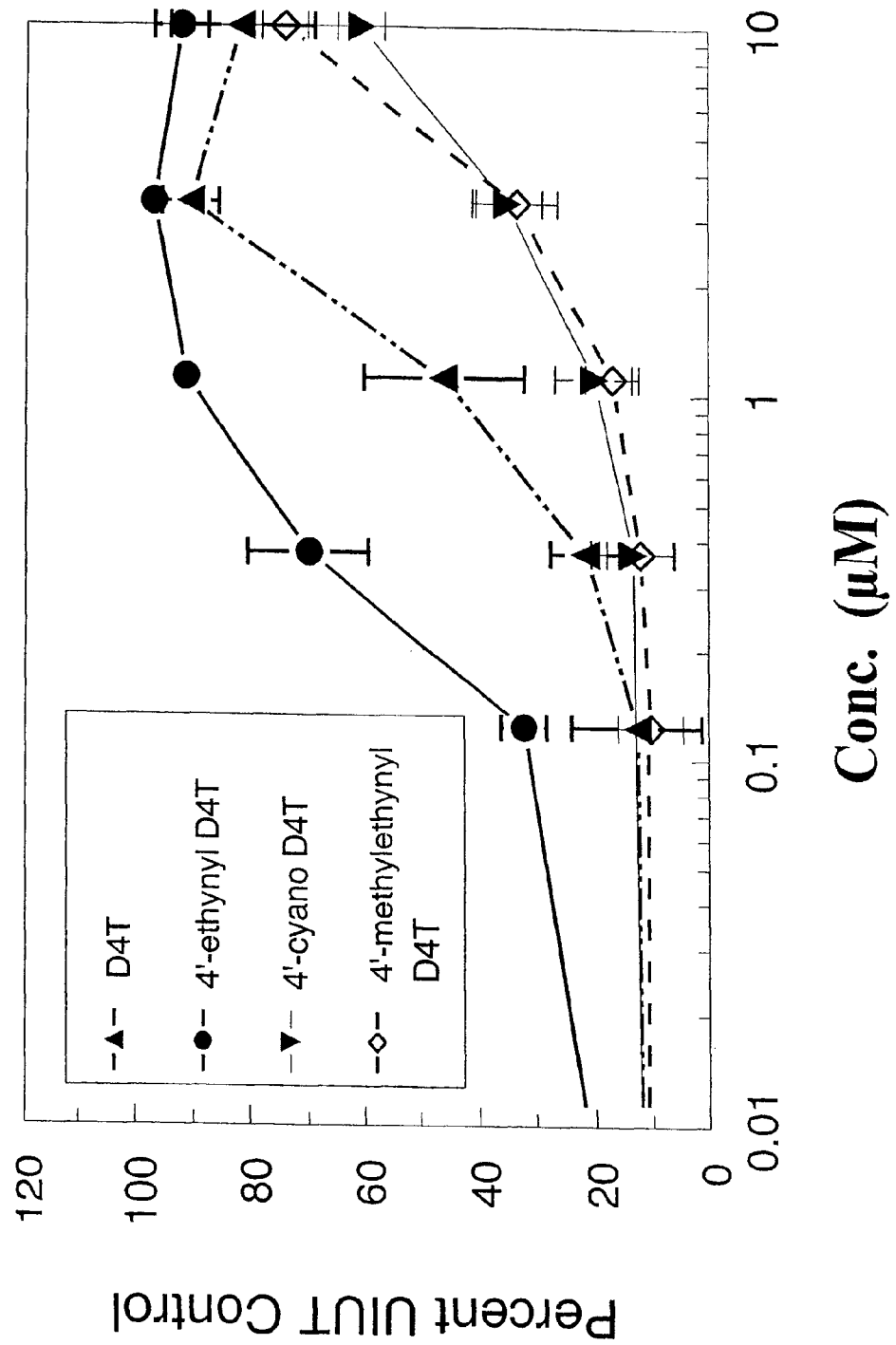
FIG. 8 shows the anti-HIV Activity of 4'Substituted D4T analogs: the anti viral activity of 4'-ethynyl D4T, D4T, 4'-ethynylmethly D4T and 4'-cyano D4T were determined in the MT-2/HIV IIIB system as describe in the Material and Methods section in the examples. Inhibition is determined by comparison of readings at O.D. 595 nm to that of uninfected untreated (UIUT) control MT-2 cells.

Results of Biological Activity:

Antiviral Effect of 4'-Substituted D4T Analogs:

Experiments were performed in the MT-2/IIIB anti HIV-1 system by adding compounds substituted at the 4' position of D4T with a methyl, vinyl, ethynyl, ethynylmethyl, ethynylchloro, allyl or cyano group (FIG. 1). The results indicated that the 4'-ethynyl analog was more effective against HIV and less toxic than the parental compound D4T. Whereas, 4'-cyano D4T and 4'-ethynylmethyl D4T were less active than D4T against HIV (FIG. 8) The 4'-methyl, 4'-vinyl, 4'-ethynylchloro and 4'-allyl substituted D4T analogs did not achieve a $EC_{50}$ at a concentration of 100 μM. A summary of the $EC_{50}$ against HIV of these compounds together with D4T is shown in Table 1, below.

TABLE 1

The Effect of 4'-Substituted D4T Analogs on HIV.

| Compound | $EC_{50}$ (μM)[a] | $ID_{50}$ (μM)[b] |
|---|---|---|
| D4T | 1.3 ± 0.4 | 98.0 ±10.8 |
| 4'-methyl D4T | >100[d] | >100 |
| 4'-vinyl D4T | >100[d] | >100 |
| 4'-ethynyl D4T | 0.25 ± 0.14[d] | >256[c] |
| 4'-ethynylmethyl D4T | 4.0 ± 1.6 | >100 |
| 4'-ethynylchloro D4T | >100 | 63.3 ± 20.8 |
| 4'-allyl D4T | >100 | >100 |
| 4'-cyano D4T | 7.0 ± 2.6 | >100 |

[a]Effective concentration required to achieve 50% protection from HIV in MT-2 cells.
[b]Concentration required to inhibit MT-2 cell growth by 50%.
[c]The highest concentration tested.
[d]$EC_{50}$ reported previously (17).

Figure 9:
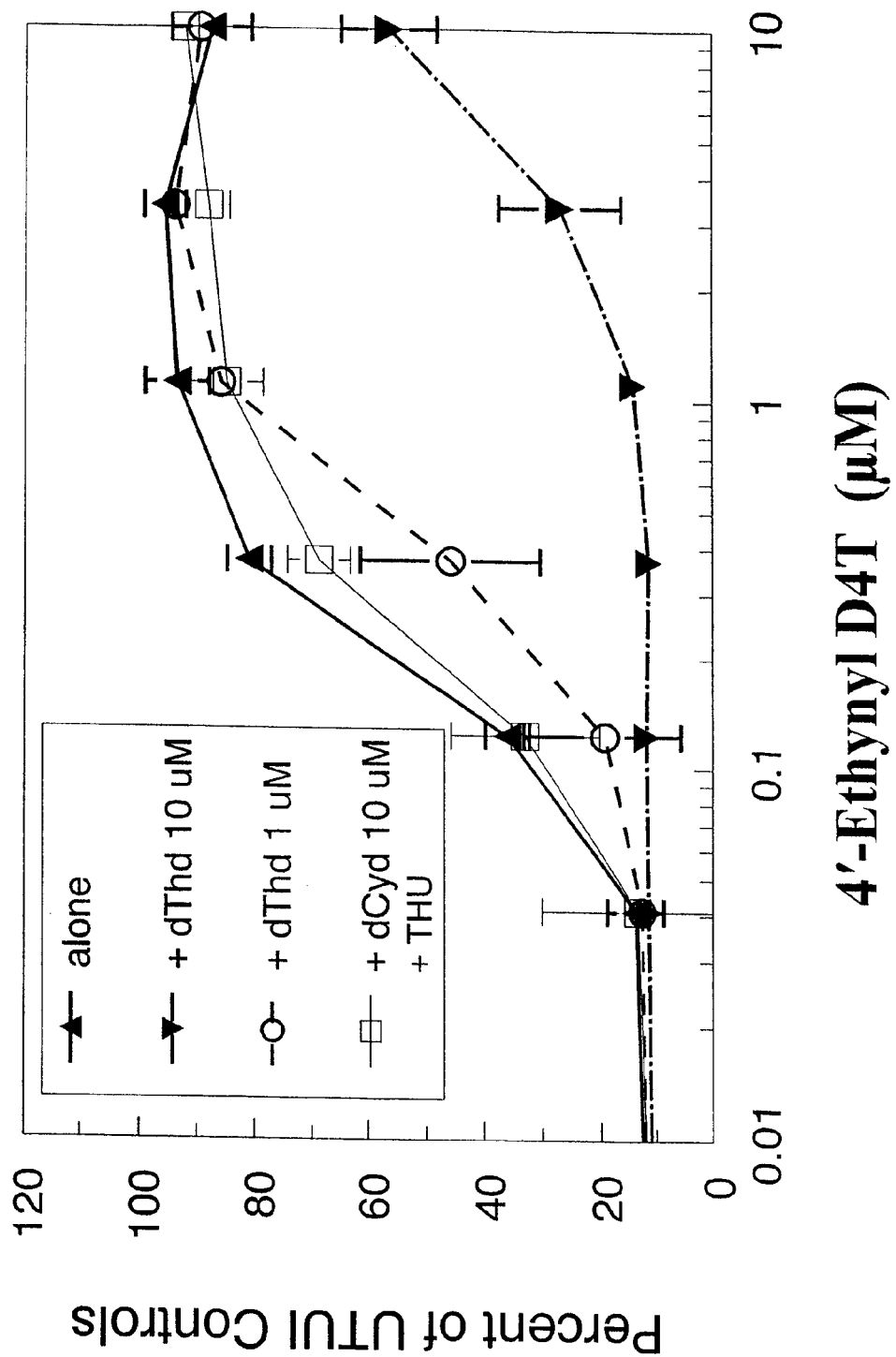
FIG. 9 shows the reversal of the Anti-HIV effect of 4'-ethynyl D4T. dThd (10 μM), dThd (1 μM) and dCyd (10 μM) in the presence of THU (5 μM) were added to the standard antiviral assay. Inhibition is determined by comparison of readings at O.D. 595 nm to that of uninfected untreated (UIUT) control MT-2 cells.

To determine whether 4'-ethynyl D4T acts as a dThd analog against HIV, the effect of the addition of dThd or dCyd on the antiviral activity of 4'-ethynyl D4T was examined. To prevent the possibility that dCyd could be deaminated to dUrd in cells, a cytidine deaminase inhibitor, tetrahydro uridine, at a nontoxic level, was also added. It was observed that dThd decreased the antiviral effect of 4'-ethynyl D4T in a concentration dependent manner. However, dCyd had no significant effect on the activity of 4'-ethynyl D4T against HIV (FIG. 9).

Figure 10:
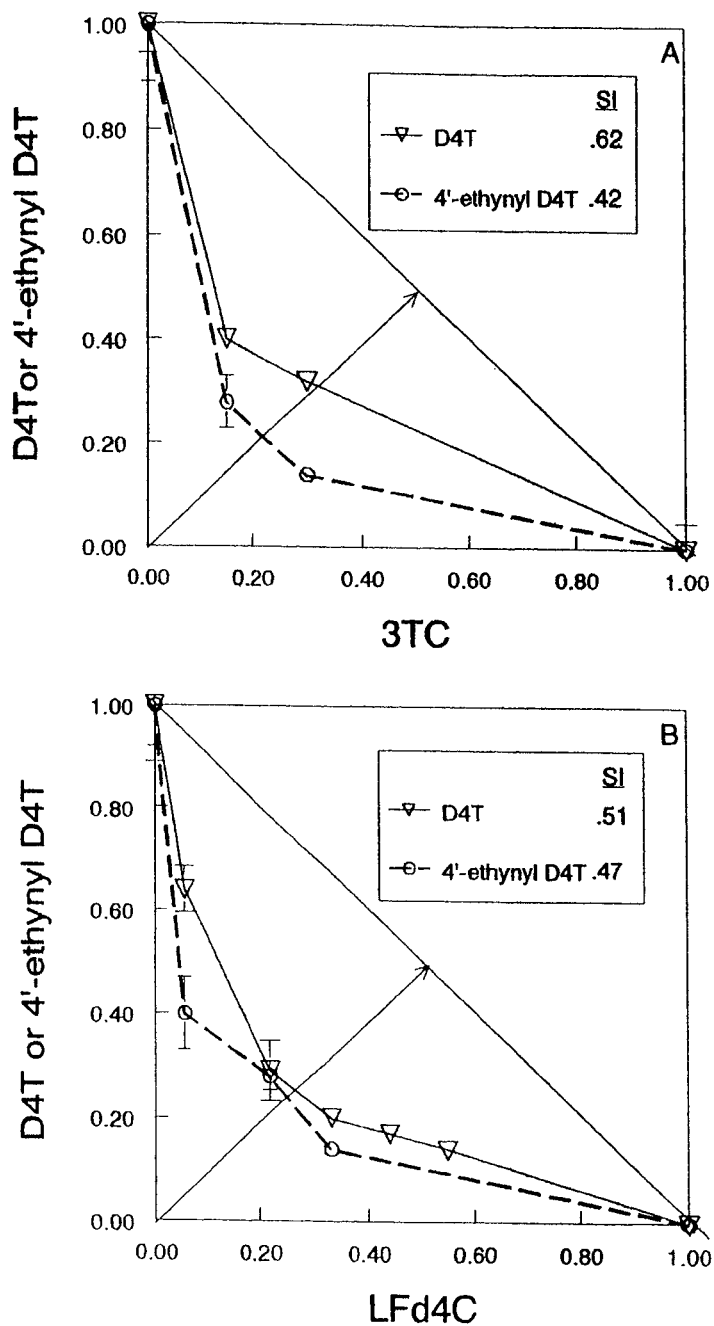
FIG. 10 shows antiviral isobolograms of D4T and 4'-ethynyl D4T in combination with: A) 3TC and B) LFd4C data obtained in the MT-2/HIV IIIB system. The numbers along each axis are proportions of the $EC_{50}$ (taken as 1) for the drug indicated as a single agent. [$EC_{50}$ for single agents are 1.4 μM D4T, 0.5 μM 4'-ethynyl D4T, 1.0 μM 3TC and 0.18 μM LFd4C] Each datum point represents a combination that produces an effect equivalent to that of the $EC_{50}$ for either drug alone. Synergy Index (SI) is calculated as the fractional part of the 45° line to the line indicating that the drug interaction is additive, the total distance being 1.0.

To assess its interaction with other antiviral nucleoside analogs the antiviral isobolograms of 4'ethynyl D4T in combination with 3TC, LFd4C, ddI and AZT were generated. 4' Ethynyl D4T was shown to have synergistic interactions with 3TC and LFd4C against HIV (FIG. 10), and the Synergy Index (SI) was determined by measuring the relative distance from the line indicating an additive drug effect. However, its antiviral effect with ddI and AZT was only additive (data not shown).

Cellular Toxicity:

The effect of the 4'-substituted D4T analogs on cell growth and mtDNA content was determined in CEM cells (Table 2a, set forth below). None of those analogs, with the exception of 4'-ethynylchloro D4T, could retard four day cell growth with an $ID_{50}$ less than 100 μM. Results of 72 h toxicity studies in HepG2 cells also showed that the $ID_{50}$ for D4T, 4'-vinyl D4T and 4'-ethynyl D4T was greater than 100 μM. 4'-Ethynyl D4T could decrease intracellular mitochondrial DNA with an $ID_{50}$ of 100 μM, which is 10 times higher concentration than that of D4T. In view of the synergistic interaction of 4'-ethynyl D4T with 3TC and LFd4C against HIV, the interaction of those compounds on cell growth was also assessed. In H9 cells during a 48 h assay no significant increase in toxic interactions was observed (Table 2b, below).

TABLE 2a

Toxicity of Nucleoside Analogs in CEM Cells.

| Compound | Cellular[a] $ID_{50}$ (μM) | Mitochondrial DNA Content[b] $ID_{50}$ (μM) |
|---|---|---|
| D4T | 60.0 ± 18.0 | 9.3 ± 1.4 |
| 4'-methyl D4T | >100 (114 ± 2) | — |
| 4'-vinyl D4T | >100 (78 ± 21) | — |
| 4'-ethynyl D4T | >100 (77 ± 16) | >100 (94 ± 4) |
| 4'-ethynylmethyl D4T | >100 (94 ± 20) | >100 (116 ± 26) |
| 4'-ethynylchloro D4T | 62.6 ± 10.0 | — |
| 4'-allyl D4T | >100 | — |
| 4'-cyano D4T | >100 (60 ± 1) | >100 (264 ± 23) |
| ddC | 5.5 ± 1.8 | 0.15 ± 0.12 |
| 3TC | >200 (77 ± 28) | >200 (114 ± 2) |

Procedures described in Materials and Methods:
[a]Toxicity determined by cell counts compared to untreated controls.
[b]Mitochondrial DNA content determined by Southern Blot analysis and densitometer readings compared to that of untreated CEM control cells. The numbers are means of μM concentrations and standard deviations that cause 50% inhibition of control cells. The numbers in parentheses represent the mean and standard deviations of percentage of untreated CEM control cells at the concentration indicated.

TABLE 2b

Toxicity of 4'-ethynyl D4T in H-9 Cells Alone and in Combination with Other Anti-HIV Compounds as Percent of Untreated Controls.*

| | Conc. of 4'-ethynyl D4T (μM) | | |
|---|---|---|---|
| | 0 | 25 | 50 |
| No additive | 100 ± 5 | 97 ± 7 | 102 ± 6 |
| Plus LFd4C (μM) | | | |
| 5 | 73 ± 9 | 62 ± 3 | 72 ± 5 |
| 10 | 56 ± 4 | 58 ± 4 | 64 ± 5 |
| Plus 3TC (μM) | | | |
| 5 | 99 ± 3 | 98 ± 2 | 99 ± 10 |
| 20 | 94 ± 3 | 88 ± 3 | 87 ± 6 |
| 100 | 108 ± 12 | 85 ± 3 | 84 ± 6 |

*H-9 cells were grown as described in Materials and Methods for 48 h in the presence of single compounds or in combination. Three or more wells were counted in duplicate for each condition using a Coulter Counter. Numbers represent means and standard deviations.

Interaction of 4'-Substituted D4T Analogs with TK-1:

The potential of these compounds to be phosphorylated by purified human TK-1 was assessed (Table 3a, below). AZT was converted to the monophoshate form half as fast as dThd, while the rate of 4'-methyl D4T, and 4'-vinyl D4T are similar to the rate of D4T (approximately 2 percent of dThd). The conversion rate of 4'-ethynyl D4T was superior to D4T with a confidence level of 0.06. There was no significant difference in the phosphorylation rates of 4'-ethynyl D4T and 4'-ethynylchloro D4T with a confidence level of 0.91 using a two tailed test. The Km of 4'-ethynyl D4T was assessed to be 52 μM, which is lower than 133 μM for D4T but higher than dThd. To be sure that none of these dThd analogs act as a potent inhibitor of TK-1, even if they are not substrates, dThd, AZT, D4T, and the 4'-substituted analogs of D4T were added to a thymidine kinase assay at a concentration 10 fold higher than that of the [$^{14}$C]-dThd, then the amount of conversion to [$^{14}$C]-dTMP was compared to reactions with no additions (Table 3b, below). Compounds that are phosphorylated well by TK-1 such as AZT can affect the amount of phosphorylayed dThd. The addition of D4T or its analogs that are poorly phosphorylated, even in a 10 fold excess have less effect than AZT on [$^{14}$C]-dThd phosphorylation by TK-1.

TABLE 3a

Phosphorylation by Human Cytoplasmic Thymidine Kinase

| Compound | Km (μM) | Relative Vmax |
|---|---|---|
| dThd | 2.6* | 100 |
| AZT | — | 55.5 ± 9.7 |
| D4T | 133 | 2.1 ± 0.7 |
| 4'-methyl D4T | — | 1.6 ± 0.5 |
| 4'-vinyl D4T | — | 1.8 ± 0.5 |
| 4'-ethynyl D4T | 52 | 3.8 ± 0.8 |
| 4'-ethynylmethyl D4T | — | 2.5 ± 0.9 |
| 4'-ethynylchloro D4T | — | 3.9 ± 1.0 |
| 4'-allyl D4T | — | 0.4 ± 0.2 |
| 4'-cyano D4T | — | 1.1 ± 0.2 |

250 μM dThd or analog and 2.4 mM ATP were incubated with 0.07 unit of TK-1 at 37° C. for 285 min. Value published previously (21).

TABLE 3b

Effect of the Addition of Thymidine Analogs to a Thymidine Kinase Assay.*

| Nucleoside added | Percent of Activity |
|---|---|
| — | 100 |
| dThd | 9.1 ± 3.2 |
| AZT | 5.4 ± 2.3 |
| D4T | 106.3 ± 7.7 |
| 4'-methyl D4T | 103.8 ± 9.9 |
| 4'-vinyl D4T | 99.5 ± 6.9 |
| 4'-ethynyl D4T | 83.9 ± 6.1 |
| 4'-ethynylmethyl D4T | 74.0 ± 7.9 |
| 4'-ethynylchloro D4T | 53.2 ± 9.2 |
| 4'-allyl D4T | 110.8 ± 9.0 |
| 4'-cyano D4T | 71.8 ± 8.2 |

*The assays were performed essentially as described in Material and Methods except the [$^{14}$C]-dThd concentration in the assay was reduced to 25 μM and the concentration of the added nucleoside was 250 μM.

Figure 11:
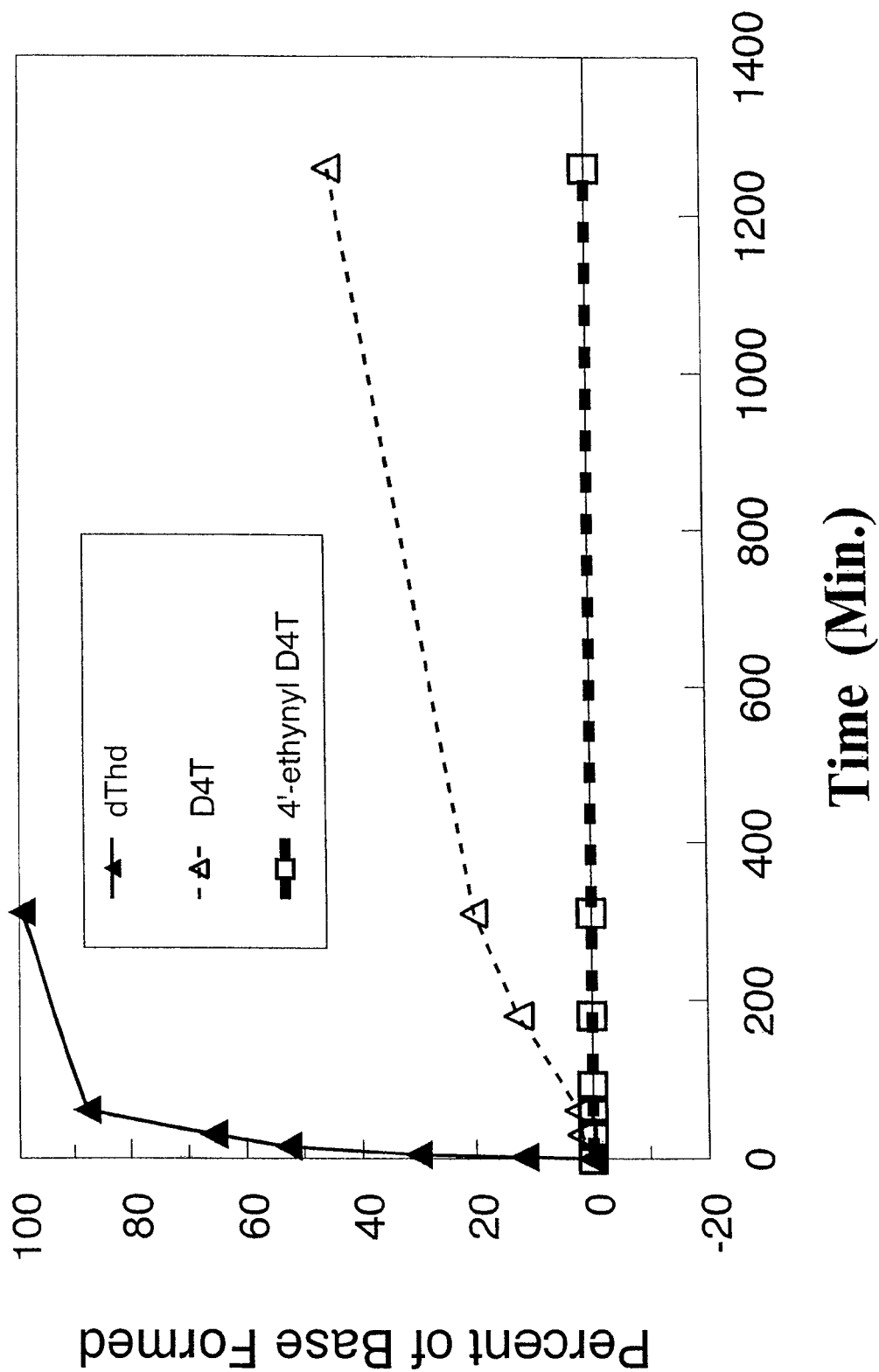
FIG. 11 shows thymidine phosphorylase treatment of D4T Analogs: dThd, D4T and 4'-ethynyl D4T were incubated with a partially purified preparation of TP from human liver extract. Then the ratio of base to nucleoside was determined by reverse phase HPLC on a Beckman ODS column as described in the materials and methods section.

Interaction with Thymidine Phosphorylase and Acid Stability of 4'-Ethynyl D4T:

Partially purified preparation of thymidine phosphorylase (TP) from human liver was utilized for these studies. dThd broke down very quickly while D4T was at least 10 times slower. The break down of 4'ethynyl D4T was below the detection level during the whole incubation period studied (FIG. 11). The stability of D4T and 4'-ethynyl D4T at pH 1 and at 37° C. was examined for 2.5 h. No detectable breakdown of either compound was detected.

Discussion:

D4T is an effective anti-HIV D-dideoxy-thymidine analog. Its limiting clinical toxicity, upon long term treatment, is peripheral neuropathy, which is associated with its action of decreasing the mitochrondrial DNA content of peripheral neurons (4, 5, 33, 34). The biochemical determinants of the action of D4T are different from those of 3TC, ddI or ddC. An analog of D4T, which has more potent anti-HIV activity and less impact on nuclear or mitochondrial DNA synthesis, could have better therapeutic effect than D4T and could substitute for D4T in anti-HIV combination therapy. Thus, the synthesis of D4T analogs with better pharmacological properties is a direction which has been taken in anti-HIV drug discovery. Among all the 4'-substituted D4T analogs, synthesized by us and others, 4'-ethynyl D4T is the most active one against HIV in culture. Maag et. al described a 4'-azido D4T that was inactive against HIV at non-toxic levels (29) and O-Yang et. al describe three 4'-substituted D4T analogs that were non-toxic and had no anti-HIV activity (32).

D4T is catabolized, rather quickly, into beta-aminoisobutyric acid and thymine by the hepatocytes of the liver (38). The enzyme responsible for this breakdown is TP, which in the presence of phosphate breaks dThd into thymine and 2-deoxy-D-ribose-1-phosphate. By incubating 4'-ethynyl D4T and D4T with a partially purified preparation of human liver TP, it was shown that 4'-ethynyl D4T was much more resistant to TP than D4T. This indicates that 4'-ethynyl has an additional advantage over D4T from a pharmacokinetic point of view. Furthermore, 4'-ethynyl D4T is also as stable as D4T in an acidic condition that mimics the stomach (data not shown). This suggests that 4'-ethynyl D4T could be an orally active agent like D4T. Detailed pharmacokinetic studies will be performed in the future. Since 4'-ethynyl D4T is more potent than D4T, it is conceivable that 4'-ethynyl D4T could have less viral drug resistance issues. When 4'-ethynyl D4T is employed at the same dosage as D4T to the patient, the viral load will be much less, thereby, decreasing the probable occurrence of resistant strains. It may also be possible to give 4'-ethynyl D4T at higher dosage than D4T, since 4'-ethynyl D4T is less inhibitory to cell growth and causes less mitochondrial DNA decrease than D4T. However, the determination of the amount of 4'-ethynyl D4T that can be safely used will require further investigation.

Monotherapy allows the development of resistant strains of virus to occur more readily than combination therapy. It is therefore necessary for an antiviral compound to work in conjunction with other approved antiviral drugs which have different biochemical determinants of drug resistance. If the compounds are synergistic, or at least additive, with respect to their antiviral activity, but not to their cytotoxic effect on the host cells, improved therapy can be achieved. Indeed, combination therapy for HIV has made tremendous progress in the management of AIDS and D4T is often used as one of the drugs in combination protocols. To assess the potential use of 4'-ethynyl D4T in combination therapy, we examined the interaction of this compound with four antiviral nucleoside analogs. 4'-Ethynyl D4T is synergistic with 3TC and LFd4C (FIG. 9) and additive with AZT and ddI (data not shown) with respect to the anti-HIV activity, but not to cytotoxicity (Table 2b). This suggests that 4'-ethynyl D4T could be a useful compound for combination therapy and could be useful against virus resistant to currently used nucleosides by increasing their effectiveness through a synergistic response. The activity of 4'-ethynyl D4T against virus resistant to other nucleoside analogs is currently being investigated.

The underlying mechanism that makes 4'-ethynyl D4T more active than the other 4'-substituted D4T analogs studied against HIV is not clear. Deoxynucleoside analogs typically are converted into 5'triphosphate metabolites that are substrates for viral DNA polymerases. Triphosphate metabolites of known anti-HIV dideoxy nucleosides interact preferentially with viral reverse transcriptase and act as chain terminators when they are incorporated into a DNA strand. The formation of the monophosphate metabolite is the first step in the process to become a triphosphate metabolite. The 4'-substituted D4T compounds, like D4T, are dThd analogs, so we used purified TK-1 to test whether it could phosphorylate these analogs to their respective monophosphate forms. The results showed that 4'-ethynyl D4T was phosphorylated twice as fast as D4T although at a much slower rate than that of dThd or AZT. It is interesting to note that the 4'-methyl D4T and 4'-vinyl D4T analogs were phosphorylated at the same rate as D4T, but neither had significant anti-HIV activity. Thus, it can be concluded that the lack of activity of some of these 4'-substituted D4T analogs against HIV is not due to their inability to be phosphorylated by TK-1. The phosphorylation of 4'-ethynyl D4T by TK-1 is an essential step, but is not sufficient to have antiviral activity. Since its antiviral effect could be neutralized by dThd but not dCyd, 4'-ethynyl D4T, like D4T, acts as a dThd analog but the antiviral mechanism of action of 4'-ethynyl D4T could still be quite different from that of D4T. Our unpublished results indicate that D4T could be more efficiently phosphorylated to the triphosphate metabolite than 4'-ethynyl D4T using a CEM cellular extract supplemented with partially purified TK-1 and recombinant human dTMP kinase. This raises the question of whether the 4'-ethynyl D4TMP is the active metabolite instead of 4'-ethynyl D4TTP and requires further investigation.

In conclusion, 4'-ethynyl D4T is more potent against HIV and less toxic than D4T in cell culture. It is expected to have pharmacokinetic advantages over D4T, since it is not a substrate of Thymidine Phosphorylase. Thus, 4'-ethynyl D4T shows excellent potential as a new anti-HIV drug.

It is to be understood by those skilled in the art that the foregoing description and examples are illustrative of practicing the present invention, but are in no way limiting. Variations of the detail presented herein may be made without departing from the spirit and scope of the present invention as defined by the following claims.

REFERENCES

1. August, E. M., M. E. Marongiu, T. S. Lin, and W. H. Prusoff. 1988. Initial studies on the cellular pharmacology of 3'-deoxythymidin-2'-ene (d4T): a potent and selective inhibitor of human immunodeficiency virus. *Biochem Pharmacol* 37:4419-22.
2. Bridges, E. G., G. E. Dutschman, E. A. Gullen, and Y. C. Cheng. 1996. Favorable interaction of beta-L(-) nucleoside analogues with clinically approved anti-HIV nucleoside analogues for the treatment of human immunodeficiency virus. *Biochem Pharmacol* 51:731-6.
3. Brinkman, K., H. J. ter Hofstede, D. M. Burger, J. A. Smeitink, and P. P. Koopmans. 1998. Adverse effects of reverse transcriptase inhibitors: mitochondrial toxicity as common pathway. *Aids* 12:1735-44.
4. Browne, M. J., K. H. Mayer, S. B. Chafee, M. N. Dudley, M. R. Posner, S. M. Steinberg, K. K. Graham, S. M. Geletko, S. H. Zinner, S. L. Denman, and et al. 1993. 2',3'-didehydro-3'-deoxythymidine (d4T) in patients with AIDS or AIDS-related complex: a phase I trial. *J Infect Dis* 167:21-9.
5. Chen, C. H., and Y. C. Cheng. 1989. Delayed cytotoxicity and selective loss of mitochondrial DNA in cells treated with the anti-human immunodeficiency virus compound 2',3'-dideoxycytidine. *J Biol Chem* 264:11934-7.
6. Chen, C. H., M. Vazquez-Padua, and Y. C. Cheng. 1991. Effect of anti-human immunodeficiency virus nucleoside analogs on mitochondrial DNA and its implication for delayed toxicity. *Mol Pharmacol* 39:625-8.
7. Cheng, Y. C. 1978. Thymidine Kinase from Blast Cells of Myelocytic Leukemia, p. 365-371, *Methods in Enzymology*, vol. LI. Academic Press, New York.
8. Coates, J. A., N. Cammack, H. J. Jenkinson, A. J. Jowett, M. I. Jowett, B. A. Pearson, C. R. Penn, P. L. Rouse, K. C. Viner, and J: M. Cameron. 1992. (-)-2'-deoxy-3'-thiacytidine is a potent, highly selective inhibitor of human immunodeficiency virus type 1 and type 2 replication in vitro. *Antimicrob Agents Chemother* 36:733-9.
9. Coates, J. A., N. Cammack, H. J. Jenkinson, I. M. Mutton, B. A. Pearson, R. Storer, J. M. Cameron, and C. R. Penn. 1992. The separated enantiomers of 2'-deoxy-3'-thiacytidine (BCH 189) both inhibit human immunodeficiency virus replication in vitro. *Antimicrob Agents Chemother* 36:202-5.
10. De Clercq, E. 1994. HIV resistance to reverse transcriptase inhibitors. *Biochem Pharmacol* 47:155-69.
11. Doong, S. L., C. H. Tsai, R. F. Schinazi, D. C. Liotta, and Y. C. Cheng. 1991. Inhibition of the replication of hepatitis B virus in vitro by 2',3'-dideoxy-3'-thiacytidine and related analogues. *Proc Natl Acad Sci* USA 88:8495-9.
12. Dutschman, G. E., E. G. Bridges, S. H. Liu, E. Gullen, X. Guo, M. Kukhanova, and Y. C. Cheng. 1998. Metabolism of 2',3'-dideoxy-2',3'-didehydro-beta-L(-)-5-fluorocytidine and its activity in combination with clinically approved anti-human immunodeficiency virus beta-D(+) nucleoside analogs in vitro. *Antimicrob Agents Chemother* 42:1799-804.
13. Feng, J. Y., A. A. Johnson, K. A. Johnson, and K. S. Anderson. 2001. Insights into the molecular mechanism of mitochondrial toxicity by AIDS drugs. *J Biol Chem* 276:23832-7.
14. Gelmon, K., J. S. Montaner, M. Fanning, J. R. Smith, J. Falutz, C. Tsoukas, J. Gill, G. Wells, M. O'Shaughnessy, M. Wainberg, and et al. 1989. Nature, time course and dose dependence of zidovudine-related side effects: results from the Multicenter Canadian Azidothymidine Trial. *Aids* 3:555-61.
15. Gosselin, G., R. F. Schinazi, J. P. Sommadossi, C. Mathe, M. C. Bergogne, A. M. Aubertin, A. Kirn, and J. L. Imbach. 1994. Anti-human immunodeficiency virus activities of the beta-L enantiomer of 2',3'-dideoxycytidine and its 5-fluoro derivative in vitro. *Antimicrob Agents Chemother* 38:1292-7.
16. Hamamoto, Y., H. Nakashima, T. Matsui, A. Matsuda, T. Ueda, and N. Yamamoto.
1987. Inhibitory effect of 2',3'-didehydro-2',3'-dideoxynucleosides on infectivity, cytopathic effects, and replication of human immunodeficiency virus. *Antimicrob Agents Chemother* 31:907-10.
17. Haraguchi, K., S. Takeda, H. Tanaka, T. Nitanda, M. Baba, G. E. Dutschman, and Y. C. Cheng. 2003. Synthesis of a Highly Active New Anti-HIV Agent 2',3'-Didehydro-3'deoxy-4'-ethynylthymidine. *Bioorg Med Chem Setter* 13:3775-3777.
18. Johnson, A. A., A. S. Ray, J. Hanes, Z. Suo, J. M. Colacino, K. S. Anderson, and K. A. Johnson. 2001. Toxicity of antiviral nucleoside analogs and the human mitochondrial DNA polymerase. *J Biol Chem* 276:40847-57.
19. Larder, B. A. 1995. Viral resistance and the selection of antiretroviral combinations. *J Acquir Immune Defic Syndr Hum Retrovirol* 10 Suppl 1:S28-33.
20. Larder, B. A., B. Chesebro, and D. D. Richman. 1990. Susceptibilities of zidovudine-susceptible and -resistant human immunodeficiency virus isolates to antiviral agents determined by using a quantitative plaque reduction assay. *Antimicrob Agents Chemother* 34:436-41.
21. Lee, L. S., and Y. C. Cheng. 1976. Human deoxythymidine kinase. I. Purification and general properties of the cytoplasmic and mitochondrial isozymes derived from blast cells of acute myelocytic leukemia. *J Biol Chem* 251:2600-2604.
22. Lewis, W., and M. C. Dalakas. 1995. Mitochondrial toxicity of antiviral drugs. *Nat Med* 1:417-22.
23. Lin, T. S., M. Z. Luo, M. C. Liu, S. B. Pai, G. E. Dutschman, and Y. C. Cheng. 1994. Antiviral activity of 2',3'-dideoxy-beta-L-5-fluorocytidine (beta-L-FddC) and 2',3'-dideoxy-beta-L-cytidine (beta-L-ddC) against hepatitis B virus and human immunodeficiency virus type 1 in vitro. *Biochem Pharmacol* 47:171-4.
24. Lin, T. S., M. Z. Luo, M. C. Liu, S. B. Pai, G. E. Dutschman, and Y. C. Cheng. 1994. Synthesis and biological evaluation of 2',3'-dideoxy-L-pyrimidine nucleosides as potential antiviral agents against human immunodeficiency virus (HIV) and hepatitis B virus (HBV). *J Med Chem* 37:798-803.

25. Lin, T. S., M. Z. Luo, M. C. Liu, Y. L. Zhu, E. Gullen, G. E. Dutschman, and Y. C. Cheng. 1996. Design and synthesis of 2',3'-dideoxy-2',3'-didehydro-beta-L-cytidine (beta-L-d4C) and 2',3'-dideoxy 2',3'-didehydro-beta-L-5-fluorocytidine (beta-L-Fd4C), two exceptionally potent inhibitors of human hepatitis B virus (HBV) and potent inhibitors of human immunodeficiency virus (HIV) in vitro. *J Med Chem* 39:1757-9.

26. Lin, T. S., R. F. Schinazi, M. S. Chen, E. Kinney-Thomas, and W. H. Prusoff. 1987. Antiviral activity of 2',3'-dideoxycytidin-2'-ene (2',3'-dideoxy-2',3'-didehydrocytidine) against human immunodeficiency virus in vitro. *Biochem Pharmacol* 36:311-6.

27. Lin, T. S., R. F. Schinazi, and W. H. Prusoff. 1987. Potent and selective in vitro activity of 3'-deoxythymidin-2'-ene (3'-deoxy-2',3'-didehydrothymidine) against human immunodeficiency virus. *Biochem Pharmacol* 36:2713-8.

28. Lu, Z. H., R. Zhang, and R. B. Diasio. 1993. Comparison of dihydropyrimidine dehydrogenase from human, rat, pig and cow liver. Biochemical and immunological properties. *Biochem Pharmacol* 46:945-52.

29. Maag, H., R. M. Rydzewski, M. J. McRoberts, D. Crawford-Ruth, J. P. Verheyden, and E. J. Prisbe. 1992. Synthesis and anti-HIV activity of 4'-azido- and 4'-methoxy-nucleosides. *J Med Chem* 35:1440-51.

30. Medina, D. J., C. H. Tsai, G. D. Hsiung, and Y. C. Cheng. 1994. Comparison of Mitochondrial Morphology, Mitochondrial DNA Content, and Cell Viability in Cultured Cells Treated with Three Anti-Human Immunodeficiency Virus Dideoxynucleosides. *Antimicrob Agents Chemother* 38:1824-1828.

31. Mellors, J. W., G. E. Dutschman, G. J. Im, E. Tramontano, S. R. Winkler, and Y. C. Cheng. 1992. In vitro selection and molecular characterization of human immunodeficiency virus-1 resistant to non-nucleoside inhibitors of reverse transcriptase. *Mol Pharmacol* 41:446-51.

32. O-Yang, C., H. Y. Wu, B. Fraser-Smith, and K. A. M. Walker. 1992. Synthesis of 4'-Cyanothymidine and Analogs as Potent Inhibitors of HIV. *Tetrahedron Letters* 33:37-40.

33. Parker, W. B., and Y. C. Cheng. 1995. "Disruption of Energy Metabolism and Mitochondrial Function", p. 483-490, *Neurotoxicology: Approaches and Methods*. Academic Press Inc., New York.

34. Parker, W. B., and Y. C. Cheng. 1994. Mitochondrial Toxicity of Antiviral Nucleoside Analogs. *The Journal of HIH Research* 6:57-61.

35. Richman, D. D. 1993. Resistance of clinical isolates of human immunodeficiency virus to antiretroviral agents. *Antimicrob Agents Chemother* 37:1207-13.

36. Richman, D. D., M. A. Fischl, M. H. Grieco, M. S. Gottlieb, P. A. Volberding, O. L. Laskin, J. M. Leedom, J. E. Groopman, D. Mildvan, M. S. Hirsch, and et al. 1987. The toxicity of azidothymidine (AZT) in the treatment of patients with AIDS and AIDS-related complex. A double-blind, placebo-controlled trial. *N Engl J Med* 317:192-7.

37. Schinazi, R. F., C. K. Chu, A. Peck, A. McMillan, R. Mathis, D. Cannon, L. S. Jeong, J. W. Beach, W. B. Choi, S. Yeola, and et al. 1992. Activities of the four optical isomers of 2',3'-dideoxy-3'-thiacytidine (BCH-189) against human immunodeficiency virus type 1 in human lymphocytes. *Antimicrob Agents Chemother* 36:672-6.

38. Sommadossi, J. P., Z. Zhou, M. J. Hitchcock, H. M. McClure, M. el Kouni, and E. Cretton. 1992. Catabolism of 2',3'-Didehydro-2',3-DideoxyThymidine (D4T) in Isolated Hepatocytes and in Rhesus Monkeys. *Proc. Annu. Meeting American Cancer Research* 33:A3253. Univ. of Alabama.

39. Yarchoan, R., J. M. Pluda, R. V. Thomas, H. Mitsuya, P. Brouwers, K. M. Wyvill, N. Hartman, D. G. Johns, and S. Broder. 1990. Long-term toxicity/activity profile of 2',3'-dideoxyinosine in AIDS or AIDS-related complex. *Lancet* 336:526-9.

The invention claimed is:

1. A method of treating a viral infection in a patient in need thereof comprising administering to said patient an effective amount of a compound according to the structure:

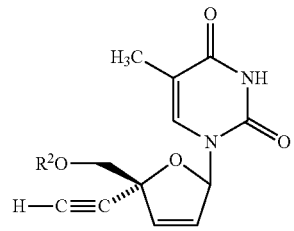

where $R^2$ is H, a $C_2$-$C_{21}$ acyl group, a phosphate, diphosphate, triphosphate or phosphodiester group, or a pharmaceutically acceptable salt thereof, in a pharmaceutically acceptable additive, carrier or excipient, wherein said viral infection is caused by human immunodeficiency virus (HIV).

2. The method according to claim 1 wherein said viral infection is caused by human immunodeficiency virus 1 (HIV 1).

3. The method according to claim 1 wherein said viral infection is caused by human immunodeficiency virus 2 (HIV 2).

4. The method according to claim 1 wherein said compound is coadministered with at least one additional anti-HIV agent.

5. The method according to claim 4 wherein said additional anti-HIV agent is selected from the group consisting of ddC, abacavir, ddI, ddA, 3TC, AZT, D4T, FTC, FddC, Fd4C, Atazanavir, Adefovir dipivoxyl, Tenofovir disoproxil, Etecavir, Indinavir, KHI-227.2-[3-[3-(S)-[[(Tetrahydrofuranyloxy)carbonyl]amino]-4-phenyl-2(R)-hydroxybutyl]]-N-(1,1-dimethylethyl)decahydro-3-isoquinolinecarboxamide, VB-11,328, KNI-174, Val-Val-Sta, CPG53820, HOEt-N2 aza-peptide isostere, 2,5-Diamino-N,N'-bis(N-benzyloxycarbonyluelyl)-1,6-diphenyl-3(S),4(S)-hexanediol BzOCValPhe[diCHOH(SS]PheValBzOC, 2,5,-Diamino-N, N'-bis(N-benzyloxycarbonyluelyl)-1,6-diphenyl-3(R),4(R)-hexanediol BzOCValPhe[diCHOH(RR]PheValBzOC, [bis(SATE)ddAMP], BILA 2186 BS, Agenerase, A-98881, A-83962, A-80987, (2-Naphthalcarbonyl)Asn[decarbonylPhe-hydroxyethyl]ProOtertButyl, A-81525, XM323, Tipranavir, SDZ PRI 053, SD146, Telinavir, (R)2QuinCOAsnPhe[CHOHCH2]PipCONHtBu, Saquinavir, R-87366, DMP 460, L685,434, L685,434-OEtNMe2, L689,502, Lasinavir, Aluviran P9941, Palinavir, and Penicillin.

6. The method according to claim 4 wherein said additional anti-HIV agent is at least one agent selected from the group consisting of ddC, abacavir, ddI, ddA, 3TC, AZT, D4T, FTC, FddC and Fd4C.

7. A method of reducing the likelihood or delaying the onset of a viral infection in a patient at risk for infection, said method comprising administering to said patient an effective amount of a compound according to the structure:

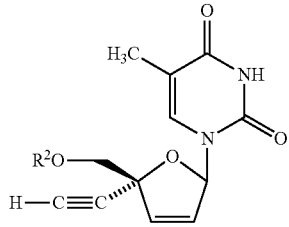

where $R^2$ is H, a $C_2$-$C_{21}$ acyl group, a phosphate, diphosphate, triphosphate or phosphodiester group, or a pharmaceutically acceptable salt thereof, in a pharmaceutically acceptable additive, carrier or excipient, wherein said viral infection is caused by human immunodeficiency virus (HIV).

8. The method according to claim 7 wherein said human immunodeficiency virus is human immunodeficiency virus 1 (HIV-1).

9. The method according to claim 8 wherein said human immunodeficiency virus is HIV 2.

10. The method according to claim 9 wherein said compound is coadministered with at least one additional anti-HIV agent.

11. The method according to claim 9 wherein said additional anti-HIV agent is selected from the group consisting of ddC, abacavir, ddI, ddA, 3TC, AZT, D4T, FTC, FddC, Fd4C, Atazanavir, Adefovir dipivoxyl, Tenofovir disoproxil, Etecavir, Indinavir, KHI-227, 2-[3-[3-(S)-[[(Tetrahydrofuranyloxy)carbonyl]amino]-4-phenyl-2(R)-hydroxybutyl]]-N-(1, 1-dimethylethyl)decahydro-3-isoquinolinecarboxamide, vB-11,328, KNI-174, val-Val-Sta, CPG53820, bis-Val HOEt-N2 aza-peptide isostere, 2,5-Diamino-N,N'-bis(N-benzyloxycarbonyluelyl)-1,6-diphenyl-3(S),4(S)-hexanediol BzOCValPhe[diCHOH(SS]PheValBzOC, 2,5,-Diamino-N,N'-bis(N-benzyloxycarbonyluelyl)-1,6-diphenyl-3(R),4(R)-hexanediol BzOCValPhe[diCHOH(RR]PheValBzOC, [bis(SATE)ddAMP], BILA 2186 BS, Agenerase, A-98881, A-83962, A-80987, (2-Naphthalcarbonyl)Asn[decarbonylPhe-hydroxyethyl]ProOtertButyl, A-81525, XM323, Tipranavir, SDZ PRI 053, SD146, Telinavir, (R)2QuinCOAsnPhe[CHOHCH2]PipCONHtBu, Saquinavir, R-87366, DMP 460, L685,434, L685,434-OEt-NMe2, L689,502, Lasinavir, Aluviran, P9941, Palinavir, and Penicillin.

12. The method according to claim 10 wherein said additional anti-HIV agent is selected from the group consisting of ddC, abacavir, ddI, ddA, 3TC, AZT, D4T, FTC, FddC and Fd4C.

13. A method of reducing the likelihood or delaying the onset of a condition secondary to a viral infection in a patient at risk for the development of said condition, said method comprising administering to said patient an effective amount of a compound according to the structure:

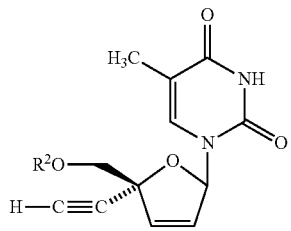

where $R^2$ is H, a $C_2$-$C_{21}$ acyl group, a phosphate, diphosphate, triphosphate or phosphodiester group, or a pharmaceutically acceptable salt thereof, in a pharmaceutically acceptable additive, carrier or excipient, wherein said viral infection is caused by human immunodeficiency virus 1 and/or 2.

14. The method according to claim 13 wherein said condition is AIDS.

15. A method of treating a patient in need thereof for an HIV infection with combination therapy, said method comprising administering to said patient an effective amount of a combination of at least compound according to the structure:

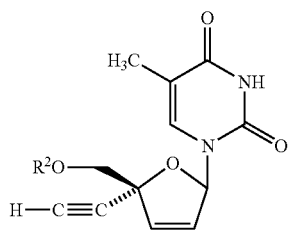

where $R^2$ is H, a $C_2$-$C_{21}$ acyl group, a phosphate, diphosphate, triphosphate or phosphodiester group, or a pharmaceutically acceptable salt thereof, in combination with at least one compound selected from the group consisting of nucleoside reverse transcriptase inhibitors (NRTI), non-nucleoeoside reverse transcriptase inhibitors, protease inhibitors, fusion inhibitors and mixtures thereof.

16. A method of treating a patient in need thereof for an HIV infection with combination therapy, said method comprising administering to said patient an effective amount of a combination of at least compound according to the structure:

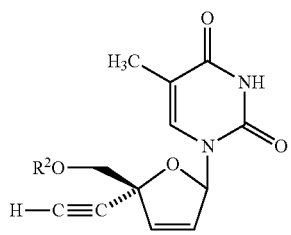

where $R^2$ is H, a $C_2$-$C_{21}$ acyl group, a phosphate, diphosphate, triphosphate or phosphodiester group, or a pharmaceutically acceptable salt thereof with at least one compound selected from the group consisting of 3TC (Lamivudine), AZT (Zidovudine), (-)-FTC, ddI (Didanosine), ddC (zalcitabine), abacavir (ABC), tenofovir (PMPA), D-D4FC (Reverset), D4T (Stavudine), Racivir, L-FddC, L-D4FC, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), T20, fuseon and mixtures thereof.

17. The method according to claim 1 wherein $R^2$ is H and said virus is drug resistant.

18. The method according to claim 2 wherein $R^2$ is H and said virus is drug resistant.

19. The method according to claim 3 wherein $R^2$ is H and said virus is drug resistant.

20. The method according to claim 4 wherein $R^2$ is H and said virus is drug resistant.

21. The method according to claim 5 wherein $R^2$ is H and said virus is drug resistant.

22. The method according to claim 6 wherein $R^2$ is H and said virus is drug resistant.

23. The method according to claim 1 wherein $R^2$ is H and said compound is administered by oral administration.

24. The method according to claim 2 wherein $R^2$ is H and said compound is administered by oral administration.

25. The method according to claim 3 wherein $R^2$ is H and said compound is administered by oral administration.

26. The method according to claim 4 wherein $R^2$ is H and said compound and said additional anti-HIV agent are administered by oral administration.

27. The method according to claim 5 wherein $R^2$ is H and said compound and said additional anti-HIV agent are administered by oral administration.

28. The method according to claim 6 wherein $R^2$ is H and said compound and said additional anti-HIV agent are administered by oral administration.

29. The method according to claim 7 wherein $R^2$ is H and said compound is administered by oral administration.

30. The method according to claim 13 wherein $R^2$ is H and said compound is administered by oral administration.

31. A method of treating a viral infection in a patient in need thereof comprising orally administering to said patient an effective amount of a compound according to the structure

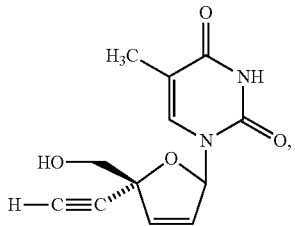

wherein said viral infection is caused by human immunodeficiency virus (HIV).

* * * * *